United States Patent
Le Devedec et al.

(10) Patent No.: US 11,426,356 B2
(45) Date of Patent: *Aug. 30, 2022

(54) CROSSLINKED PARTICLES

(71) Applicants: Pendant Biosciences, Inc., Nashville, TN (US); The Governing Council of the University of Toronto, Toronto (CA)

(72) Inventors: Frantz Le Devedec, Toronto (CA); Christine Allen, Toronto (CA); David M. Stevens, Frederick, MD (US); Dean James Rager-Aguiar, Spring Hill, TN (US); Timothy Tordella Ruckh, Mountain View, CA (US); Carl Eric Elmquist, Franklin, TN (US)

(73) Assignees: Pendant Biosciences, Inc., Nashville, TN (US); The Governing Council of the University of Toronto, Toronto (CA)

( * ) Notice: Subject to any disclaimer, the term of this patent is extended or adjusted under 35 U.S.C. 154(b) by 0 days.

This patent is subject to a terminal disclaimer.

(21) Appl. No.: 16/287,690

(22) Filed: Feb. 27, 2019

(65) Prior Publication Data

US 2019/0262274 A1    Aug. 29, 2019

Related U.S. Application Data

(63) Continuation of application No. 15/289,005, filed on Oct. 7, 2016, now Pat. No. 10,258,578.

(60) Provisional application No. 62/313,013, filed on Mar. 24, 2016, provisional application No. 62/281,631, filed on Jan. 21, 2016, provisional application No. 62/239,758, filed on Oct. 9, 2015.

(51) Int. Cl.
| | |
|---|---|
| *A61K 9/16* | (2006.01) |
| *A61K 31/122* | (2006.01) |
| *A61K 31/337* | (2006.01) |
| *A61K 31/573* | (2006.01) |
| *A61K 31/58* | (2006.01) |
| *A61K 9/51* | (2006.01) |
| *A61K 9/50* | (2006.01) |

(52) U.S. Cl.
CPC .......... *A61K 9/5123* (2013.01); *A61K 9/1641* (2013.01); *A61K 9/1694* (2013.01); *A61K 9/5031* (2013.01); *A61K 9/5089* (2013.01); *A61K 9/5146* (2013.01); *A61K 9/5192* (2013.01); *A61K 31/122* (2013.01); *A61K 31/337* (2013.01); *A61K 31/573* (2013.01); *A61K 31/58* (2013.01)

(58) Field of Classification Search
None
See application file for complete search history.

(56) References Cited

U.S. PATENT DOCUMENTS

| | | |
|---|---|---|
| 10,258,578 B2 | 4/2019 | Le Devedec et al. |
| 2005/0020734 A1 | 1/2005 | Asgarzadeh et al. |
| 2006/0239924 A1 | 10/2006 | Bolotin |
| 2008/0145338 A1 | 6/2008 | Anderson et al. |
| 2011/0257343 A1 | 10/2011 | Harth et al. |
| 2013/0142733 A1 | 6/2013 | Harth et al. |

FOREIGN PATENT DOCUMENTS

| | | |
|---|---|---|
| WO | WO-2013/169938 A2 | 11/2013 |
| WO | WO-2013/169938 A3 | 11/2013 |
| WO | WO-2016/174116 A1 | 11/2016 |

OTHER PUBLICATIONS

Silvers, A.L., et al., Functional Aliphatic Polyesters and Nanoparticles Prepared by Organocatalysis and Orthogonal Grafting Chemistry, J. Polymer Science Part A: Polymer Chemistry (2012) 50, 3517-3529.*
Wu, C., et al., Pure paclitaxel nanoparticles: preparation, characterization, and antitumor effect for human liver cancer SMMC-7721 cells, International Journal of Nanomedicine, 2018:13 6189-6198.*
Zou, et al. "Clicking well-defined biodegradable nanoparticles and nanocapsules by UV-induced thiol-ene cross-linking in transparent miniemulsions." Adv Mater. Oct. 4, 2011; 23(37):4274-7.
Atilla Tasdelen, M. et al. (2015). "Externally stimulated click reactions for macromolecular syntheses," Progress in Polymer Science 52:19-78.
Extended European Search Report dated Apr. 29, 2019 for EP Application No. 16 854 494.8, filed on Oct. 7, 2016, 9 pages.
International Search Report and Written Opinion dated Feb. 27, 2017, for International Application No. PCT/US2016/056135, filed on Oct. 7, 2016, 14 pages.
Jaszcz, K. (2013). "Photocrosslinked poly(ester-anhydride) microspheres with macroporous structure," Polym. Adv. Technol. 24:873-880.
Lowe, A.B. (2014). "Thiol-ene "click" reactions and recent applications in polymer and materials synthesis: a first update", Polymer Chemistry 5:4820.

* cited by examiner

*Primary Examiner* — H. Sarah Park
(74) *Attorney, Agent, or Firm* — Cooley LLP

(57) ABSTRACT

Disclosed are crosslinked particles (e.g., microparticles) that are capable of storing and releasing drugs. The particles can be macroparticles, microparticles, or nanoparticles and can be composed of polyester backbones. The particles can be loaded with a drug. The particles can degrade in vivo to release the drug. The particles can be prepared by crosslinking functionalized polyester backbones and loaded with a given drug. The particles of the present disclosure can be injected with a syringe. In some embodiments, the particles of the present disclosure are administered in connection with a surgery and release the drug after the site of the surgery for a period of 1-6 months.

13 Claims, 55 Drawing Sheets

CROSSLINKED PARTICLES

RELATED APPLICATIONS

This application is a continuation of U.S. patent application Ser. No. 15/289,005, filed Oct. 7, 2016, which claims the benefit under 35 U.S.C. § 119(e) of U.S. Provisional Patent Application Ser. No. 62/239,758, filed Oct. 9, 2015; U.S. Provisional Patent Application Ser. No. 62/281,631, filed Jan. 21, 2016; and U.S. Provisional Patent Application Ser. No. 62/313,013, filed Mar. 24, 2016, the disclosures of which are incorporated herein by reference in their entirety.

FIELD OF THE INVENTION

The present disclosure teaches crosslinked particles (e.g., microparticles or nanoparticles) that are capable of storing and releasing drugs. The particles can release drug by degradation, erosion, diffusion, or a combination of mechanisms.

BACKGROUND OF THE INVENTION

Drug-eluting biodegradable nanoparticles can be used for a variety of biological applications, such as wound healing and arthritis treatment (see e.g., U.S. Pat. No. 7,935,782 and WO 2009/061854, the entire contents of which are hereby incorporated by reference in their entirety). However, it can be difficult to control particle size and morphology to achieve nanoparticles with reproducible results. Additionally, previous attempts to produce crosslinked particles were limited in size and therefore could only be loaded with a limited amount of a given drug. Smaller particles also tended to biodegrade more quickly than larger particles, and were therefore unable to provide sustained release of for a desired duration.

Moreover, current drug delivery particles can suffer from a burst effect, wherein a substantial portion of a drug dispersed therein is released quickly released in a short period followed by a lower release rate. This has the effect of initially over dosing a patient and then later under dosing the patient.

SUMMARY OF THE INVENTION

The present disclosure teaches particles (e.g., microparticles) that are crosslinked and can be used in vivo. The crosslinked particles can include a drug, and can release the drug when used in vivo. In some embodiments, the drug is released as the particle degrades. The microparticles can thus be used to release drugs at the site of wounds, or after surgical procedures to release therapeutic agents and help speed recovery. Additionally, the particles of the current disclosure can be used for the treatment of arthritis. For example, particles comprising arthritis therapeutics can be administered to the site of arthritis pain (e.g., by injection). In some embodiments, the present disclosure provides crosslinked particles such as microparticles that have reproducible size and morphology. In some embodiments, the present disclosure also provides particles that can release a drug for a sustained period of time (e.g., greater than one month) and which do not suffer from a burst effect (e.g., a release of substantial amount of drug soon after immersion in a solvent).

In one aspect, the present disclosure provides a crosslinked degradable particle, comprising:
a plurality of polyester backbones, wherein the plurality of polyester backbones are crosslinked via thioethers, triazoles, or amides; and
a drug dispersed within the crosslinked degradable particle.

In another aspect, the present disclosure provides a crosslinked degradable particle, comprising:
a plurality of polymer backbones obtained from lactone monomer residues, wherein the plurality of polymer backbones are crosslinked via thioethers, triazoles, or amides; and
a drug dispersed within the crosslinked degradable particle, wherein the crosslinked degradable particle has a nominal diameter between 1 µm and 100 µm.

In another aspect, the present disclosure provides a crosslinked degradable particle, comprising:
a plurality of polymer backbones obtained from lactone monomer residues, wherein the plurality of polymer backbones are crosslinked via thioethers, triazoles, or amides; and
a drug dispersed within the crosslinked degradable particle, wherein the crosslinked degradable particle has a nominal diameter between 1 micron and 100 microns.

In another aspect, the present disclosure provides a method of preparing a crosslinked degradable particle, comprising:
combining a polyester containing a plurality of functional groups and a crosslinker to form a mixture; and
reacting the functional groups with crosslinkers to form a crosslinked degradable particle.

In another aspect, the present disclosure provides a method of preparing a crosslinked degradable particle, comprising:
dissolving a polyester containing a plurality of allyl groups, a dithiol, and a photoinitiator in at least one solvent to form a solution;
emulsifying the solution in an aqueous phase to form an emulsion;
irradiating the emulsion with UV light to react the dithiol with two of the allyl groups to form a crosslink; and
evaporating at least a portion of the solvent from the emulsion.

In another aspect, the present disclosure provides a method of preparing a crosslinked degradable particle, comprising:
dissolving a polyester containing a plurality of propargyl groups and a diazide in at least one solvent to form a solution;
emulsifying the solution in an aqueous phase to form an emulsion;
treating the emulsion to react the diazide with two of the propargyl groups to form a crosslink; and
evaporating at least a portion of the solvent from the emulsion.

In another aspect, the present disclosure provides method of preparing a crosslinked degradable particle, comprising:
dissolving a polyester containing a plurality of epoxide groups and a diamine in at least one solvent to form a solution;
emulsifying the solution in an aqueous phase to form an emulsion;
allowing the diamine to react with the epoxide groups to form a crosslink; and
evaporating at least a portion of the solvent from the emulsion.

In another aspect, the present disclosure provides a method of preparing a crosslinked degradable particle, comprising:
dissolving a polyester containing a plurality of carboxylic acid groups and a diamine in at least one solvent to form a solution;
emulsifying the solution in an aqueous phase to form an emulsion;
treating the emulsion to react diamine to react with the carboxylic acid groups to form a crosslink; and
evaporating at least a portion of the solvent from the emulsion.

In another aspect, the present disclosure provides a method of reducing aggregation of a plurality of crosslinked degradable particles, comprising attaching a plurality of polyethylene glycol chains to an exterior of the plurality of crosslinked degradable particles.

In another aspect, the present disclosure provides a method of dispersing a drug within a crosslinked degradable particle, comprising:
swelling the crosslinked degradable particle with a solvent to form a swollen crosslinked degradable particle, wherein the solvent further comprises a drug dispersed therein; and
removing the crosslinked degradable particles from the solvent.

In another aspect, the present disclosure provides a method of preparing a crosslinked degradable implant, comprising:
dissolving a polyester containing a plurality of functional groups and a crosslinker in at least one solvent to form a solution;
treating the solution to react the crosslinker with two of the functional groups to form a crosslink;
wherein the crosslinked degradable implant has a diameter of at least about 1 millimeter.

In another aspect, the present disclosure provides a method of controlling an average size of a distribution of crosslinked degradable particles, comprising:
preparing a plurality of molds of uniform size and shape;
combining a polyester containing a plurality of functional groups and a crosslinker to form a mixture;
dispersing the mixture within the molds; and
treating the mixture to react the crosslinker with two of the functional groups to form a crosslink.

In another aspect, the present disclosure provides a method of controlling an average size of a distribution of crosslinked degradable particles, comprising:
combining a polyester containing a plurality of functional groups and a crosslinker in at least one nonaqueous solvent to form an emulsion wherein the nonaqueous solvent comprises droplets of uniform size,
wherein the polyester and crosslinker, are dissolved in the nonaqueous solvent droplets; and
treating the emulsion to react the crosslinker with two of the functional groups to form a crosslink, wherein the particles are crosslinked while dissolved in the nonaqueous solvent.

In another aspect, the present disclosure provides a crosslinked degradable particle, formed by:
forming a polyester containing a plurality of functional groups and a crosslinker to form a mixture; and
reacting the functional groups with crosslinkers to form a crosslinked degradable particle.

In another aspect, the present disclosure provides a method of treating a disease, comprising:
administering to a subject in need thereof a therapeutically effective amount of the crosslinked degradable particle of the present disclosure containing the drug.

In another aspect, the present disclosure provides use of a crosslinked degradable particle of the present disclosure for the treatment of a disease. In some embodiments, the crosslinked particle contains a drug.

In another aspect, the present disclosure provides the use of a crosslinked degradable particle of the present disclosure in the manufacture of a medicament for the treatment of a disease. In some embodiments, the crosslinked particle contains a drug.

In another aspect, the present disclosure provides a crosslinked degradable particle, comprising:
a polyester backbone of the Formula I:

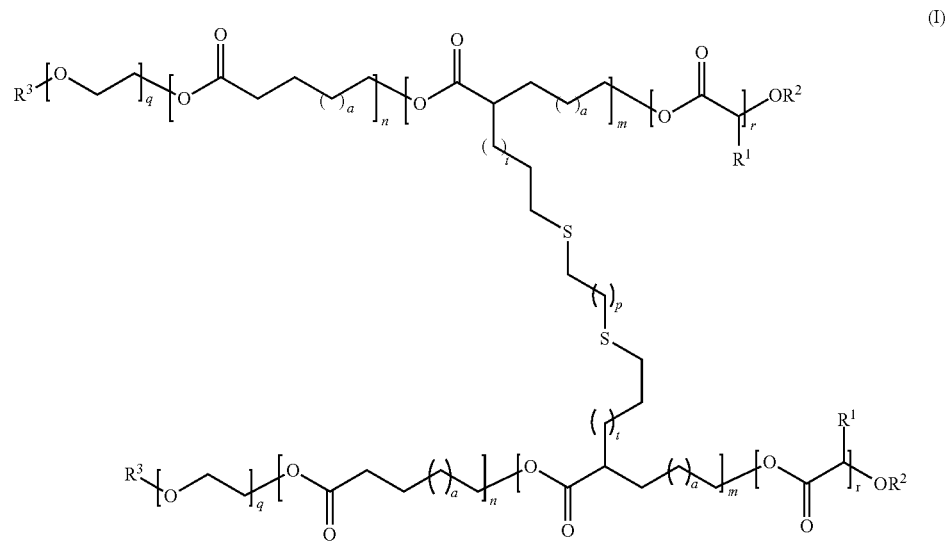

wherein:
R¹ is independently, at each occurrence, —H, or —$C_1$-$C_6$ alkyl;
R² is independently, at each occurrence, —H, or —$C_1$-$C_6$ alkyl;
R³ is independently, at each occurrence, —H, or —$C_1$-$C_6$ alkyl;
a is 0, 1, or 2;
m is independently, at each occurrence, an integer between 1 and 1000, inclusive;
n is independently, at each occurrence, an integer between 1 and 1000, inclusive;
p is independently, at each occurrence, an integer between 0 and 5, inclusive;
q is independently, at each occurrence, an integer between 0 and 1000, inclusive;
r is independently, at each occurrence, an integer between 0 and 1000, inclusive; and
t is independently, at each occurrence, an integer between 0 and 5, inclusive.

In another aspect, the present disclosure provides a cross-linked degradable particle, comprising:
a polyester backbone of the Formula II:

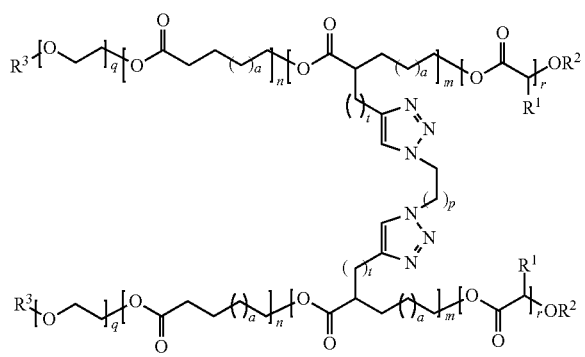

wherein:
R¹ is independently, at each occurrence, —H, or —$C_1$-$C_6$ alkyl;
R² is independently, at each occurrence, —H, or —$C_1$-$C_6$ alkyl;
R³ is independently, at each occurrence, —H, or —$C_1$-$C_6$ alkyl;
a is 0, 1, or 2;
m is independently, at each occurrence, an integer between 1 and 1000, inclusive;
n is independently, at each occurrence, an integer between 1 and 1000, inclusive;
p is independently, at each occurrence, an integer between 0 and 5, inclusive;
q is independently, at each occurrence, an integer between 0 and 1000, inclusive;
r is independently, at each occurrence, an integer between 0 and 1000, inclusive; and
t is independently, at each occurrence, an integer between 0 and 5, inclusive.

In another aspect, the present disclosure provides a cross-linked degradable particle, comprising:
a polyester backbone of the Formula III:

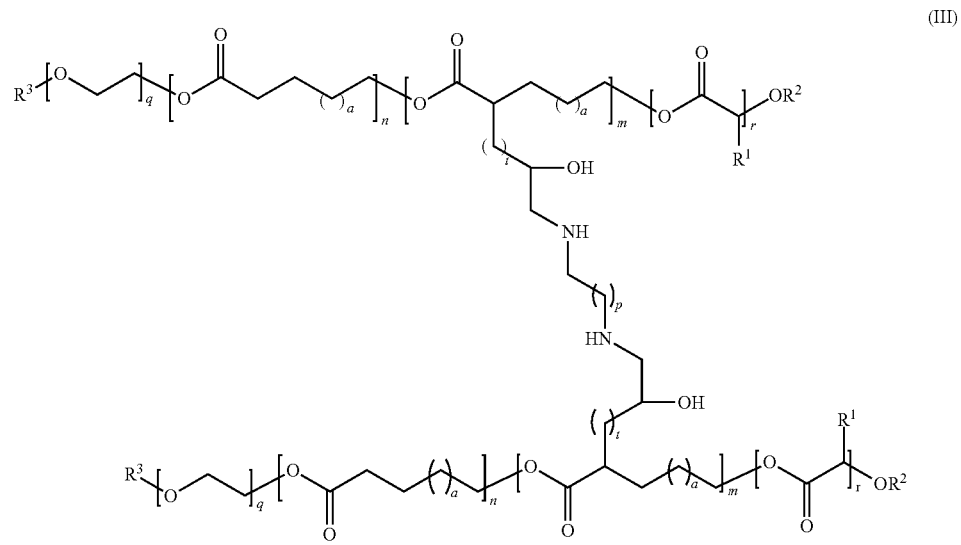

wherein:
R¹ is independently, at each occurrence, —H, or —$C_1$-$C_6$ alkyl;
R² is independently, at each occurrence, —H, or —$C_1$-$C_6$ alkyl;
R³ is independently, at each occurrence, —H, or —$C_1$-$C_6$ alkyl;
a is 0, 1, or 2;
m is independently, at each occurrence, an integer between 1 and 1000, inclusive;
n is independently, at each occurrence, an integer between 1 and 1000, inclusive;
p is independently, at each occurrence, an integer between 0 and 5, inclusive;
q is independently, at each occurrence, an integer between 0 and 1000, inclusive;
r is independently, at each occurrence, an integer between 0 and 1000, inclusive; and t is independently, at each occurrence, an integer between 0 and 5, inclusive.

In another aspect, the present disclosure provides a cross-linked degradable particle, comprising:
a polyester backbone of the Formula IV:

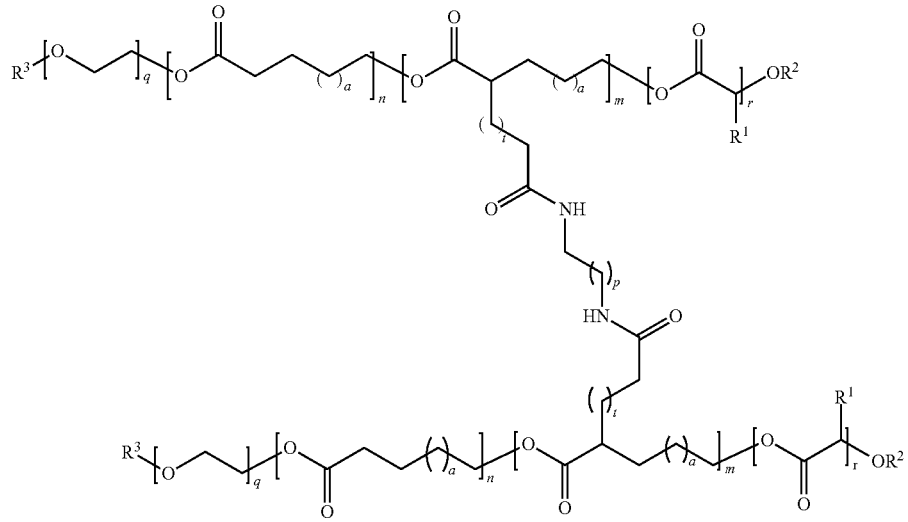

wherein:
$R^1$ is independently, at each occurrence, —H, or —$C_1$-$C_6$ alkyl;
$R^2$ is independently, at each occurrence, —H, or —$C_1$-$C_6$ alkyl;
$R^3$ is independently, at each occurrence, —H, or —$C_1$-$C_6$ alkyl;
a is 0, 1, or 2;
m is independently, at each occurrence, an integer between 1 and 1000, inclusive;
n is independently, at each occurrence, an integer between 1 and 1000, inclusive;
p is independently, at each occurrence, an integer between 0 and 5, inclusive;
q is independently, at each occurrence, an integer between 0 and 1000, inclusive;
r is independently, at each occurrence, an integer between 0 and 1000, inclusive; and
t is independently, at each occurrence, an integer between 0 and 5, inclusive.

In another aspect, the present disclosure provides a cross-linked degradable particle, comprising:
a polyester backbone of the Formula V:

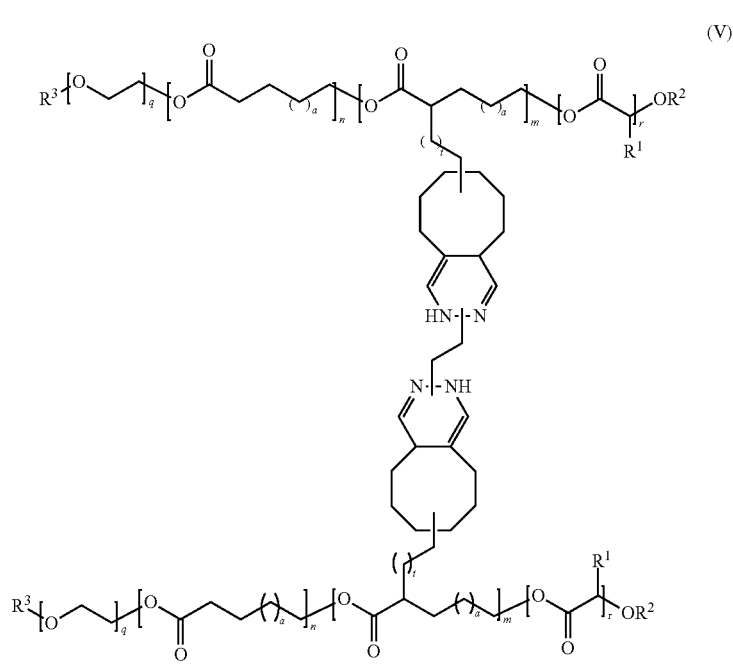

wherein:

$R^1$ is independently, at each occurrence, —H, or —$C_1$-$C_6$ alkyl;

$R^2$ is independently, at each occurrence, —H, or —$C_1$-$C_6$ alkyl;

$R^3$ is independently, at each occurrence, —H, or —$C_1$-$C_6$ alkyl;

a is 0, 1, or 2;

m is independently, at each occurrence, an integer between 1 and 1000, inclusive;

n is independently, at each occurrence, an integer between 1 and 1000, inclusive;

p is independently, at each occurrence, an integer between 0 and 5, inclusive;

q is independently, at each occurrence, an integer between 0 and 1000, inclusive;

r is independently, at each occurrence, an integer between 0 and 1000, inclusive; and t is independently, at each occurrence, an integer between 0 and 5, inclusive.

In another aspect, the present disclosure provides a cross-linked degradable particle, comprising:

a polyester backbone of the Formula VI:

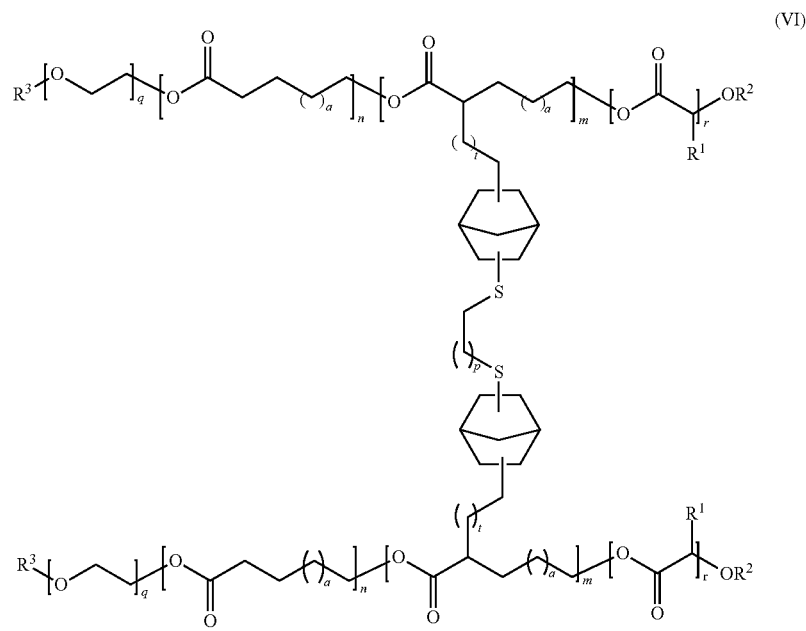

wherein:

$R^1$ is independently, at each occurrence, —H, or —$C_1$-$C_6$ alkyl;

$R^2$ is independently, at each occurrence, —H, or —$C_1$-$C_6$ alkyl;

$R^3$ is independently, at each occurrence, —H, or —$C_1$-$C_6$ alkyl;

a is 0, 1, or 2;

m is independently, at each occurrence, an integer between 1 and 1000, inclusive;

n is independently, at each occurrence, an integer between 1 and 1000, inclusive;

p is independently, at each occurrence, an integer between 0 and 5, inclusive;

q is independently, at each occurrence, an integer between 0 and 1000, inclusive;

r is independently, at each occurrence, an integer between 0 and 1000, inclusive; and t is independently, at each occurrence, an integer between 0 and 5, inclusive.

In another aspect, the present disclosure provides a cross-linked degradable particle, comprising:

a polyester backbone of the Formula VII:

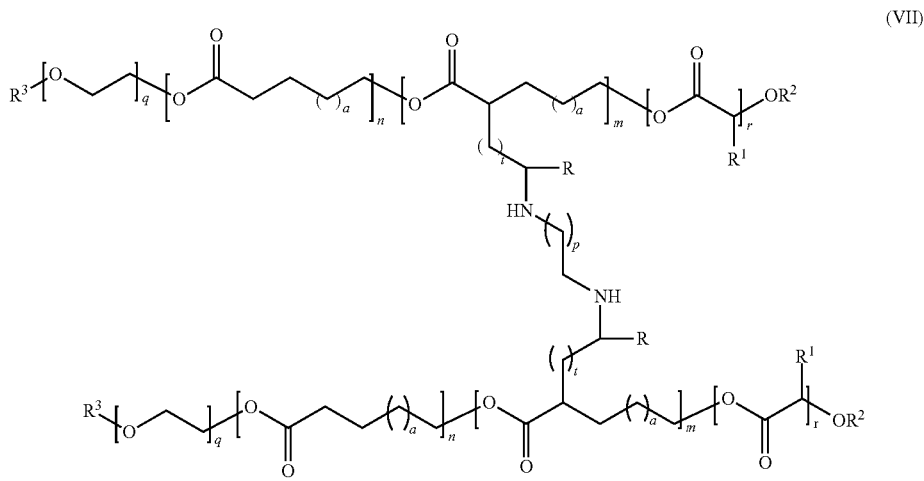

(VII)

wherein:
R is independently, at each occurrence, —H, or —$C_1$-$C_6$ alkyl
$R^1$ is independently, at each occurrence, —H, or —$C_1$-$C_6$ alkyl;
$R^2$ is independently, at each occurrence, —H, or —$C_1$-$C_6$ alkyl;
$R^3$ is independently, at each occurrence, —H, or —$C_1$-$C_6$ alkyl;
a is 0, 1, or 2;
m is independently, at each occurrence, an integer between 1 and 1000, inclusive;
n is independently, at each occurrence, an integer between 1 and 1000, inclusive;
p is independently, at each occurrence, an integer between 0 and 5, inclusive;
q is independently, at each occurrence, an integer between 0 and 1000, inclusive;
r is independently, at each occurrence, an integer between 0 and 1000, inclusive; and
t is independently, at each occurrence, an integer between 0 and 5, inclusive.

The crosslinked particles (e.g., macroparticles, microparticles or nanoparticles) of the present disclosure can have uniform size and shape along with other characteristics such as stability. This can allow the crosslinked particles of the present disclosure to be used in medical settings with high reproducibility and reliability. Additional features and advantages of the present disclosure will be apparent to one of skill in the art and are set forth in the Detailed Description, below.

DETAILED DESCRIPTION OF THE INVENTION

Figure 1A:
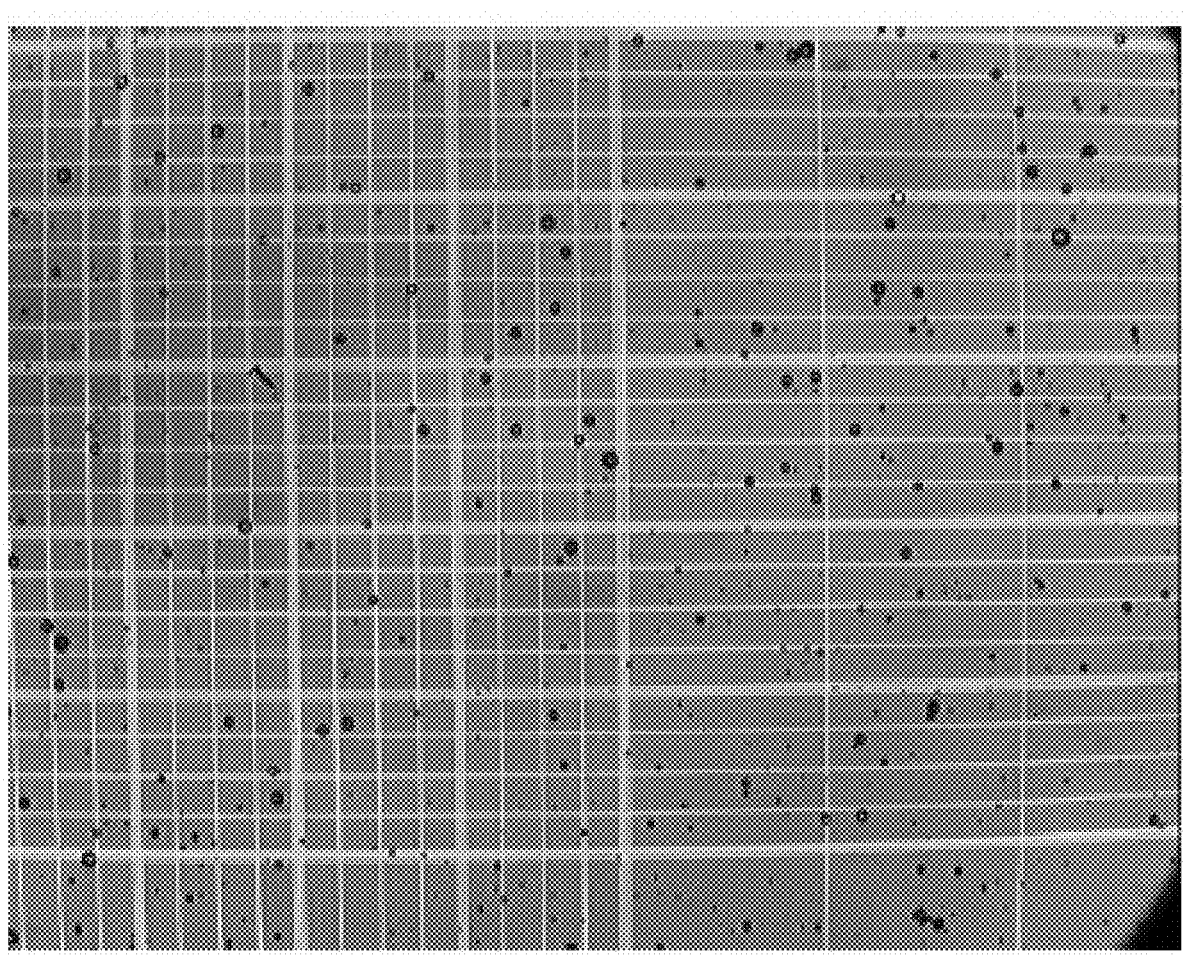
FIG. 1A shows a photo of polycaprolactone (PCL), polyvalerolactone/polyallylvalerolactone copolymer (PVL-co-PAVL) microparticles at a scale of about 1500 μm.

The present disclosure provides crosslinked particles (e.g., microparticles, microparticles or nanoparticles) that can be used in medical applications (e.g., to locally release drugs). In some embodiments, the present disclosure provides microparticles comprising a polyester backbone that can be crosslinked via functional groups disposed along the polyester backbone in the presence of an appropriate crosslinking reagent.

In some embodiments, the polyester backbones are crosslinked via thioethers. The polyester backbones can be crosslinked via triazoles. The polyester backbones can be crosslinked via amides. The polyester backbones can be crosslinked via amines (e.g., via an amine-epoxide reaction). The polyester backbones can be crosslinked by a tetrazine-trans-cyclooctene reaction. The polyester backbones can be crosslinked by a thiol-norbornene reaction. The polyester backbones can be crosslinked by an amine-carbonyl (e.g., aldehyde or ketone) reductive amination. The particles can be biodegradable.

The microparticles of the present disclosure can have a diameter between about 1 µm and about 999 µm, including all ranges and subranges therebetween, and more preferably, the microparticles can have a diameter between about 1 µm and about 100 µm, including all ranges and subranges therebetween. In some embodiments, the microparticles of the present disclosure can have a diameter between about 5 µm and about 30 µm, including all ranges and subranges therebetween (e.g., between about 7 µm and about 15 µm or about 10 µm).

The macroparticles of the present disclosure can have a mean diameter greater than about 1000 µm.

In some embodiments, the drug dispersed within a microparticle of the disclosure can be triamcinolone, triamcinolone acetonide, triamcinolone hexacetonide, and paclitaxel. In some embodiments other compounds such as curcumin can be dispersed within the particles (for instance, curcumin can be used to more easily visualize release kinetics). In some embodiments, curcumin can be used as a surrogate for a drug. In some embodiments, the drug is covalently bonded to the particle. In some embodiments, the drug is contained within the particle by noncovalent interactions. In some embodiments, the particle releases the drug over a period of at least one week in an aqueous environment (e.g., at least 2 weeks, at least 3 weeks, at least 4 weeks, at least 5 weeks, at least 6 weeks, at least 2 months, at least 3 months, at least 4 months, at least 5 months, or at least 6 months). In some embodiments, the particle degrades as it releases the drug.

In some embodiments, the polyester backbone comprises polyvalerolactone (PVL), polycaprolactone (PCL), polylactic acid (PLA), polyglycolic acid (PGC), or a combination thereof. In some embodiments, the particle is a macroparticle. In some embodiments, the particle is a microparticle. In some embodiments, the particle is a nanoparticle. In some embodiments, the polyester backbone further comprises polyethylene glycol (PEG). In some embodiments, the polymer backbone is obtained from a monomer residue comprising valerolactone (e.g., polyvalerolactone), caprolactone (e.g., polycaprolactone), lactic acid (e.g., polylactic acid), glycolic acid (e.g., polyglycolic acid), or a combination thereof. In some embodiments, the lactone monomer is selected from the group consisting of lactic acid, glycolic acid, valerolactone, caprolactone, lactide, or a combination thereof.

In one or more embodiments, any of the valerolactone, caprolactone, lactic acid, lactide, or glycolic acid is functionalized with a functional group. In some embodiments, the functional group can be selected from an allyl group, a propargyl group, or a carboxylic acid group (e.g., the functional groups can be allyl lactide, allyl valerolactone and the like). Alternatively, the functional group can be a transcyclooctene, norbornene, or a carbonyl group (e.g., an aldehyde or ketone). Alternatively, the functional group can be a thiol group, an amine, or a tetrazine.

In one or more embodiments, the polyester and crosslinker are combined in a solvent to form the mixture. In some embodiments of any of the above methods, particles of the disclosure are made by emulsifying the mixture, wherein the polyester and the crosslinker are in the same phase. In some embodiments, the methods further comprise evaporating at least part of the solvent prior to reacting the functional groups with the crosslinker. In some embodiments, the functional group of the polyester backbone comprises an olefin group (e.g., an allyl group), an alkynyl group (e.g., a propargyl group), an epoxy group, a carboxylic acid group, or a carboxylic acid derivative (e.g., an ester or amide).

In some embodiments, particles (e.g., microparticles) of the present disclosure can be formed by electrospraying. In some embodiments, particles (e.g., microparticles) of the present disclosure can be formed by spray-drying.

In some embodiments, the crosslinker comprises a dithiol group. In some embodiments, the dithiol group forms a thioether with an olefin functional group on the polyester backbone. In some embodiments, the crosslinker comprises a diazide. In some embodiments, the diazide forms a triazole with a propargyl functional group on the polyester backbone. In some embodiments, the crosslinker comprises a diamine. In some embodiments, diamine forms a β-hydroxy amine with an epoxide functional group on the polyester backbone. In some embodiments, the diamine forms an amide with a carboxylic acid functional group on the polyester backbone.

In some embodiments, the step of treating the emulsion comprises heating the emulsion or adding a catalyst (e.g., a cyclization catalyst such as a copper or rhodium salt such as a copper (I) salt). In some embodiments, the catalyst for forming an amide crosslinker is an amide coupling catalyst such as N,N'-dicyclohexylcarbodiimide or diisopropylcarbodiimide. In some embodiments, the polyester backbones comprise polyvalerolactone, polycaprolactone, polylactic acid, polyglycolic acid, or a combination thereof. In some embodiments, the polyester backbones are crosslinked by thioethers, triazoles, or amides. For example, in any of the above-embodiments, the act of combining a polyester with a plurality of functional groups and a crosslinker can further comprise also adding an initiator (e.g., a photoinitiator) and/or a catalyst (e.g., a copper catalyst).

In some embodiments of any of the above-methods, the solution (e.g., the emulsion in which the particles are formed further comprises an initiator (e.g., a photoinitiator). In some embodiments, the method of treating the solution comprises irradiating the photoinitiator with ultraviolet light. In some embodiments, a dithiol group forms a thioether with an olefin functional group on the polyester backbone. In some embodiments, the thioether is formed by a radical reaction. In some embodiments, the radical reaction is initiated by a photoinitiator and treatment with ultraviolet light. In some embodiments, the crosslinker comprises a diazide. In some embodiments, the diazide forms a triazole with a propargyl functional group on the polyester backbone. In some embodiments, the triazole is formed in the presence of a copper (I) catalyst.

Definitions

The articles "a" and "an" are used in this disclosure to refer to one or more than one (i.e., to at least one) of the grammatical object of the article. By way of example, "an element" means one element or more than one element.

The term "and/or" is used in this disclosure to mean either "and" or "or" unless indicated otherwise.

"Alkyl" refers to a straight or branched chain saturated hydrocarbon. $C_1$-$C_6$alkyl groups contain 1 to 6 carbon atoms. Examples of a $C_1$-$C_6$alkyl group include, but are not limited to, methyl, ethyl, propyl, butyl, pentyl, isopropyl, isobutyl, sec-butyl and tert-butyl, isopentyl and neopentyl.

The term "treating" with regard to a subject, refers to improving at least one symptom of the subject's disorder. Treating includes curing, improving, or at least partially ameliorating the disorder.

The term "disorder" is used in this disclosure to mean, and is used interchangeably with, the terms disease, condition, or illness, unless otherwise indicated.

The term "administer", "administering", or "administration" as used in this disclosure refers to either directly administering a disclosed particle (e.g., a microparticle) or pharmaceutically acceptable salt of the disclosed particle or a composition to a subject.

As used herein the term "backbone" is understood to mean a polyester chain The polyester backbones of the present disclosure can be crosslinked to form particles such as microparticles or nanoparticles as disclosed herein.

As used herein, a "particle" is a discrete unit comprising polymer backbones as set forth herein that has been crosslinked. The particle can be a nanoparticle, a microparticle, or a macroparticle. The particle may include a drug dispersed therein.

A "nanoparticle" is understood as a crosslinked particle of the present disclosure with a diameter of between about 1 nm and about 999 nm, including all size ranges and subranges therebetween.

A "microparticle" as used herein is understood as a crosslinked particle of the present disclosure with a diameter of between about 1 μm (1,000 nm) and about 999 μm including all size ranges and subranges therebetween. As noted above, the microparticles can have a diameter between about 1 μm and about 100 μm, including all ranges and subranges therebetween. In some embodiments, the microparticles of the present disclosure can have a diameter between about 5 μm and about 30 μm, including all ranges and subranges therebetween (e.g., between about 7 μm and about 15 μm or about 10 μm).

A "macroparticle" as used herein is understood as a crosslinked particle of the present disclosure with a diameter of between about 1 mm (1,000 μm) and about 100 mm, including all size ranges and subranges therebetween. As used herein, a "macroparticle" can be a device or implant. In some embodiments, a single macroparticle can be visible to the naked eye. In some embodiments, macroparticles are referred to as "cylinders."

As used herein, a "drug" is any small molecule therapeutic agent. A drug can be, without limitation, a steroid such as triamcinolone, triamcinolone acetonide, triamcinolone hexacetonide, or paclitaxel. A "drug" can also include a visualizing agent such as curcumin.

A "patient" or "subject" is a mammal, e.g., a human, mouse, rat, guinea pig, dog, cat, horse, cow, pig, or non-human primate, such as a monkey, chimpanzee, baboon, or rhesus.

Particles of the present disclosure can be used in medical applications. For example, particles can be used to heal a wound (e.g., as antiseptics). A wound is understood as an injury to living tissue. Wounds can be caused by cuts, blows, or impacts. Wounds can also be the result of a surgery. Accordingly, in some embodiments, the compounds of the present disclosure can be used to help heal wounds after a surgery. The particles of the present disclosure can be injected (e.g., with a syringe). In some embodiments, the particles of the present disclosure are administered during a surgery and remain after the surgery (e.g., for a period of 1-6 months).

The definition of the crosslinking density of the particle is based on the percentage of the pendant functionality (e.g., allyl, propargyl, or epoxy) of the linear polymer precursor (e.g., polyester) (van der Ende, A. E., et al. (2008) J. Am Chem. Soc. 130, p. 8706). As used herein, the term "crosslinking density" refers to the proportion of functionalized monomer (e.g., allyl valerolactone) used in preparing a polymer such as a copolymer, expressed as a weight percentage of monomers used. For example, if 4% allylvalerolactone and 96% valerolactone are used (by weight) to prepare a polymer backbone, then the crosslinking density of the resulting particle is understood to be 4%. Actual crosslinking density can be determined by analytical techniques including, but not limited to, infrared spectroscopy, pyrolysis gas chromatography, and nuclear magnetic resonance.

The crosslinking densities of the particles of the present disclosure can be between 1% and 100%, inclusive. In some embodiments, the crosslinking density is about 1%, about 2%, about 3%, about 4%, about 5%, about 6%, about 7%, about 8%, about 9%, or about 10%.

As used herein, the term "VL" is understood to mean valerolactone.

Preparation of Microparticles

Microparticles of the present disclosure can be prepared by dissolution of functionalized polyesters in a solvent along with a crosslinker and subsequent crosslinking of the mixture. The resulting product is a plurality of crosslinked microparticles. As set forth in Examples 3 and 4, microparticles comprising PCL with (polyallylvalerolactone-polyvalerolactone) PAVL-PVL (Example 3) and PAVL-PVL (Example 4) were crosslinked using hexanedithiol in the presence of 2,2-dimethoxy-2-phenylacetophenone (DMPA) by irradiation with ultraviolet (UV) light. The microparticles thus produced (see e.g., FIGS. 1A-2D) were in insoluble in dimethyl sulfoxide (DMSO). This demonstrates that the particles produced as described herein are discrete units that are structurally different from the polymeric (e.g., polyester) precursors (or backbones). Without wishing to be bound by theory, crosslinking affords structural integrity to the particles.

In contrast to the crosslinked particles, Comparative Examples 3 and 4 demonstrate microparticles that are produced in the absence of a crosslinker. Comparative Examples 3 and 4 combine PCL with PAVL-PVL (Comparative Example 3) and PAVL-PVL (Comparative Example 4) with UV light in the absence of a crosslinker (e.g., hexanedithiol). Because no crosslinking can occur in the absence of a crosslinker, no microparticles were formed. Accordingly, the polyesters remained intact and were soluble in DMSO. Therefore, in some embodiments, it is necessary to crosslink the polyesters described herein in order to form microparticles and in order to ensure desired characteristics such as stability and size.

Figure 3A:
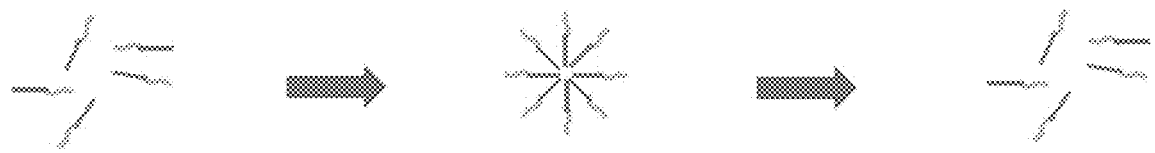
FIG. 3A shows a schematic of self-assembly of amphiphilic block copolymers into micellar structures.

Without wishing to be bound by theory, polymer backbones that are incapable of crosslinking (e.g., PLGA polymers) can be dependent upon micelle concentration in order to form. For example, as set forth in FIG. 3A, amphiphilic block copolymers can self-assemble into micellar structures. However, such micelles can fall apart below the critical micelle concentration (CMC).

Figure 3B:
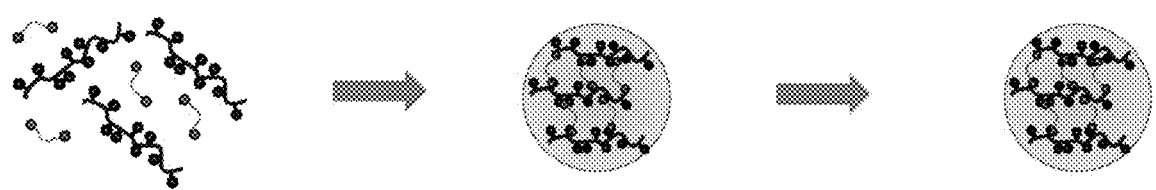
FIG. 3B shows a schematic of encapsulation of polymers and crosslinkers of the present disclosure into the lipid phase of a lipid-water emulsion.

In contrast, as set forth in FIG. 3B, compounds of the present disclosure comprise functionalized polymers and reactive crosslinkers and are covalently crosslinked in a particle (e.g., nanoparticle or microparticle) structure. Thus the particles of the present disclosure remain intact regardless of concentration and are not dependent upon the critical micelle concentration.

According to embodiments of the present disclosure, the microparticles are crosslinked. Schemes 1 through 3 below show general routes to the crosslinked particles of the present disclosure.

Scheme 1 General Crosslinking Scheme using PAVL-PVL Backbone and 2,2'-(ethane-1,2-diylbis(oxy))bis(ethane-1-thiol) Crosslinker

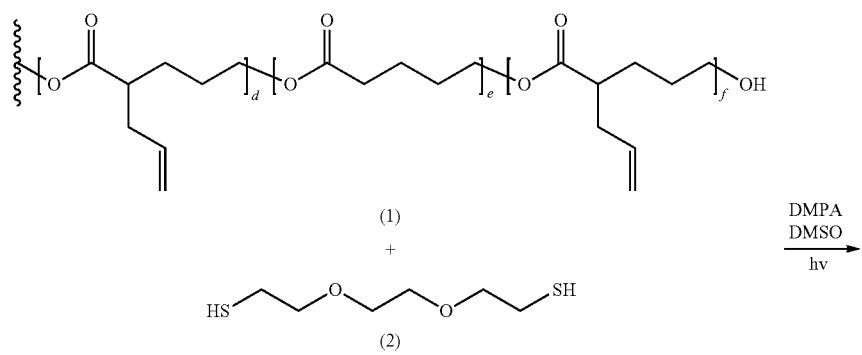

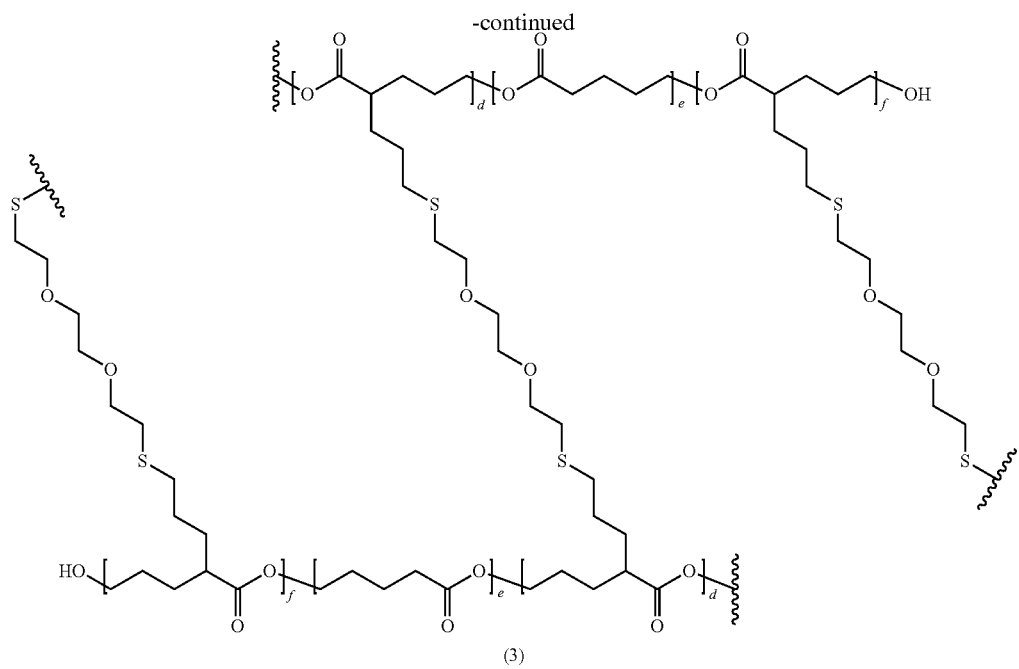

(3)

As shown in Scheme 1, a polyester comprising polyvalerolactone and polyallylvalerolactone (1) can be crosslinked in using a disulfide (2) in the presence of a radical initiator (e.g., a photoinitiator such as DMPA). The ratio of DMPA per allyl group can be adjusted to control the properties of the resulting microparticle (e.g., to produce more or less crosslinking). For instance, in some embodiments 0.2 equivalents of DMPA per allyl group can be added. In some embodiments, one thiol group in (2) can be added for each allyl group in (1). Upon treatment of the mixture of (1) and (2) with UV light (e.g., 365 nm), the allyl groups can crosslink with the thiol groups of the crosslinker to produce a crosslinked microparticle (3). As used in Scheme 1, the values for d, e, and f can each independently be any integer between 1 and 1000, inclusive.

Scheme 2 General Crosslinking Scheme using PAVL-PVL Backbone and 1,6-hexanedithiol Crosslinker

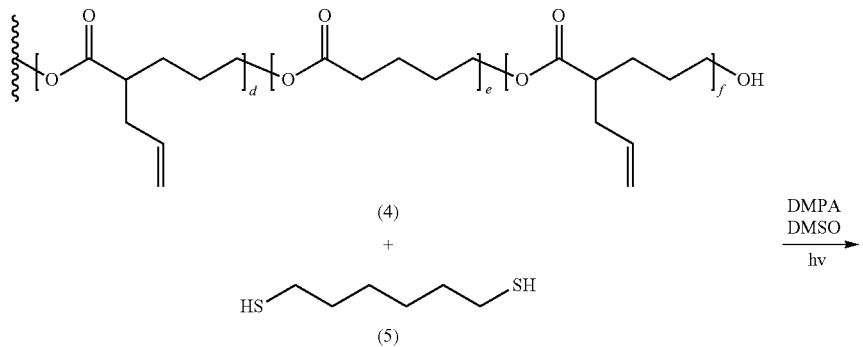

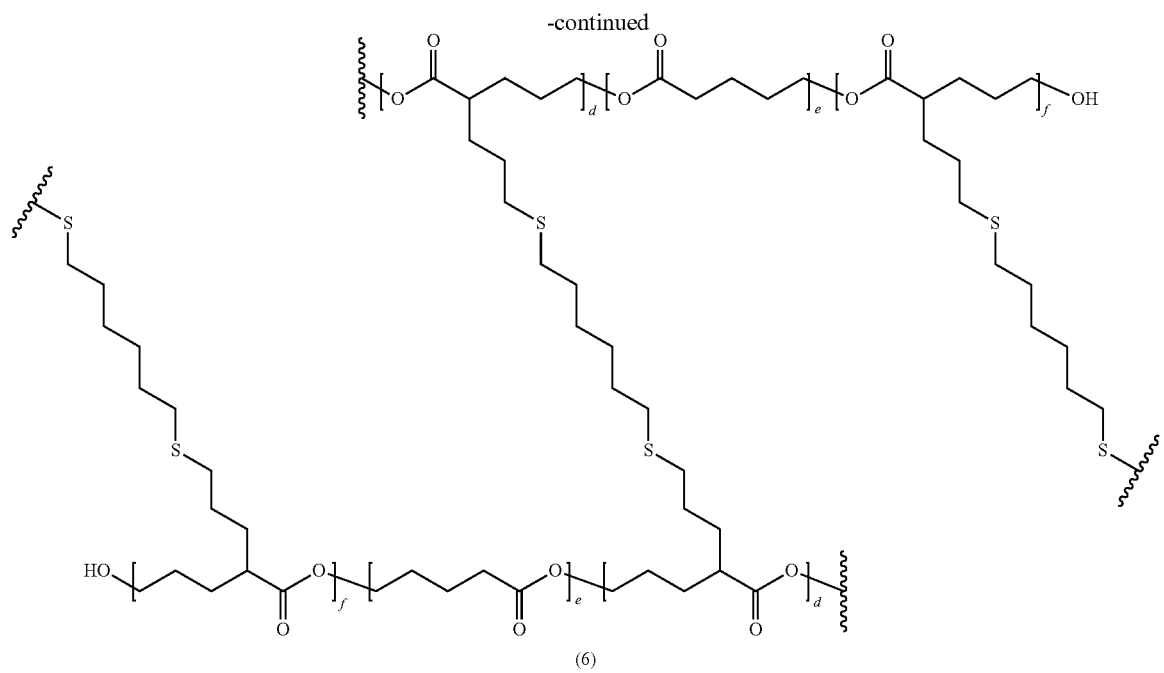

(6)

As shown in Scheme 2, a polyester comprising polyvalerolactone and polyallylvalerolactone (4) can be crosslinked in using a disulfide (5) in the presence of a radical initiator (e.g., a photoinitiator such as DMPA). The ratio of DMPA to allyl groups can be adjusted to control the properties of the resulting microparticle (e.g., to adjust the rate of crosslinking and to produce more or less crosslinking). For instance, in some embodiments 0.2 equivalents of DMPA per allyl group can be added. In some embodiments, one thiol group in (5) can be added for each allyl group in (4). Upon treatment with UV light (e.g., 365 nm), the allyl groups can crosslink with the thiol groups of the crosslinker to produce a crosslinked microparticle (6). As used in Scheme 2, the values for d, e, and f can each independently be any integer between 1 and 1000, inclusive.

In some embodiments, crosslinking can take place by the reaction of an amine group with a carbonyl (e.g., a reductive amination). As shown below in Scheme 3, a polymer backbone functionalized with carbonyl groups (e.g., aldehydes or ketones such as methyl ketones) can react with a diamine to form carbon-nitrogen bonds. Such reactions can be facilitated by a reducing agent (e.g., sodium cyanoborohydride), optionally in the presence of an acid (e.g., acetic acid).

Scheme 3 - General Crosslinking Scheme using Carbonyl-Functionalized Backbones and Diamine Crosslinkers

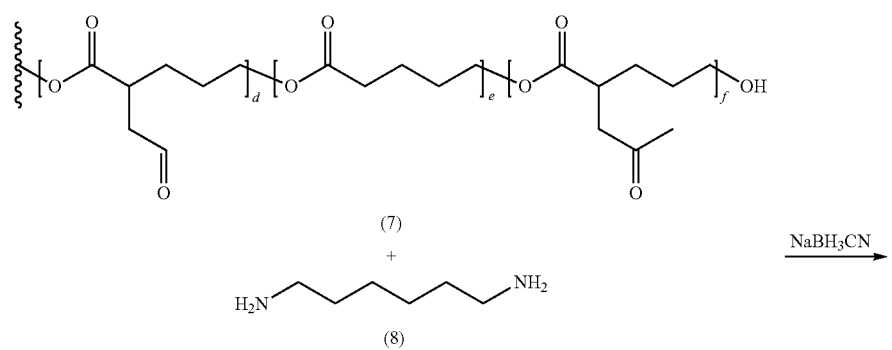

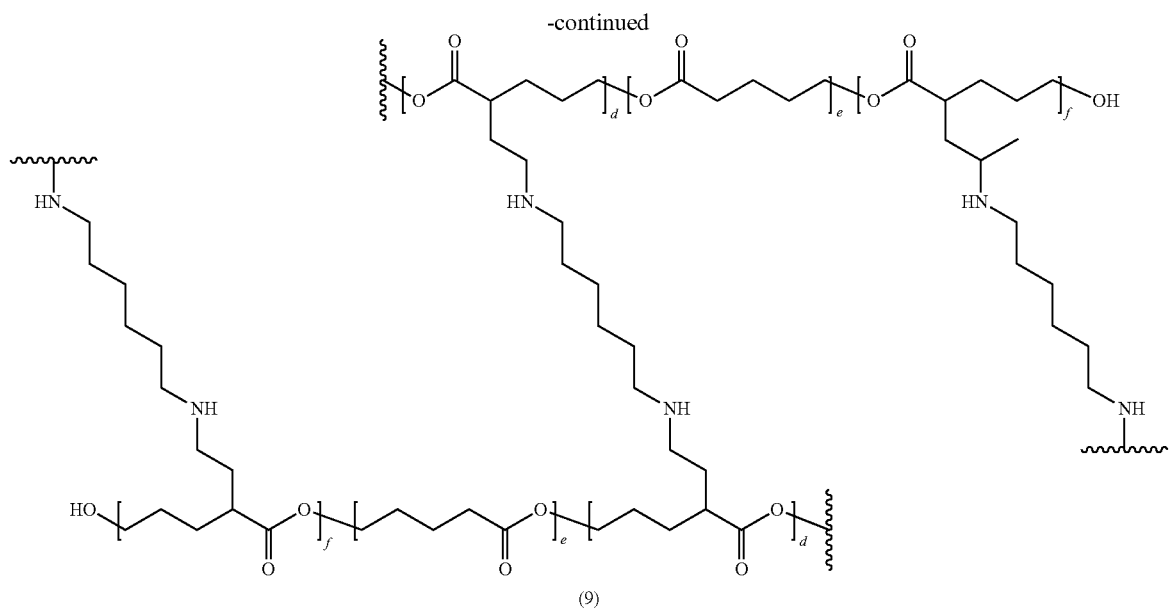

(9)

Scheme 3 shows a reductive amination between a diamine (8) and a polymer backbone that is functionalized with an aldehyde and a methyl ketone (7) to produce a crosslinked polymer (9). One of skill in the art will understand that it is possible to carry out a crosslinking reductive amination using, for instance, only aldehydes, or only ketones (e.g., phenyl ketones, ethyl ketones, and the like), or a mixture of both aldehydes and ketones. As set forth in Scheme 3, the variables d, e, and f can be integers between 1 and 1000, inclusive.

In some embodiments, the microparticles of the present disclosure can be made from functionalized polymer backbones. That is, as set forth below, the polymer backbones can be functionalized with, for instance, olefin (e.g., allyl), alkynyl (e.g., propargyl), or epoxy groups. Thus, embodiments the particles of the present disclosure are not made entirely from unfunctionalized poly(lactic-co-glycolic acid) (PLGA), which historically can be difficult to functionalize. However, in some embodiments, unfunctionalized PLGA could be incorporated into portions of a copolymer backbone that also includes other functionalized polymers in the copolymer backbone.

Functionalization of the polymers of the present disclosure can enable one of skill in the art to customize the features of the particles. For example, as set forth below, the adjustment of the ratios and types of crosslinker and polymer can allow for alterations in, e.g., porosity, drug loading and release, and rates of degradation.

Polyesters

A variety of different polyester backbones can be used to form particles of the present disclosure. For example, in some embodiments the polyester backbones are made from polycaprolactone (PCL). In some embodiments, the polyester backbones are made from polyvalerolactone (PVL). In some embodiments, the PCL or PVL can be functionalized with an allyl group to produce polyallylcaprolactone (PACL) or polyallylvalerolactone (PAVL). In some embodiments, polyesters of the present disclosure are copolymers comprising two or more different monomers. For example, polyesters can comprise PVL and PAVL; PCL and PACL; PVL and PACL; or PCL and PAVL. In some embodiments, polyesters of the present disclosure can further comprise polylactic acid and/or polyglycolic acid. In some embodiments, any of the polyvalerolactone, polycaprolactone, polylactic acid, or polyglycolic acid can be functionalized with a functional group. For example, any of the polyvalerolactone, polycaprolactone, polylactic acid, or polyglycolic acid can further include an ally group, a propargyl group, or a carboxylic acid (or carboxylic acid derivative) disposed along the polymer backbone. The functional group can be used to crosslink the polymer backbone with another polymer backbone. In some embodiments, the copolymers of the disclosure can be block copolymers or random copolymers.

For instance, in one embodiment, the polyester backbone can comprise a copolymer of polyvalerolactone and polyallylvalerolactone (PVL-co-PAVL):

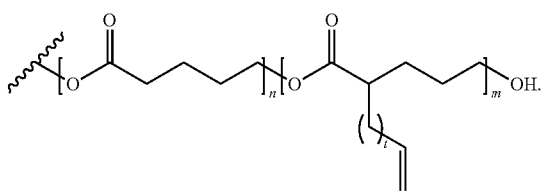

The values of m and n are integers and can each independently fall between about 1 and 1,000. For instance, when n is about 48 and m is about 15, the molecular weight is about 7,000 g/mol. When n is about 128 and m is about 14, the molecular weight is about 14,760 g/mol.

In another embodiment, the polyester backbone can comprise a stabilizer (e.g., a PEG stabilizer). For example, a polyester backbone can comprise mPEG2k-b-PVL-co-PAVL:

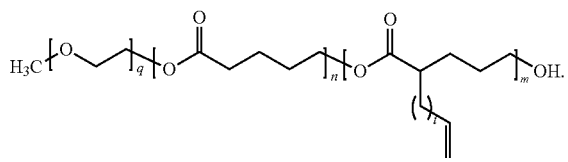

The values of m, n and q are each integers and can each independently fall between about 1 and 1,000. For example when q is about 50, n is about 40, and m is about 9, the molecular weight of the polyester is about 7,500 g/mol.

In another embodiment, the polyester backbone can comprise polyallyl lactide. The polyallyl lactide can be formed from polymerization of allyl lactide. For example, a polyester backbone can comprise a copolymer of polyvalerolactone and polyallyllactide (PVL-co-PAL):

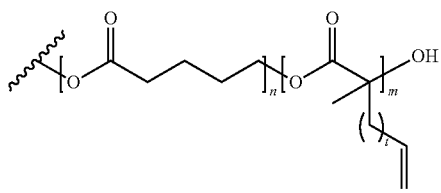

The polyesters of the present disclosure can be prepared using a variety of different suitable monomers. For example, valerolactone can be used to prepare polyvalerolactone, and allylvalerolactone can be used to prepare polyallylvalerolactone. Similarly, caprolactone can be used to prepare polycaprolactone, and allylcaprolactone can be used to prepare polyallylcaprolactone. In some embodiments, lactic acid, glycolic acid, allyl lactide, and combinations thereof can be used as monomers to prepare the polyesters disclosed herein. One of skill in the art will readily understand how to select an appropriate monomer to arrive at a desired polyester backbone.

In any of the embodiments disclosed herein, the polyesters of the present disclosure can further comprise polyethyleneglycol (PEG). In some embodiments, the PEG can connect two different sections of polyester. That is, the PEG can be dispersed between ester-containing portions of the polyester backbone. Alternatively, in some embodiments, the PEG can be attached at the end of the polymer (i.e., the PEG can comprise a terminal portion of the polymer). Thus, in some embodiments, the PEG is found primarily towards the outside of the microparticles.

In some embodiments, crosslinked polymers of the present disclosure can further include additional polymers entangled therein. In some embodiments, compositions of the present disclosure can include PVL and/or PAVL polymer backbones crosslinked together. In some embodiments, the present disclosure includes PVL and/or PAVL polymer backbones crosslinked together with PCL entangled therein. In some embodiments, the present disclosure can include PVL and/or PAVL polymerized onto PCL backbones, or PVL and or PAVL portions crosslinked together. In some embodiments, the present disclosure can include PVL and/or PAVL and PEG polymer backbones crosslinked together.

Crosslinkers

The present disclosure provides for a number of different crosslinkers and crosslinking strategies that can be used to crosslink and form the microparticles described herein. In one embodiment, crosslinking can take place in the presence of a radical initiator (e.g., a photoinitiator). In some embodiments, the crosslinking reaction can be a radical thiol-ene reaction. For example, as set forth in Examples 3 and 4, a photoinitiator (i.e., 2,2-dimethoxy-2-phenylacetophenone) can be used to crosslink a hexanedithiol crosslinker with the allyl functional groups present on a PAVL-PVL polymer backbone. One of skill in the art will recognize that a photoinitiator can be used create radicals (e.g., in the presence of UV light). In some embodiments, photoinitiators do not require heat to produce radicals. The radicals thus created can initiate a thiol-ene chain reaction between the thiols on the hexanedithiol with the olefin functionality (e.g., of the ally group) of PAVL to crosslink the polyester backbones and produce particles (e.g., microparticles or nanoparticles). One of skill in the art will appreciate that additional radical initiators can be used to initiate a crosslinking reaction such as the thiol-ene reaction. For example, other radical initiators can include, without limitation, thermal initiators, halogens such as chlorine, bromine, and iodine, azo compounds such as azobisisobutyronitrile (AIBN), and organic peroxides such as di-tert-butyl peroxide and benzoyl peroxide.

In some embodiments, the radical initiator can be a drug itself. For instance, using a drug that can form radicals to initiate a crosslinking chain reaction can simultaneously lead to the creation of crosslinked particles (e.g., microparticles) as well as ensure that the drug is dispersed within the particles. In some embodiments, a drug can be an initiator for crosslinking of the polymer backbones (e.g., polyester backbone) to form a particle of the present disclosure. Additionally, the radical initiators of the present disclosure need not be photoinitiators. In some embodiments, the radical initiators used herein can create radicals, for instance, thermally (e.g., upon heating). The amount of time necessary to crosslink polyesters using UV exposure can be, for instance, between about 1 and about 60 minutes. For example, an emulsion of the present disclosure can be exposed to UV light for about 1, about 5, about 10, about 15, about 20, about 25, about 30, about 35, about 40, about 45, about 50, or about 60 minutes.

Additionally, crosslinking can take place via the formation of a triazole from the reaction between an alkyne group and an azide group. For example, polyesters of the present disclosure can be functionalized with an alkynyl group (e.g., a propargyl group). The alkynyl group can react in the presence of a diazide (e.g., 1,6-hexanediazide). The alkynyl groups on the polyester chains can react to form triazoles with the crosslinkers (e.g., via the azide-alkyne Huisgen cycloaddition), thus creating particles (e.g., microparticles). One of skill in the art will understand that this reaction can be carried out in the presence of a catalyst. For instance, the cycloaddition reaction can be carried out in the presence of a copper (I) salt (e.g., cuprous bromide or cuprous iodide). In some embodiments, the reaction can be carried out in the presence of a copper (II) salt (e.g., copper (II) sulfate) and a reducing agent (e.g. sodium ascorbate) to produce copper (I) in situ. In some embodiments, the cycloaddition reaction takes place in the absence of a catalyst. For example, in some embodiments, the cycloaddition reaction can take place upon heating the mixture.

In some embodiments, crosslinking can take place via the formation of amide bonds (—C(O)NR—). For example, in some embodiments crosslinking can be effected by amide formation between a polyester of the disclosure that has been functionalized with a carboxylic acid group (or a carboxylic acid derivative) and a diamine (e.g., 1,6 hexanediamine). The amide formation can take place in the presence of a peptide coupling catalyst such as N,N'-Dicyclohexylcarbodiimide ("DCC"), 2-(1H-benzotriazol-1-yl)-1,1,3,3-tetramethyluronium hexafluorophosphate ("HBTU"), or 1-[Bis(dimethylamino)methylene]-1H-1,2,3-triazolo[4,5-b]pyridinium 3-oxid hexafluorophosphate ("HATU"). In some embodiments, the amide coupling reagent can be added after the carboxylic acid group and the diamine are dissolved in the same phase. One of skill in the art will further recognize that it is possible to form amide linkages in the absence of a peptide coupling reagent. For example, amide bonds can be formed by heating a mixture of carboxylic acid groups (e.g., in the presence of an acid). Alternatively, amide bonds can be formed between amines and carboxylic acid derivatives. For example, a crosslinking amide bond can be formed by treatment of an ester or non-crosslinked amide with a crosslinking amine group.

In some embodiments, crosslinking can take place via the formation of a β-hydroxy amine. For example, crosslinking can take place between an epoxide group disposed along a polyester backbone as described herein and an amine moiety. The diamines can react with the epoxides (e.g., nucleophilic attack) to form carbon-nitrogen bonds. One of skill in the art will understand that the regiochemistry of the β-hydroxy amine-forming reaction can be controlled by the reaction conditions (e.g., use of acid or basic catalysis). For example, one can influence whether a monosubstituted epoxide opens at the terminal position by using basic catalysis. Thus, as shown in Scheme 4, below, one of skill in the art will understand that multiple outcomes of amine-epoxy reaction are possible in the reaction between an epoxide-functionalized backbone (10) and a diamine (11) to arrive at a crosslinked particle (12):

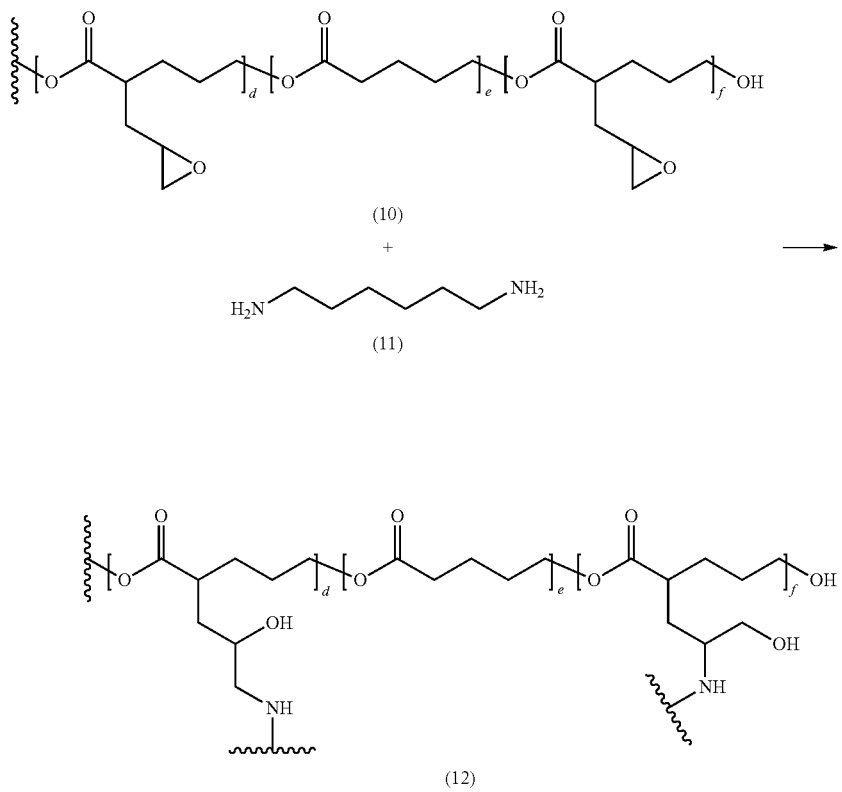

In some embodiments, the nucleophile can be a molecule wherein the nucleophilic site has an atom with an additional lone pair of atoms alpha to the nucleophilic atom (e.g., can be an "alpha effect" nucleophile). For example, the nucleophilic portion of the crosslinker can be a hydrazine, a peroxide, or a hydroxylamine.

In some embodiments, particles (e.g., microparticles) of the present disclosure can be crosslinked by a reaction between a tetrazine and a trans-cyclooctene. For example, crosslinking can take place as set forth in Scheme 5, below. One of skill in the art will understand that a variety of different regiochemistries is possible with a tetrazine-trans-cyclooctene reaction.

Scheme 5 - Exemplary Crosslinking Reaction Between trans-Cyclooctene and Tetrazine

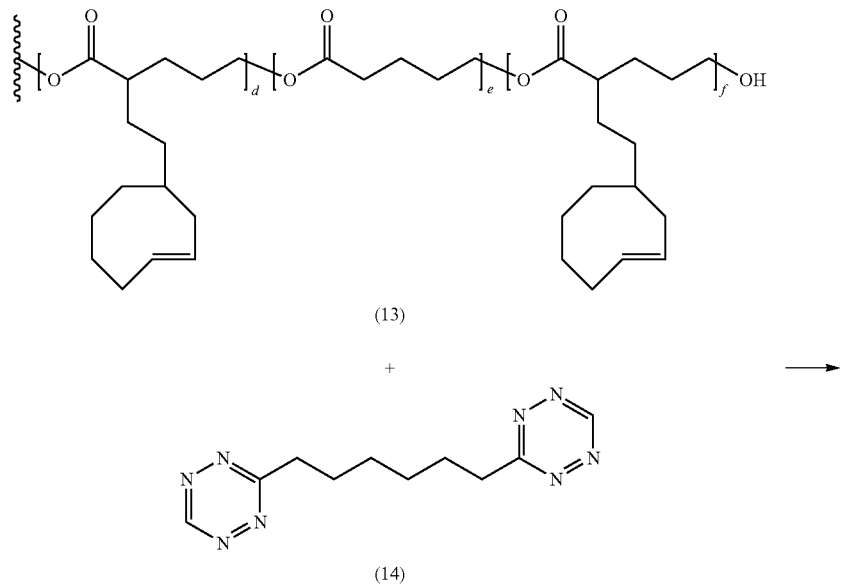

(13)

+

(14)

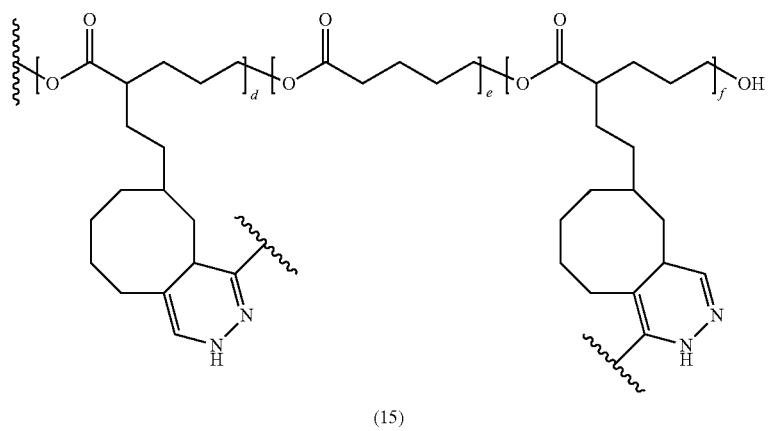

(15)

As set forth in Scheme 5, treatment of a trans-cyclooctene functionalized backbone (13) can be crosslinked with a ditetrazine (14). The tetrazine group can react with the trans-olefin of the cyclooctene group (e.g., a Diels-Alder cycloaddition followed by elimination of nitrogen gas). As set forth above in Scheme 5, the regiochemistry of tetrazine addition can vary. The flexibility in regiochemical crosslinking is also shown in Formula V. One of skill in the art will understand that Formula V shows that the crosslinking reaction is not limited to a specific regiochemistry (e.g., the trans-cyclooctene can be attached to the polymer backbone at different positions than the position shown).

In some embodiments, particles (e.g., microparticles) of the present disclosure can be crosslinked by a reaction between a thiol and a norbornene. For example, crosslinking can take place as set forth in Scheme 6, below. One of skill in the art will understand that a variety of different regiochemistries is possible with a thiol-norbornene reaction, and the present disclosure is not limited to a specific regiochemistry.

Scheme 6 - Possible Regiochemistries of Crosslinking Reaction of Norbornene with Thiol Groups

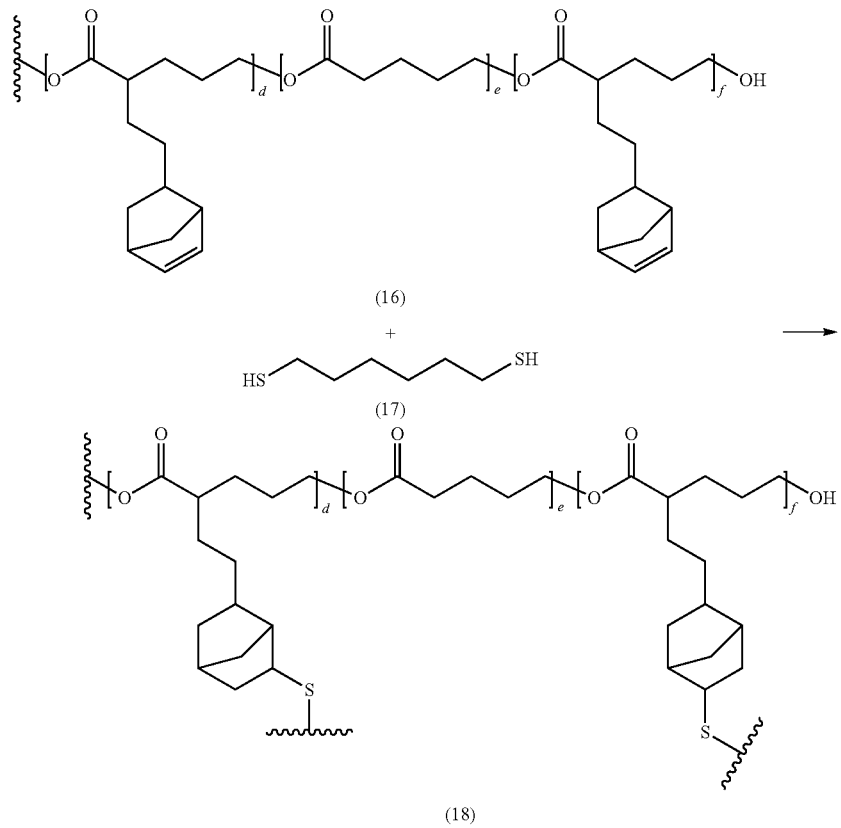

As set forth in Scheme 6, treatment of a norbornane-functionalized backbone (16) can be crosslinked with a dithiol (17) in the presence of ultraviolet light to form a crosslinked particle (18). In some embodiments, a photoinitiator can be added. The thiol group can react with the olefin of the norbornyl group to form sulfur-carbon bonds (e.g., by radical addition). As set forth above in Scheme 6, the regiochemistry of thiol addition can vary. The flexibility in regiochemical crosslinking is also shown in Formula VI. One of skill in the art will understand that Formula VI shows that the norbornyl group can be connected to the polymer backbone and crosslinked via a dithiol with a variety of different crosslinking regiochemistries, and the present disclosure is not limited to a specific regiochemistry.

One of skill in the art will understand that the above schemes are illustrative of the present invention and are not to be construed as limiting. For example, one of skill in the art will readily understand that any of the functional groups described above (e.g., norbornene groups, trans-cyclooctene groups, tetrazine groups) can be substituted without deviating from the spirit of the present disclosure. For example, any of the functional groups set forth above can have, for example, a methyl substituent.

One of skill in the art will understand that it is possible to switch the nature of the functional groups and crosslinkers disclosed herein to achieve similar results as disclosed herein. That is, one of skill in the art will understand that it is possible, for example, to employ functional groups disposed along the polyester backbone to crosslink with diolefins (e.g., 1,5-hexadiene) and achieve similar results.

In some embodiments, crosslinkers can have two functional groups (i.e., the crosslinkers can be linear and have a functional group at each end). Examples of such bifunctional crosslinkers are 1,6-hexanedithiol. In some embodiments, crosslinkers can be multifunctional (e.g., can have more than two functional groups). For example, a tetrafunctional crosslinker can have the structure of 4,4-bis(3-aminopropyl)heptane-1,7-diamine:

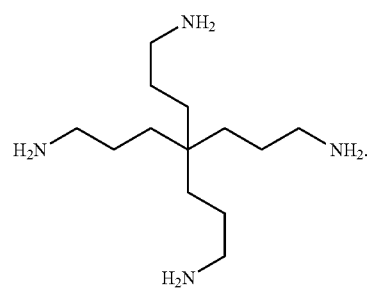 [SMILES: NCCCC(CCCN)(CCCN)CCCN]

One of skill in the art will understand that such a tetrafunctional crosslinker can be used, for instance, in the presence of epoxy-functionalized polymer backbones. Additionally, one of skill in the art will understand that the amine functionalities can be replaced with thiol groups to enable a tetrafunctional crosslinker in a thiol-ene reaction.

Additionally, one of skill in the art will understand that it is possible to use other chemical reactions (e.g., robust chemical reactions such as "click" reactions) to form crosslinks as described herein.

As used herein, crosslinkers of the present disclosure can comprise polymer (e.g., polyester, polycarbonate backbones). In other words, the crosslinker can comprise a polymer with functional groups disposed thereon that are capable of reacting with the functional groups of another polymer. For example, a polyester backbone comprising a plurality of allyl groups disposed thereon can be crosslinked by a polyester polymer comprising a plurality of free thiol groups disposed thereon. In some embodiments, the crosslinking polymer can comprise a plurality of monomer units (e.g., 100 or more, 200 or more, 300 or more, or 1000 or more monomer units). In some embodiments, the monomer units can be functionalized or unfunctionalized valerolactone units.

Size Control Techniques

The present disclosure provides for the preparation of particles of controllable size. In some embodiments, the particles can be microparticles or nanoparticles. For example, the particles described herein can have diameters between about 1 and 999 µm, including all ranges and subranges therebetween (e.g., between about 5 and about 500 µm; or about 10 µm; about 20 µm; about 50 µm; about 100 µm; or about 200 µm).

Size optimization or size control can be accomplished by a number of different methods described herein. For example, in some embodiments, the polymers and crosslinkers described herein can be dissolved in a non-aqueous (e.g., organic) solvent. The mixture of the polymers and crosslinkers (and, optionally, initiators or catalysts) can be emulsified with an aqueous phase (e.g., water optionally comprising an emulsifying agent such as polyvinylalcohol, PVA, or PEG). The emulsion parameters can be used to control the resulting particle size. That is, in some embodiments, the particle precursors (e.g., polymers, crosslinking agents and initiators) can be dissolved within droplets of the non-aqueous solvent of the emulsion. The crosslinking reaction can then take place while the particle precursors are dissolved in the non-aqueous solvent of the emulsion. In other words, the emulsion (i.e., the non-aqueous phase), can act as a mold or cast to allow uniformly dispersed microparticles. In some embodiments, the crosslinking can take place within the emulsion (i.e., the non-aqueous phase). For example, an emulsion comprising non-aqueous droplets with the particular precursors (e.g., polyester backbone and crosslinker) dissolved therein can be irradiated. In some embodiments, all of the components of the reaction are water-insoluble and therefore dissolve in the non-aqueous droplets of the emulsion.

Accordingly, in some embodiments, the size of the microparticles is a function of the size of the droplets (e.g., microdroplets) of the non-aqueous solvent. Thus, in some embodiments, the speed of stirring or agitation of the emulsion can be used to control the size of the non-aqueous droplets and thus the size of the resulting microparticles. In some embodiments, sonication (e.g., by probe tip or horn) can be used to control the size of the non-aqueous droplets and thus the size of the resulting microparticles.

Thus, in some embodiments, polymer precursors (e.g., PCL) can be added at high concentrations (e.g., greater than 50 mg/mL). In some embodiments, the speed of the emulsion process can be adjusted between about 10,000 rpm and 22,000 rpm. For example, the speed of the emulsion process can be about 10,000 rpm, about 11,000 rpm, about 12,000 rpm, about 13,000 rpm, about 14,000 rpm, about 15,000 rpm, about 16,000 rpm, about 17,000 rpm, about 18,000 rpm, about 19,000 rpm, about 20,000 rpm, about 21,000 rpm, or about 22,000 rpm. In some embodiments, the percentage of surfactant (e.g., polyvinyl alcohol, polyvinylpyrollidone or polyethylene glycol) in the aqueous phase can also be used to control the droplet size (and thus the size of the resulting particles). For example, the viscosity of the aqueous phase can be controlled by the amount of polyvinyl alcohol. In some embodiments, the percentage of polyvinyl alcohol can be between about 5% (wt) and about 20% (wt). For example, the percentage of polyvinyl alcohol can be about 5%, about 6%, about 7%, about 8%, about 9%, about 10%, about 11%, about 12%, about 13%, about 14%, about 15%, about 16%, about 17%, about 18%, about 19%, or about 20% by weight. Similarly, in some embodiments the molecular weight of the surfactant (e.g., polyvinyl alcohol, polyvinylpyrollidone or polyethylene glycol) can be used to control the droplet size (and thus the size of the resulting particles).

The ratio of aqueous solvent to non-aqueous solvent can also be used to control the size of the particles. For example, in some embodiments, between about 1 and 100 mL of aqueous solvent is used (e.g., about 1, about 5, about 10, or about 15 mL of aqueous solvent). In some embodiments, between about 1 and about 10 mL of non-aqueous solvent is used (e.g., about 1, about 2, about 3, about 4, about 5, about 6, about 7, about 8, about 9 or about 10 mL of non-aqueous solvent is used). In some embodiments, the ratio of aqueous to non-aqueous solvent is between about 1:1 to about 10:1.

After crosslinking the particles in the non-aqueous phase, the solvent (e.g., the non-aqueous solvent, the aqueous solvent, or both) can be removed. In some embodiments, removal of the solvent includes exposing the emulsion to a gas stream (e.g., an $N_2$ stream). The gas stream can last for a number of hours (e.g., about 1 hour, about 3 hours, about 6 hours, about 12 hours, or about 24 hours).

In another embodiment, the microparticles and macroparticles of the present disclosure can be controlled by photolithography. As set forth in Example 12, templates were formed by creating pegs of uniform size and shape which were used to create wells that are likewise of uniform size and shape. Polyesters and crosslinkers were dissolved in the wells and crosslinked to created microparticles and macroparticles of uniform size. The resulting particles can then be removed from the wells and used. In some embodiments, the molded solution can also contain a filler (e.g., a plasticizer). In some embodiments, the filler can be used to control the porosity of the resulting particles.

In another embodiment, the size of the particles (e.g., microparticles or nanoparticles) can be controlled by milling of a corresponding macroparticle. For example, in some embodiments, the crosslinking reactions of the present disclosure can be performed in a single phase (i.e., not an emulsion) to create a macroscopic particle (e.g, a particle with a mass of >10 mg). The resulting macroparticle can then be milled (e.g., crushed) to create a plurality of nanoparticles or microparticles.

Anti-Aggregation Techniques

In some embodiments, particles of the present disclosure can comprise PEG polymers attached to the polyester particle backbone. In some embodiments, the PEG polymers can be attached such that they are disposed toward the outside of the particle. For example, the PEG polymers can be attached at the terminal portion of the polyester particle backbones.

In some embodiments, attachment of PEG polymers can help to reduce aggregation of the particles of the present disclosure. In some embodiments, other polymers such as polyvinylpyrrolidone or pluronics can be used in place of PEG to help prevent aggregation. Also, attachment of PEG polymers can make the particles more hydrophilic and help facilitate drug loading. For example, a PVL-co-PAVL microparticle was prepared according to the methods disclosed herein. Without wishing to be bound by theory, the resulting particles were hydrophobic and demonstrated some aggregation. In some embodiments, it could be difficult to load drugs into the resulting particles because the particles were non-porous and hydrophobic.

In some embodiments, attachment of PEG polymers can be accomplished by using a hydroxy-PEG molecule as an initiator for a polymerization reaction (e.g., as an initiator for polyester formation). For example, a multi-arm PEG such as a PEG dendrimer or a six-arm, hydroxy terminated PEG can be used as a polymerization initiator.

Figure 18A:
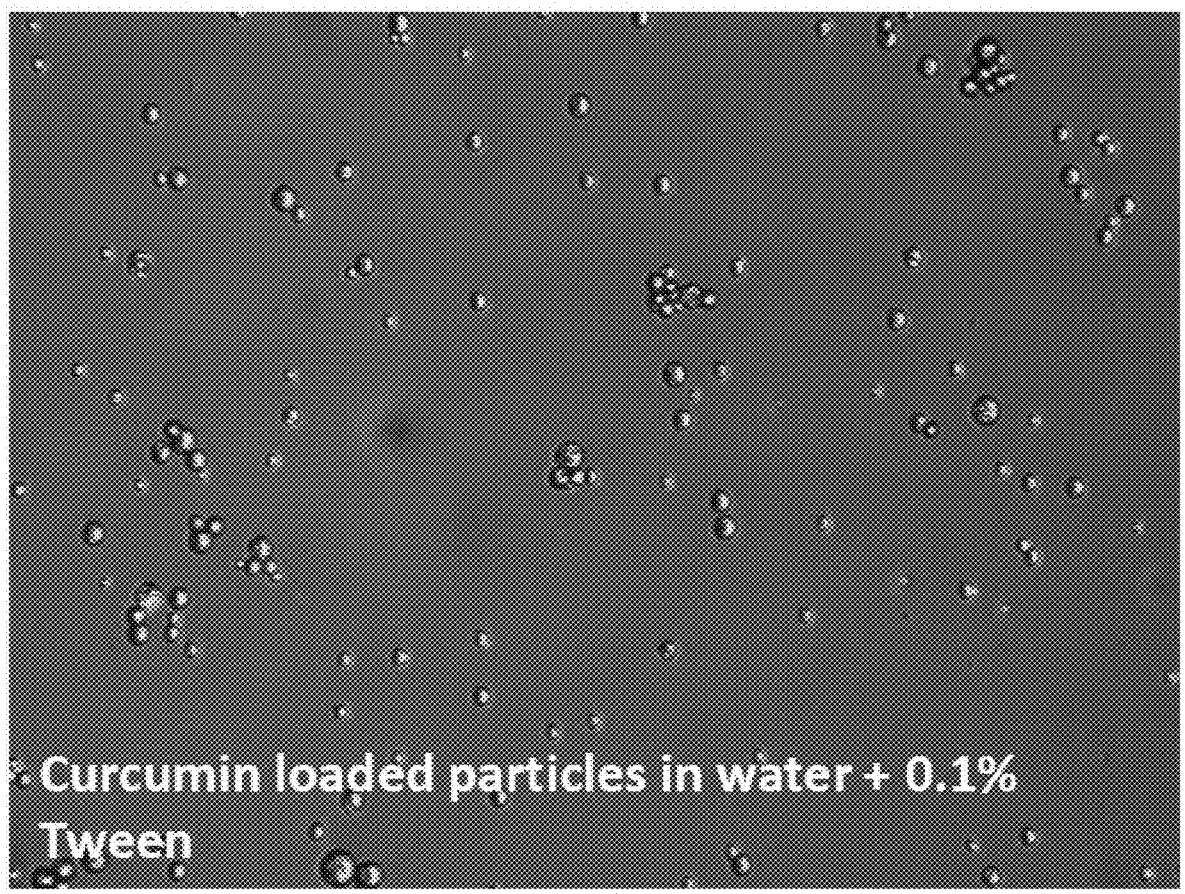
FIG. 18A shows curcumin-loaded particles dissolved in water containing 1% tween after being dried in THF with 25% PEG as a co-solvent.
Figure 18B:
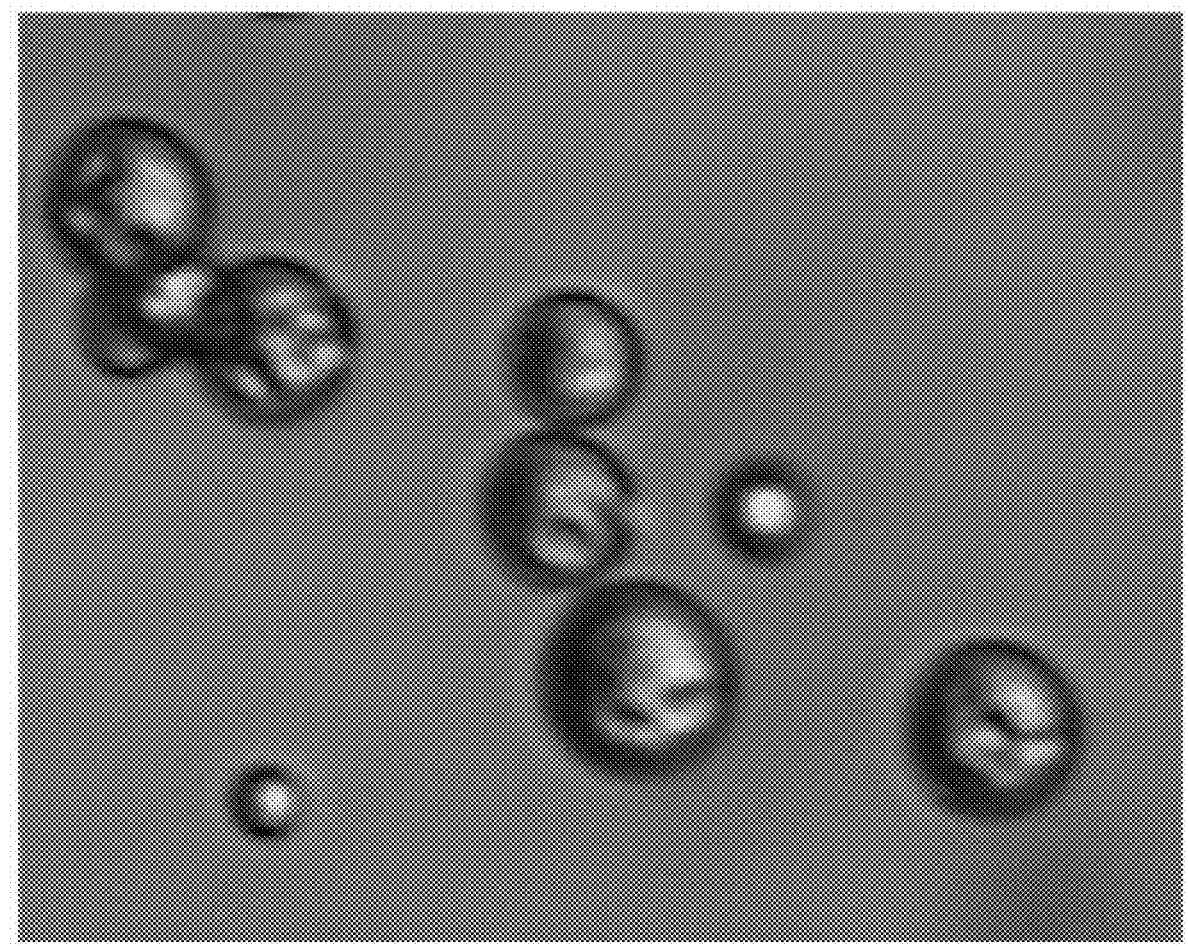
FIG. 18B shows a close-up view of curcumin-loaded particles dissolved in water containing 1% tween after being dried in THF with 25% PEG as a co-solvent.

In contrast, preparation of particles comprising mPEG-2K-PVL-co-PAVL (i.e., particles wherein PEG was disposed on the outside of the particle) demonstrated greater hydrophilicity, less aggregation, and easier drug loading. In some embodiments, at least about 2.5% PEG can be used (e.g., as a co-solvent) to reduce aggregation of drug particles (e.g., at least about 2.5%, at least about 5%, or at least about 10%). For example, FIG. 18A shows curcumin-loaded particles dissolved in water containing 1% tween after being dried in THF with 25% PEG as a co-solvent. Also, FIG. 18B shows a close-up view of curcumin-loaded particles dissolved in water containing 1% tween after being dried in THF with 25% PEG as a co-solvent. Without wishing to be bound by theory, the results suggest that dissolving in water comprising a surfactant can help reduce clumping of the particles.

Drug Loading and Release

In some embodiments, drugs can be loaded into the particles of the present disclosure by soaking the particles in a solvent (e.g., water, tetrahydrofuran (THF) or dimethylsulfoxide (DMSO)) that contains the drug. In some embodiments, the drug can be a small molecule, including, but not limited to, triamcinolone, triamcinolone hexacetonide, paclitaxel. Other drugs include, but are not limited to, bimatoprost, travaprost, brimonidine, camptothecin, tamoxifen, quercetin, thiostrepton, temozolamide, trametinib, seliciclib, fN'LFN'YK, GCGGGDHGVSSGV, hepatocyte growth factor (HGF), and bone morphogenetic protein 2 (BMP2).

Figure 13:
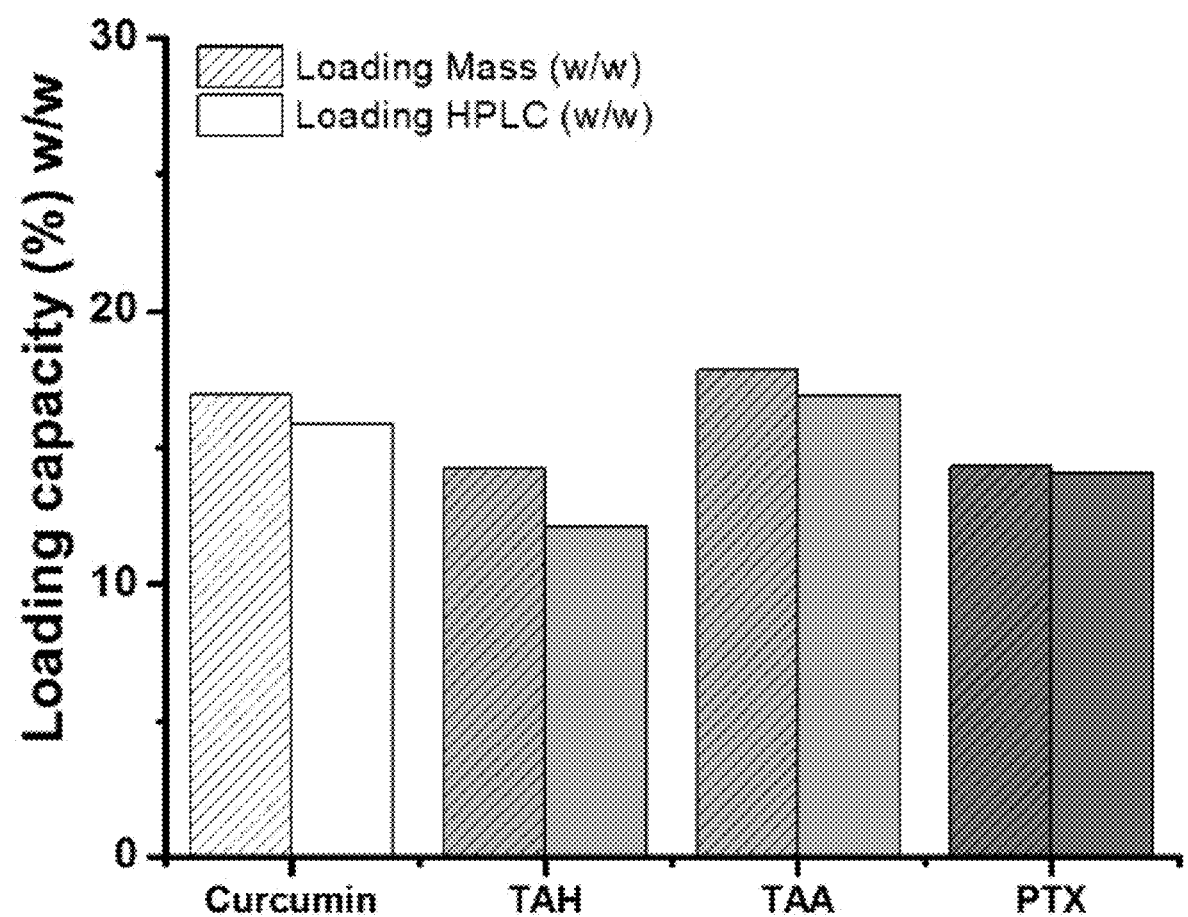
FIG. 13 shows the drug loading capacity of macroparticles, according to an embodiment of the disclosure.

In some embodiments, the drugs released from particles of the present disclosure can be hydrophobic. In some embodiments, particle loading with such hydrophobic drugs and subsequent release from the particles can facilitate the administration of such hydrophobic drugs (e.g., in vivo). FIG. 13 gives loading capacities of macroparticles of the present disclosure for the drugs curcumin (as a visible surrogate for a drug), paclitaxel, triamcinolone acetonide, and triamcinolone hexacetonide.

In some embodiments, the particles (e.g., microparticles such as 10 μm microparticles) can provide sustained release (e.g., about 3 months of sustained release of a drug (e.g., triamcinolone hexacetonide) in a relevant animal model.

Figure 4:
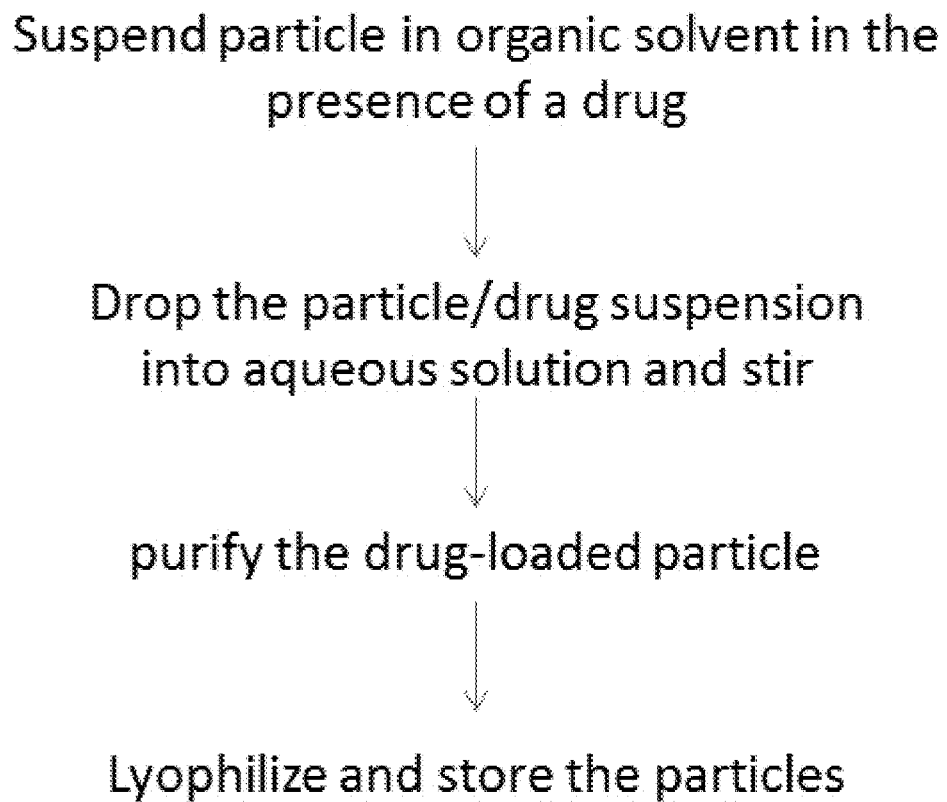
FIG. 4 shows a general schematic for loading drugs into particles of the present disclosure

FIG. 4 shows a schematic of the method for loading drugs into particles of the present disclosure. As set forth in FIG. 4, particles are suspended in an organic solvent containing a drug. The resulting mixture is stirred, and the drug can incorporate into the porous regions of the particles. After purification, the drugs can be lyophilized and stored until use.

In some embodiments, the loading procedure can affect the amount of drug that is absorbed into a particle of the present disclosure. For example, as set forth in Examples 7 and 8, 25 mg of 75:25 (mPEG-PVL-PAVL:PVL-PAVL) particles were swollen overnight with 2 mg/mL triamcinolone hexacetonide in THF. However, without wishing to be bound by theory, slow addition of greater volumes of water can facilitate greater uptake of triamcinolone hexacetonide by allowing the drug to preferentially partition into the particles. As set forth in Examples 7 and 8, slow addition of water enabled 67% loading efficiency. Additional parameters, in addition to the rate of water addition, that can affect the loading of a drug into a particle of the present disclosure are, for instance, the solvent in which the drug is dissolved, the time that the particles soak with the drug, and the volume of water used. Other parameters include the pH and the ionic strength of the solvent. For example, protic organic solvents such as methanol or ethanol can be used in place of water to facilitate loading of drug into a particle of the present disclosure.

Figure 5:
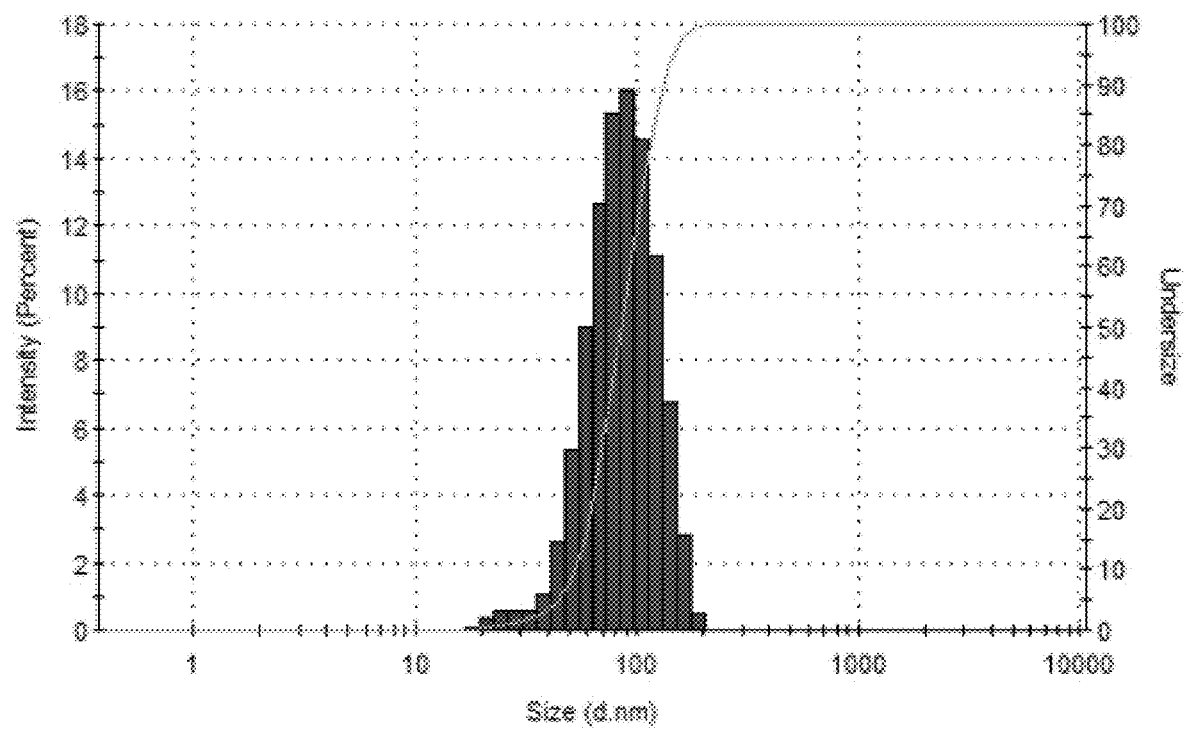
FIG. 5 shows a DLS plot of crosslinked mPEG-b-PVL-co-PAVL nanoparticles in water.

Without wishing to be bound by theory, soaking the particles of the present disclosure, (e.g., in THF, in the presence of a drug) can cause the particles to swell. For example, Example 5 shows that particles of the present disclosure can change in size (e.g., can swell) depending on the solvent in which they are placed. FIG. 5 shows a histogram of crosslinked mPEG-b-(PVL-coPAVL) microparticles demonstrating that had an average diameter of about 79 nm when placed in water. In some embodiments, the same particles swelled to a diameter of about 85 nm when soaked in dimethylsulfoxide (DMSO) as set forth in FIG. 6. The particles swelled to a diameter of about 208 nm when soaked in THF, as set forth in FIG. 7. In some embodiments, the difference in volume of a particle can range by a factor of 5-20. For example, a particle soaked in THF can be about 2× as large, about 3× as large, about 4× as large, about 5× as large, about 6× as large, about 7× as large, about 8× as large, about 9× as large, about 10× as large, about 11× as large, about 12× as large, about 13× as large, about 14× as large, about 15× as large, about 16× as large, about 17× as large, about 18× as large, about 19× as large, or about 20× as large, as a particle soaked in water. For comparison, FIG. 8 sets forth a histogram of non-crosslinked mPEG-b-PVL-co-PAVL microparticles after soaking in water.

Additionally, FIG. 9 sets forth the swelling of particles that have been suspended in THF. FIG. 9A shows a histogram and an image of microparticles after crosslinking. and FIG. 9B and FIG. 9C show histograms and images of microparticles after a DMSO washing step and an ethanol washing step, respectively. FIG. 9D shows images and a histogram of particles soaked in THF. As set forth in FIG. 9D, the THF-soaked particles can be larger than the particles soaked in other solvents such as water or ethanol.

The release of drugs from particles of the present disclosure can be dependent upon the crosslinking density of the particles. For example, high crosslinking density can lead to slower drug release as high crosslinking density can lead to slower hydrolysis and thus slower degradation of the particles.

The release of drugs from particles of the present disclosure can be dependent upon the density of the particles. For instance, in some embodiments increasing the length of the crosslinker can decrease the density of the particle and allow for faster release of drug from a given particle.

In some embodiments, the particles disclosed herein display low crystallinity. Without wishing to be bound by theory, the low crystallinity can be advantageous for diffusion-mediated release. FIGS. 28 and 29 shows that microparticles of the present disclosure have low crystallinity at high crosslinking density.

EXAMPLES

The disclosure is further illustrated by the following examples and synthesis examples, which are not to be construed as limiting this disclosure in scope or spirit to the specific procedures herein described. It is to be understood that the examples are provided to illustrate certain embodiments and that no limitation to the scope of the disclosure is intended thereby. It is to be further understood that resort may be had to various other embodiments, modifications, and equivalents thereof which may suggest themselves to those skilled in the art without departing from the spirit of the present disclosure and/or scope of the appended claims.

HPLC Methods

Unless otherwise indicated, quantitation of drug products was carried out using HPLC methods. Calibration curves for drugs used herein (e.g., triamcinolone, triamcinolone hexacetonide, triamcinolone acetonide, paclitaxel, and curcumin) were prepared by injecting known concentrations of the drugs and measuring the area under the curve at each concentration. Analyses were carried out using an Agilent Zorbax Eclipse XDB-C18 column (150×4.6 mm i.d.) with a 12.5×4.6 mm guard column. The parameters for each drug are given below in Table 1

TABLE 1

Calibration Parameters for Drug Concentrations

| Drug | Injection Volume | Retention time | Flow Rate | Detection wavelength | Mobile Phase | Cal. Slope | $R^2$ |
|---|---|---|---|---|---|---|---|
| Triamcinolone hexacetonide | 20 µL | 3 min | 1.2 mL/min | 240 nm | MeOH:$H_2O$ 90:10 | Y = 57.882x | 0.9999 |
| Paclitaxel | 20 µL | 7.8 min | 1 mL/min | 227 nm | MeOH:$H_2O$ 50:50 | Y = 73.156x | 0.9998 |
| Curcumin | 20 µL | 4.45 min | 1 mL/min | 420 nm | ACN:$H_2O$:AcOH 55:45:0.1 | Y = 338.71x | 0.9996 |

Example 1—Preparation of PVL-co-PAVL Copolymer

Figure 10A:
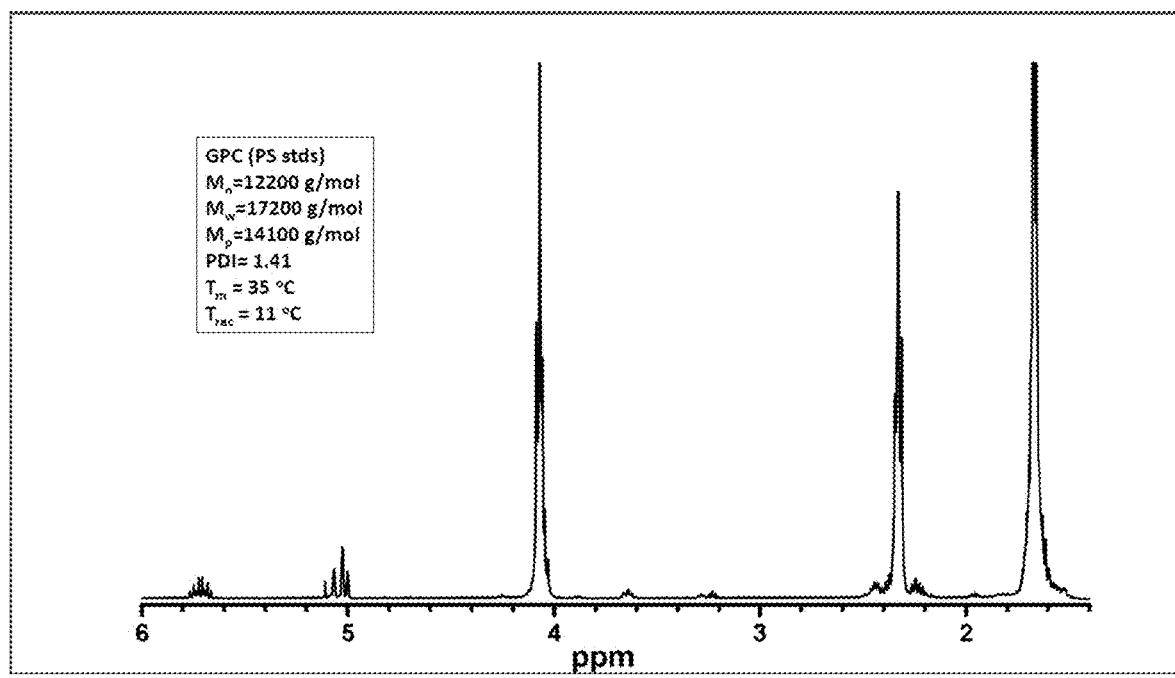
FIG. 10A shows a $^1$HNMR spectrum of PVL-co-PAVL polymer.
Figure 10B:
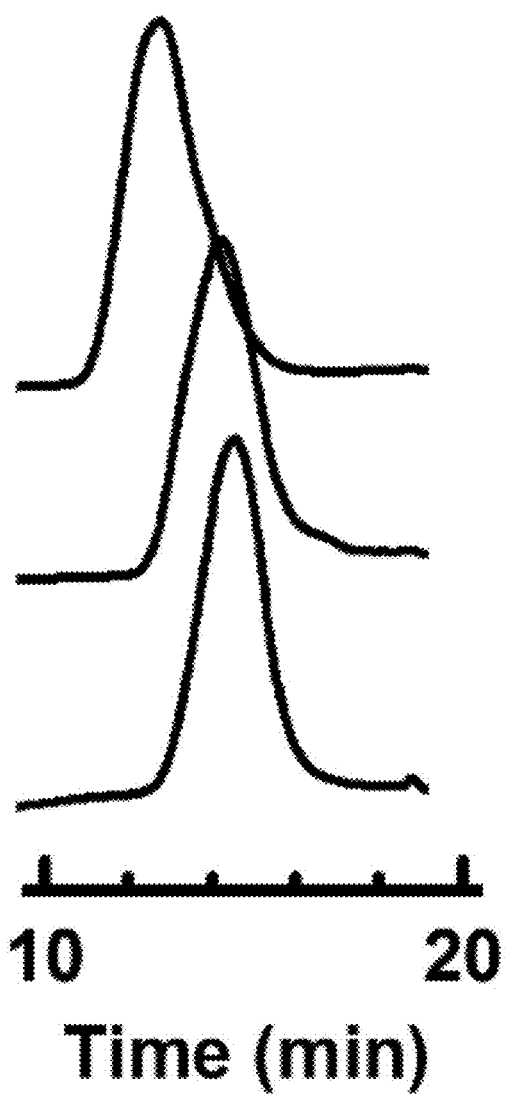
FIG. 10B shows a gel permeation chromatography plot of the PVL-co-PAVL polymer backbone comprising 6% PAVL, 10% PAVL, and 25% PAVL.

Benzyl alcohol (60 µl), valerolactone (8 mL) and allylvalerolactone (2 mL) were dissolved in toluene (20 mL) and triazabicyclodecene (catalyst) was added 2% mol:monomer and stirred at room temperature for 4 hours. FIG. 10 shows a $^1$HNMR spectrum of PVL-co-PAVL polymer with a molecular weight of 17200 g/mol (i.e., about 128 units of valerolactone and about 14 units of allylvalerolactone). The number average molecular weight of the polymer was about 12,200 g/mol, with a peak molecular weight of about 14100 g/mol. The polydispersity index was bout 1.41. The melting temperature was about 35° C. The temperature of recovery was about 11° C. FIG. 10B shows a gel permeation chromatography plot of the PVL-co-PAVL nanoparticles.

The mixture was subjected to gel permeation chromatography. The weight average molecular weight was about 17,200 g/mol.

Example 2—Preparation of Polyvalerolactone/Polyallyl Lactic Acid (PVL-co-PAL)

Allyl lactide is prepared according to the method disclosed in U.S. Pat. No. 8,758,828 to Markland, et. al. Benzyl alcohol, valerolactone and allyl lactide are dissolved in triazabicyclodecene and stirred at room temperature for 4 hours. The resulting polymer is isolated and used for crosslinking microparticles.

Example 3—Preparation of Crosslinked Microparticles Comprising Polycaprolactone and Polyallylvalerolactone Polycaprolactone homopolymer (PCL; 50 mg; 50 kDa; 1 mmol), polyvalerolactone (PVL; 50 mg) and polyallylvalerolactone (PAVL; 50 mg (6700 g/mol; 19% allylvalerolactone and 81% valerolactone)) and hexanedithiol (1 —SH group per alkene) were dissolved in 1 mL dichloromethane. 2,2-Dimethoxy-2-phenylacetophenone (DMPA; 3.4 mg; 0.2 equivalents per alkene) was added and the solution was added dropwise to 20 mL of water containing 5% polyvinyl alcohol. The mixture was homogenized with stirring (i.e., a Polytron® mechanical homogenizer at 22,000 rpm) for five minutes. The homogenized mixture was irradiated at 365 nm-4 mW under stirring for 30 minutes.

The mixture was stirred for 3 hours to allow the dichloromethane to evaporate. The mixture was then centrifuged at 4000 rpm at 10° C. for 10 minutes. The aqueous solution containing polyvinyl alcohol was poured off and the particles were rinsed with distilled water. The particles were then centrifuged and rinsed with water as above an additional three times.

The particles were then dispersed in DMSO and centrifuged at 4000 rpm at 20° C. for ten minutes. The DMSO was poured off and the process was repeated another two times. The resulting crosslinked particles were swollen and semi-transparent and did not dissolve in DMSO.

Figure 1B:
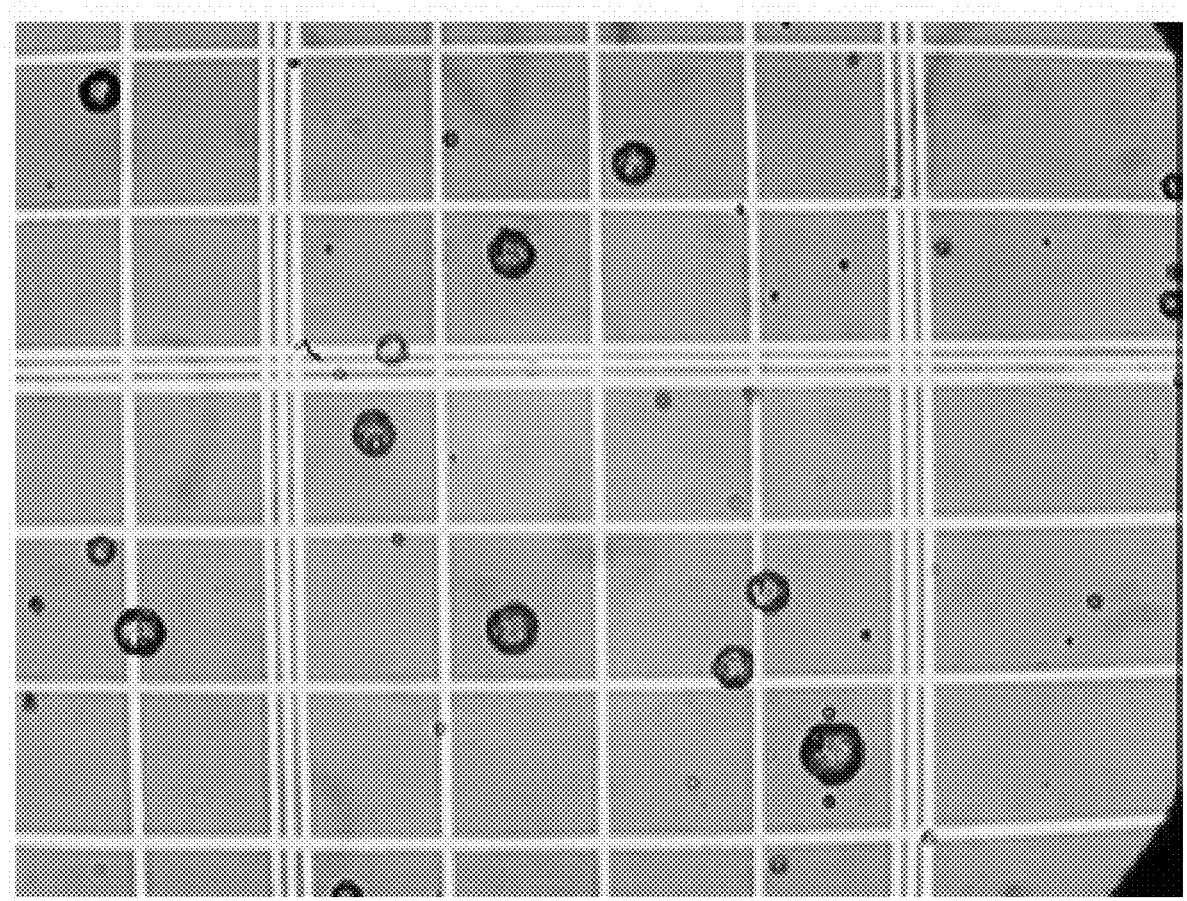
FIG. 1B shows photo of PCL, PVL-co-PAVL microparticles at a scale of about 400 μm.
Figure 1C:
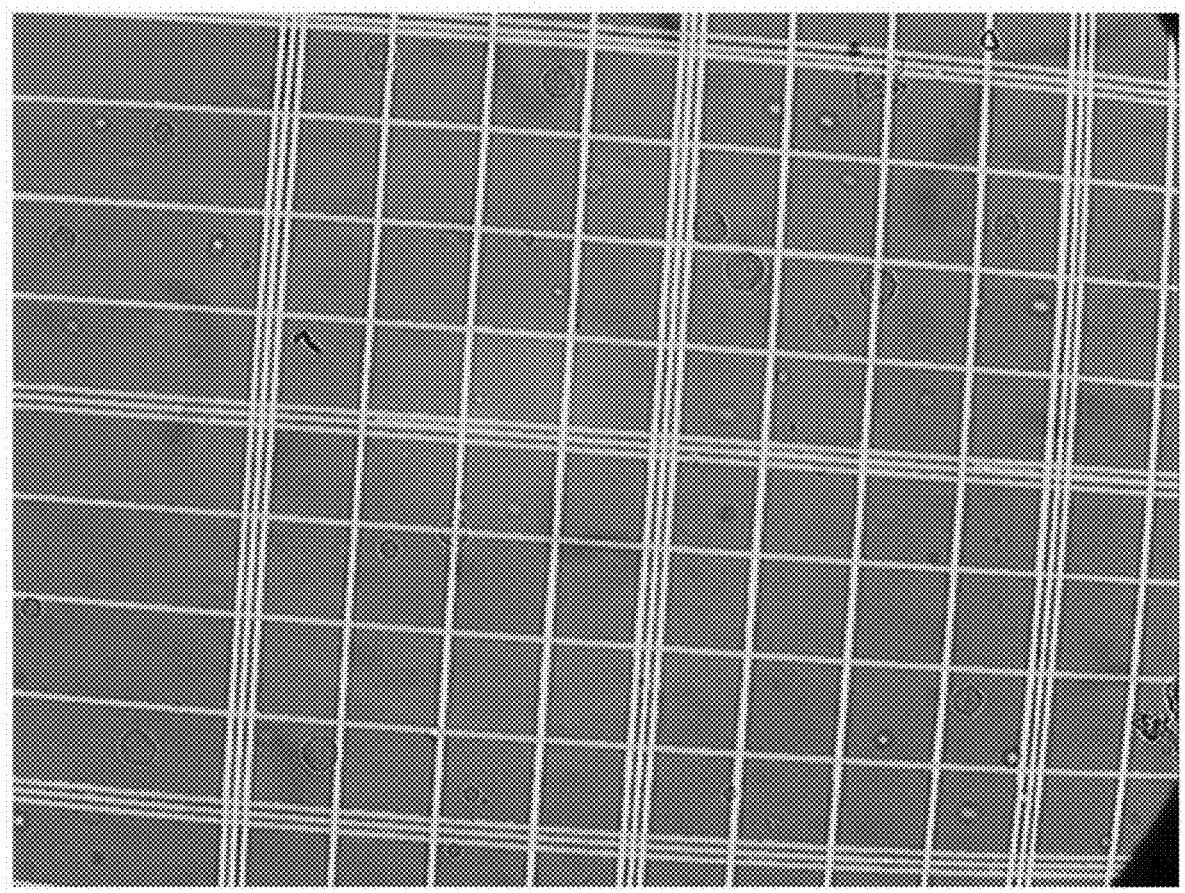
FIG. 1C shows a photo of PCL, PVL-co-PAVL microparticles at a scale of about 600 μm.
Figure 1D:
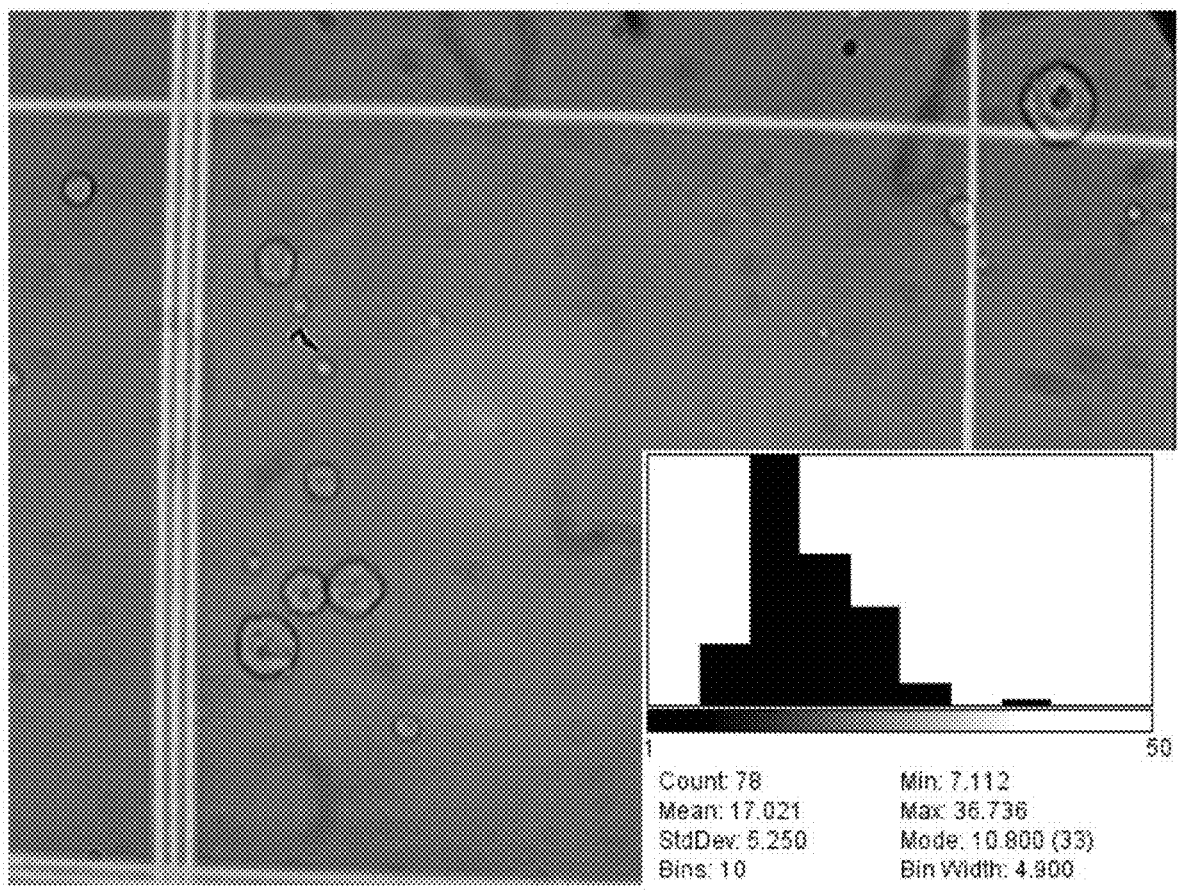
FIG. 1D shows a photo of PCL, PVL-co-PAVL microparticles at a scale of about 20 μm, along with a size distribution scheme.

FIG. 1A shows a photo of a PCL-co-PAVL copolymer at a scale of about 1500 µm produced by the above-method. FIGS. 1B, 1C, and 1D show photos of a PCL-co-PAVL/PVL copolymer produced by the above-method at a scale of 400 µm, 600 µm, and 20 µm, respectively. The particles comprised between 0.01% and 20% polyallylvalerolactone (PAVL), with the remainder comprising polycaprolactone (PCL) and polyvalerolactone (PVL).

Comparative Example 3—Attempted Preparation of Non-Crosslinked Microparticles Comprising Polycaprolactone and Polyallylvalerolactone Polycaprolactone homopolymer (PCL; 50 mg; 50 kDa; 1 mmol) and polyallylvalerolactone (PVL-co-PAVL; 50 mg) were dissolved in 1 mL dichloromethane. The solution was added dropwise to 20 mL of water containing 5% polyvinyl alcohol. The mixture was homogenized with stirring (i.e., a Polytron® mechanical homogenizer at 22,000 rpm) for five minutes. The homogenized mixture was irradiated at 365 nm-4 mW under stirring for 30 minutes. No crosslinker or DMPA was added.

The mixture was stirred for 3 hours to allow the dichloromethane to evaporate. The mixture was then centrifuged at 4000 rpm at 10° C. for 10 minutes. The aqueous solution containing polyvinyl alcohol was poured off and the particles were rinsed with distilled water. The particles were then centrifuged and rinsed with water as above an additional three times.

The mixture was then dispersed in DMSO and centrifuged at 4000 rpm at 20° C. for ten minutes. The DMSO was poured off and the process was repeated another two times. Although particles were formed, the particle precursors dissolved in DMSO and were not recovered. This example was performed as a control experiment and the results demonstrate that crosslinking is necessary to produce microparticles of the present disclosure.

Example 4—Preparation of Crosslinked Microparticles Comprising Polyallylvalerolactone Polyallylvalerolactone (PAVL; 100 mg (6700 g/mol; 19% allylvalerolactone and 81% valerolactone)) and hexanedithiol (1 —SH group per alkene) were dissolved in 1 mL dichloromethane. 2,2-Dimethoxy-2-phenylacetophenone (DMPA; 0.2 equivalents per alkene) was added and the solution was added dropwise to 20 mL of water containing 5% polyvinyl alcohol. The mixture was homogenized with stirring (i.e., a Polytron® mechanical homogenizer at 22,000 rpm) for five minutes. The homogenized mixture was irradiated at 365 nm-4 mW under stirring for 30 minutes.

The mixture was stirred for 3 hours to allow the dichloromethane to evaporate. The mixture was then centrifuged at 4000 rpm at 10° C. for 10 minutes. The aqueous solution containing polyvinyl alcohol was poured off and the particles were rinsed with distilled water. The particles were then centrifuged and rinsed with water as above an additional three times.

The particles were then dispersed in DMSO and centrifuged at 4000 rpm at 20° C. for ten minutes. The DMSO was poured off and the process was repeated another two times. The resulting crosslinked particles were swollen and semi-transparent and did not dissolve in DMSO.

Figure 2A:
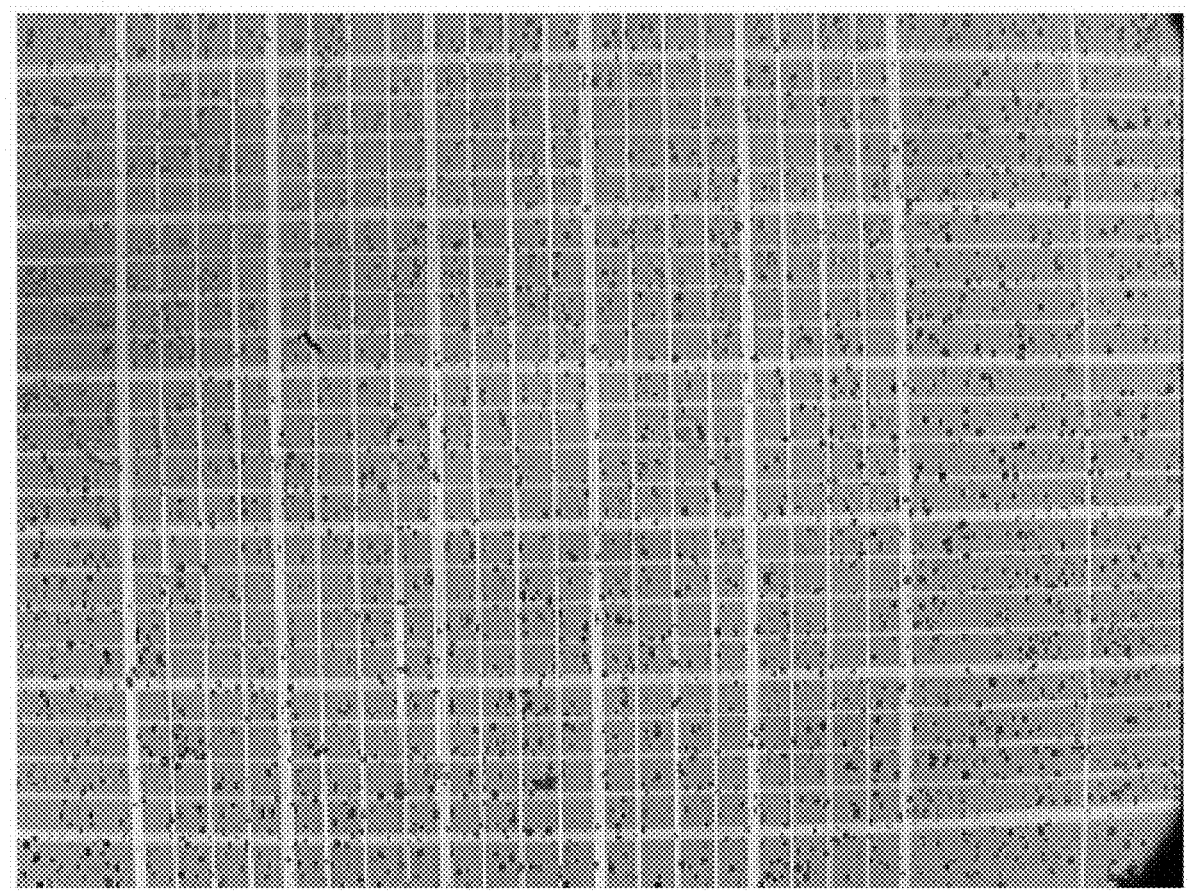
FIG. 2A shows a photo of PVL-co-PAVL microparticles at a scale of about 1500 μm.
Figure 2B:
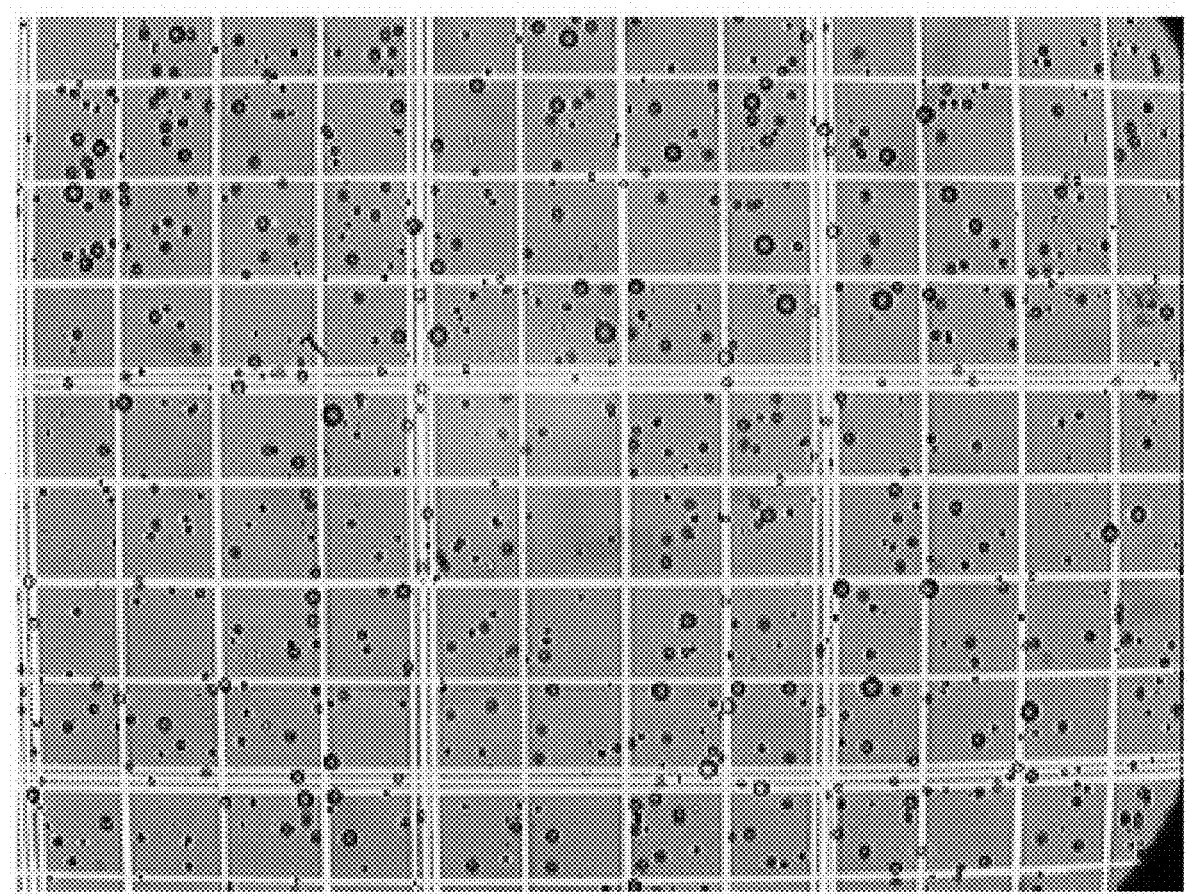
FIG. 2B shows photo of PVL-co-PAVL microparticles at a scale of about 400 μm.
Figure 2C:
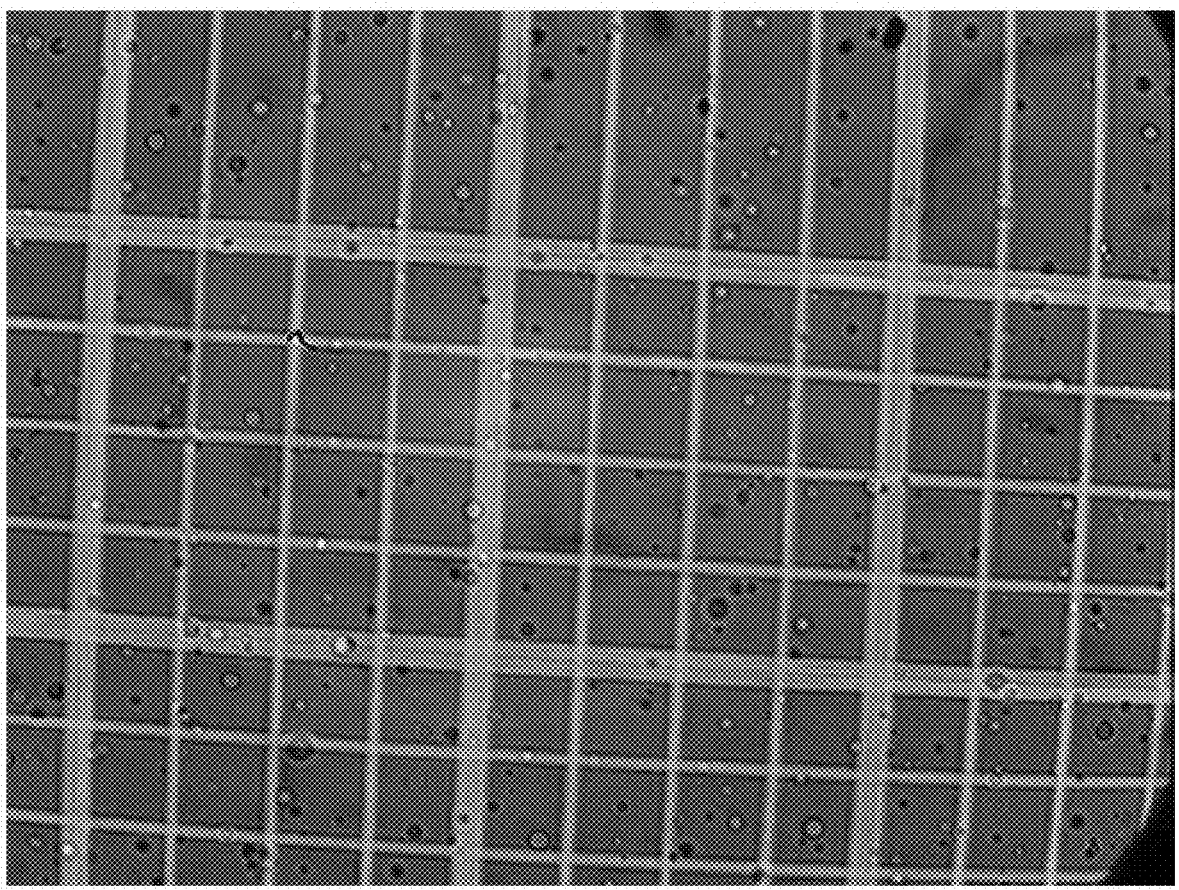
FIG. 2C shows a photo of PVL-co-PAVL microparticles at a scale of about 600 μm.
Figure 2D:
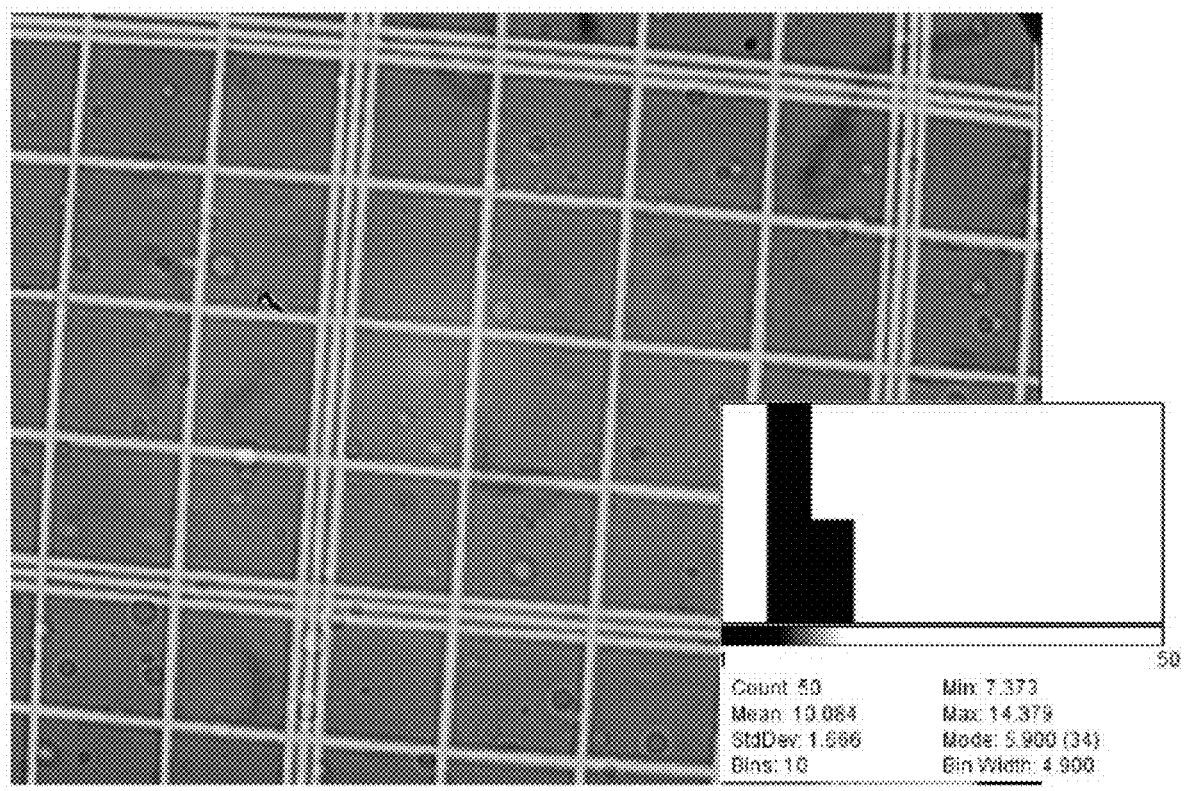
FIG. 2D shows a photo of PVL-co-PAVL microparticles at a scale of about 20 μm, along with a size distribution scheme.

FIG. 2A shows a photo of a PVL-co-PAVL copolymer at a scale of about 1500 μm produced by the above-method. FIGS. 2B, 2C, and 2D show photos of a PVL-co-PAVL copolymer produced by the above-method at a scale of 400 μm, 600 μm, and 20 μm, respectively.

Comparative Example 4—Attempted Preparation of Non-Crosslinked Microparticles Comprising Polyallylvalerolactone Polyallylvalerolactone (PAVL; 100 mg) was dissolved in 1 mL dichloromethane. The solution was added dropwise to 20 mL of water containing 5% polyvinyl alcohol. The mixture was homogenized with stirring (i.e., a Polytron® mechanical homogenizer at 22,000 rpm) for five minutes. No DMPA or crosslinker was added. The homogenized mixture was irradiated at 365 nm-4 mW under stirring for 30 minutes.

The mixture was stirred for 3 hours to allow the dichloromethane to evaporate. The mixture was then centrifuged at 4000 rpm at 10° C. for 10 minutes. The aqueous solution containing polyvinyl alcohol was poured off and the particles were rinsed with distilled water. The particles were then centrifuged and rinsed with water as above an additional three times.

The mixture was then dispersed in DMSO and centrifuged at 4000 rpm at 20° C. for ten minutes. The DMSO was poured off and the process was repeated another two times. Although particles were formed, the particle precursors dissolved in DMSO and were not recovered. This example was performed as a control experiment and the results demonstrate that crosslinking is necessary to produce microparticles of the present disclosure.

Example 5—Preparation of Crosslinked Microparticles Comprising Polyvalerolactone, Polyallylvalerolactone, and PEG 50 mg of mPEG-PVL-PAVL ($6.0 \times 10^{-5}$ mol allyl), 5 mg DMPA (0.25 eq/allyl) and 4.4 μL 1,6-hexanedithiol (0.5 eq/allyl) were dissolved in 3 mL THF. The polymer solution in THF was added dropwise with stirring to 10 mL deionized water in a 20-mL glass vial. The solvent was evaporated for about 18 hours and then the solution was irradiated with UV light (365 nm) for five minutes. The resulting microparticles were characterized via dynamic light scattering (DLS).

FIG. 5 shows a DLS plot of the crosslinked particles in water. As shown, the particles are about 100 nm in diameter. Table 2 below shows the results of the DLS analysis.

TABLE 2

DLS Analysis of Crosslinked mPEG-b-(PVL-coPAVL) Microparticles in Water

| Cumulant Results | | Distribution Results | | | |
|---|---|---|---|---|---|
| Z-average (nm) | 78.65 | Size (d) (nm) | | % Int | σ |
| Pd index | 0.140 | Peak 1 | 90.69 | 97.9 | 30.10 |
| Polydispersity (nm) | 29.4 | Peak 2 | 26.81 | 2.1 | 4.420 |
| % Polydispersity | 37.4 | Peak 3 | 0.000 | 0.0 | 0.000 |
| Derived kcps | 48,863.4 | | | | |

Figure 6:
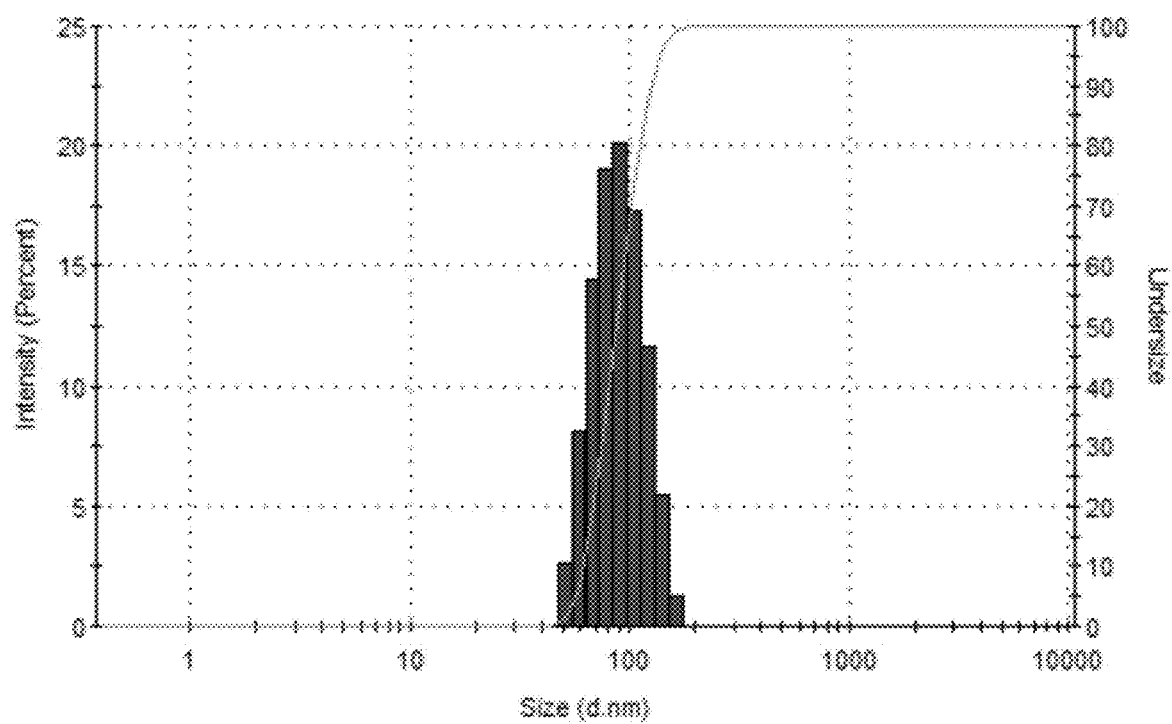
FIG. 6 shows a DLS plot of crosslinked mPEG-b-PVL-co-PAVL nanoparticles in dimethylsulfoxide (DMSO).

FIG. 6 shows a DLS plot of the crosslinked particles in DMSO. As shown, the particles are about 100 nm in diameter. Table 3 below shows the results of the DLS analysis.

TABLE 3

DLS Analysis of Crosslinked mPEG-b-(PVL-coPAVL) Microparticles in DMSO

| Cumulant Results | | Distribution Results | | | |
|---|---|---|---|---|---|
| Z-average (nm) | 85.22 | Size (d) (nm) | | % Int | σ |
| Pd index | 0.077 | Peak 1 | 91.61 | 100.0 | 24.28 |
| Polydispersity (nm) | 23.6 | Peak 2 | 0.000 | 0.0 | 0.000 |
| % Polydispersity | 27.7 | Peak 3 | 0.000 | 0.0 | 0.000 |
| Derived kcps | 3,424.2 | | | | |

Figure 7:
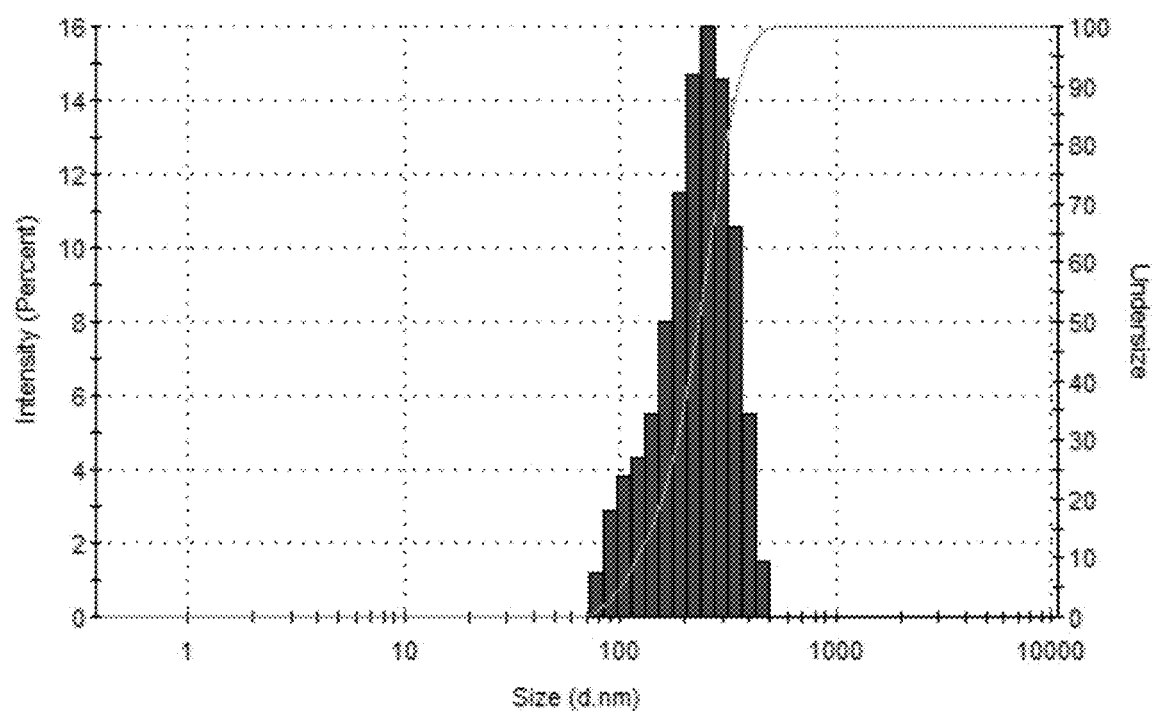
FIG. 7 shows a DLS plot of crosslinked mPEG-b-PVL-co-PAVL nanoparticles in THF.

FIG. 7 shows a DLS plot of the crosslinked particles in THF. As shown, the particles are between about 100 nm and 1000 nm in diameter. Table 4 below shows the results of the DLS analysis.

TABLE 4

DLS Analysis of Crosslinked mPEG-b-(PVL-coPAVL) Microparticles in THF

| Cumulant Results | | Distribution Results | | | | |
|---|---|---|---|---|---|---|
| Z-average (nm) | 208.4 | Size (d) (nm) | % Int | σ | % P | d |
| Pd index | 0.171 | Peak 1 | 236.4 | 100.0 | 84.76 | 35.9 |
| Polydispersity (nm) | 86.1 | Peak 2 | 0.000 | 0.0 | 0.000 | 0 |
| % Polydispersity | 41.3 | Peak 3 | 0.000 | 0.0 | 0.000 | 0 |
| Derived kcps | 19181.1 | | | | | |

Figure 11A:
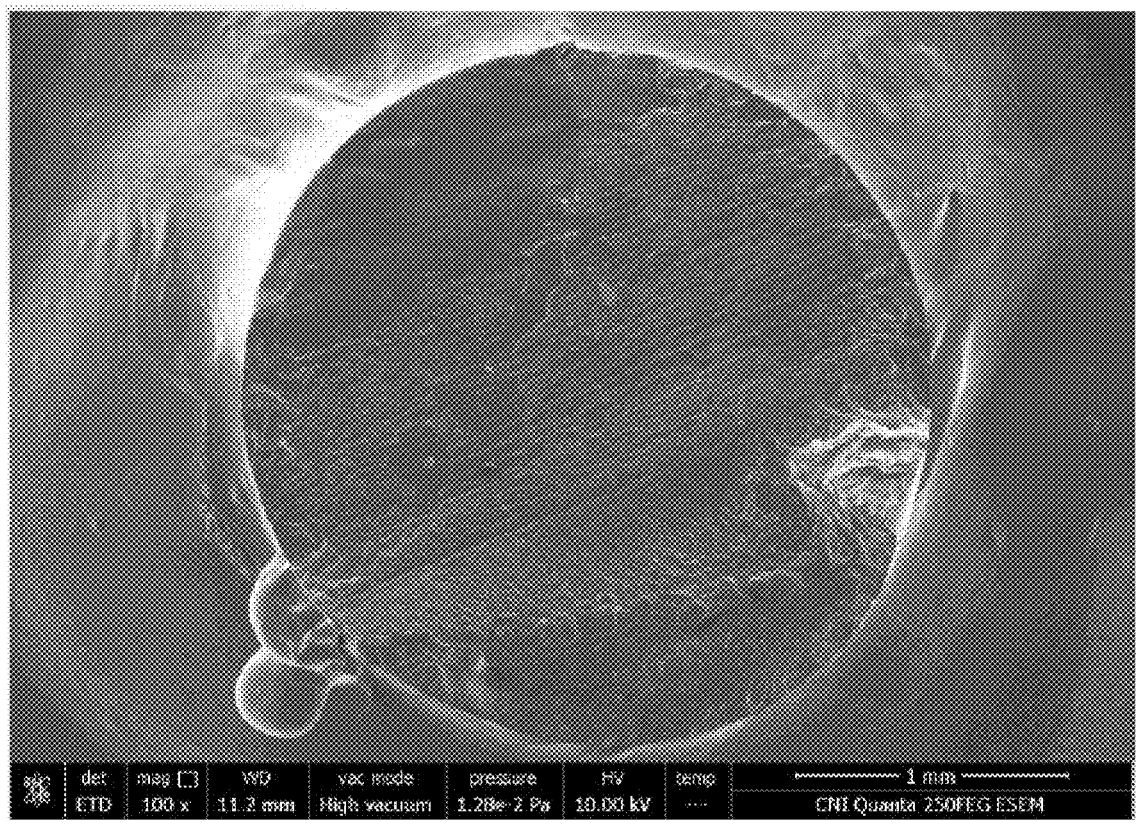
FIG. 11A shows a microscope image of mPEG-b-PVL-co-PAVL macroparticles (80:20) at a resolution of about 1 mm.

FIG. 11A shows a microscope image of mPEG-b-PAVL-co-PVL macroparticles (80:20) produced by this method at a resolution of about 1 mm.

Figure 11B:
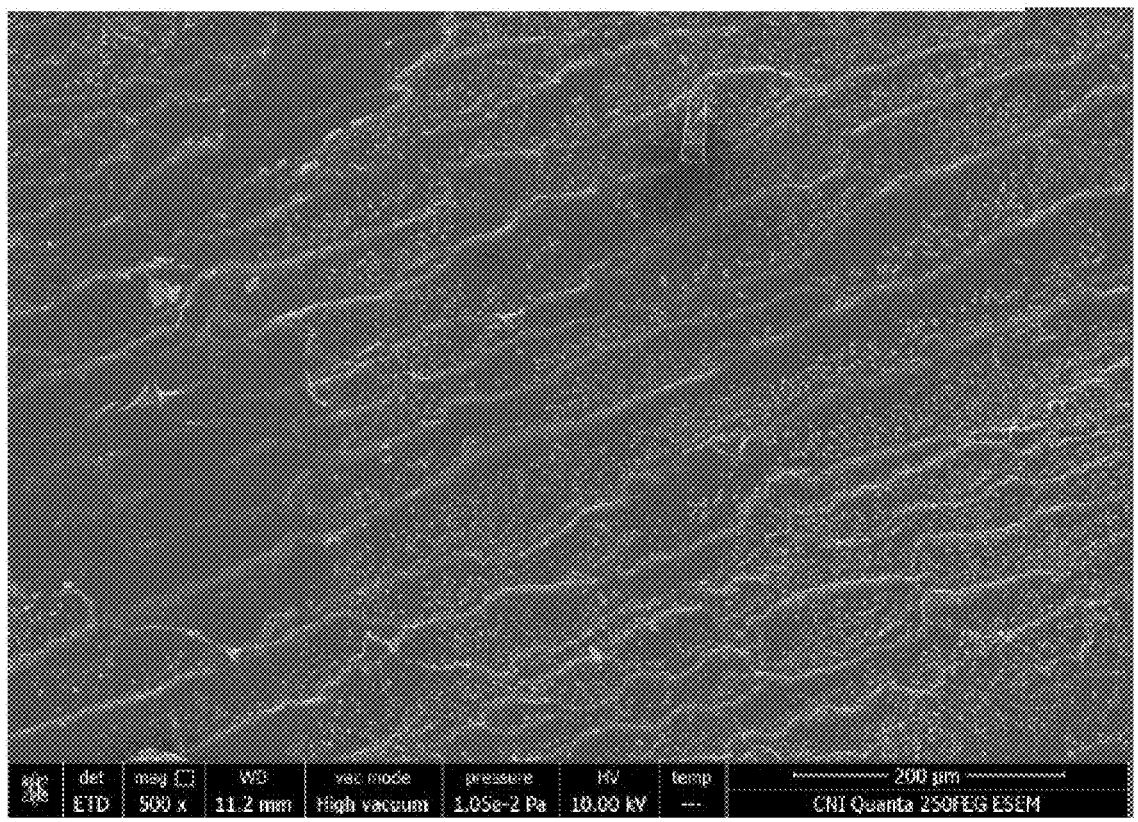
FIG. 11B shows a microscope image of mPEG-b-PVL-co-PAVL macroparticles (80:20) at a resolution of about 200 μm.

FIG. 11B shows a microscope image of mPEG-b-PAVL-co-PVL macroparticles (80:20) produced by this method at a resolution of about 200 μm.

Figure 11C:
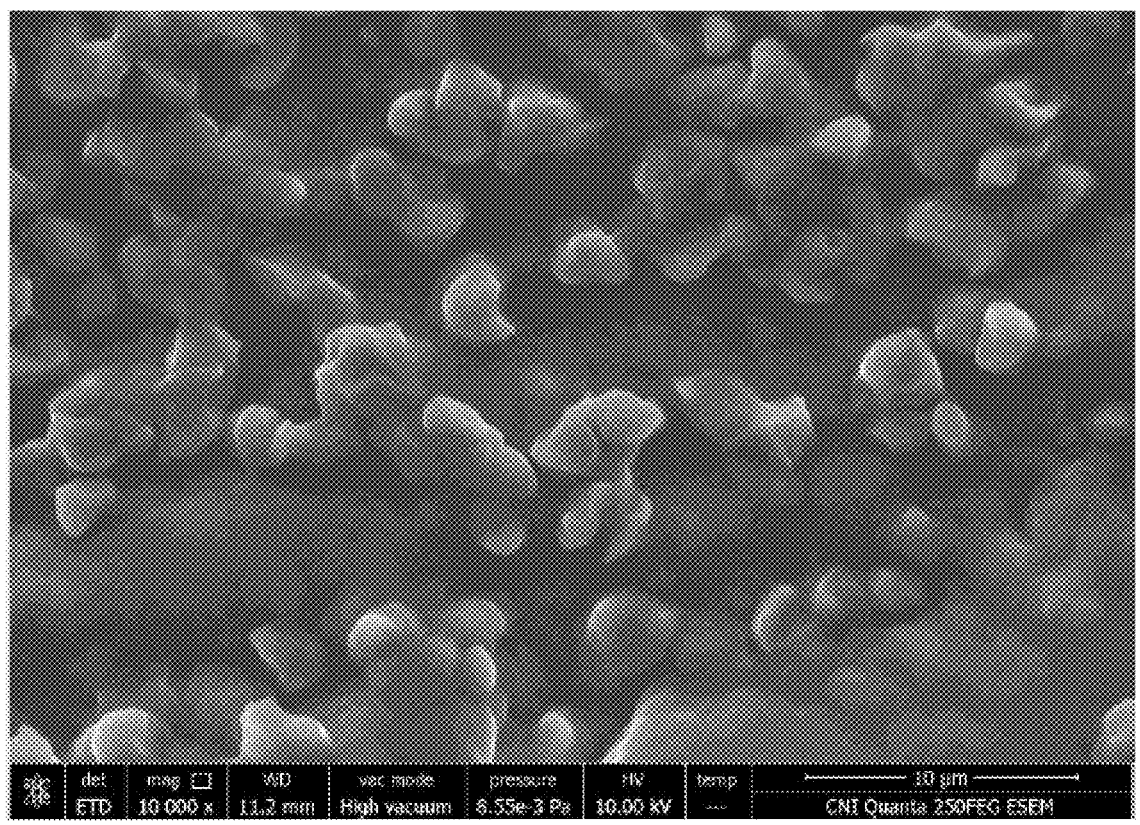
FIG. 11C shows a first microscope image of mPEG-b-PVL-co-PAVL macroparticles (80:20) at a resolution of about 10 µm.

FIG. 11C shows a first microscope image of mPEG-b-PAVL-co-PVL macroparticles (80:20) produced by this method at a resolution of about 10 μm.

Figure 11D:
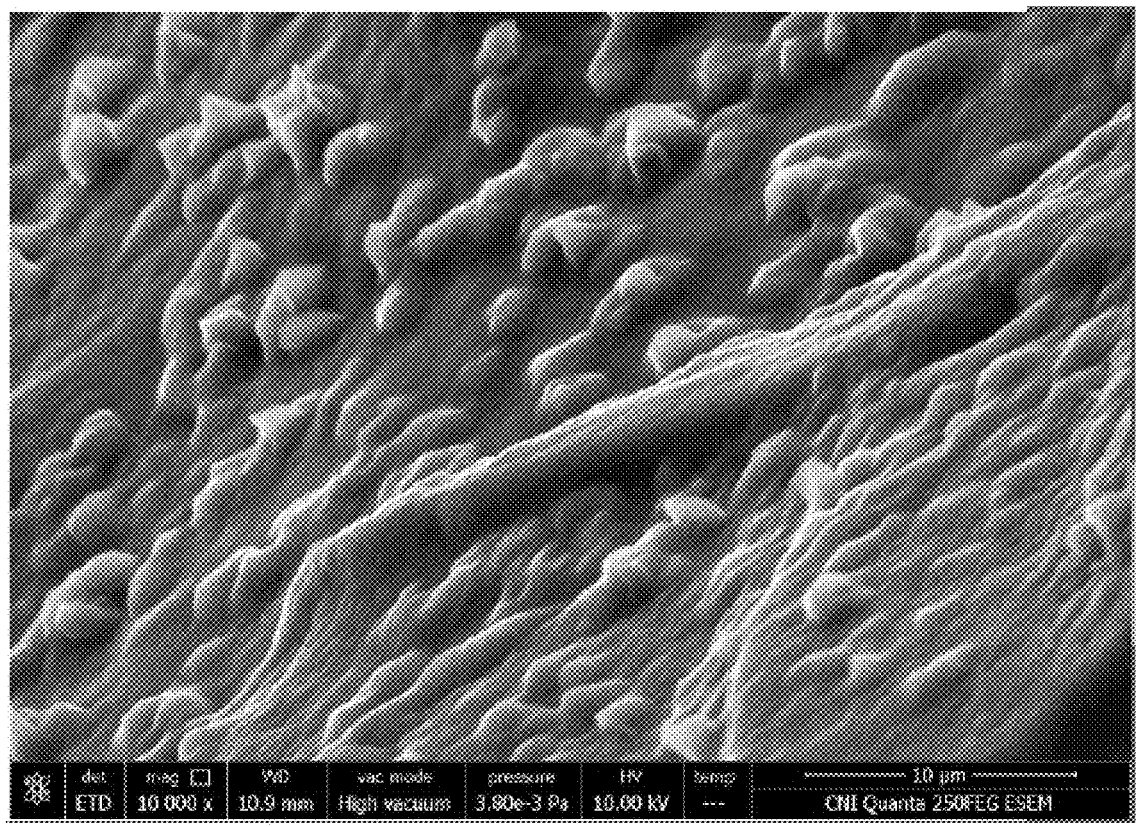
FIG. 11D shows a second microscope image of mPEG-b-PVL-co-PAVL macroparticles (80:20) at a resolution of about 10 µm.

FIG. 11D shows a second microscope image of mPEG-b-PAVL-co-PVL macroparticles (80:20) produced by this method at a resolution of about 10 μm.

Example 6—Preparation of Non-Crosslinked Nanoparticles Comprising Polyvalerolactone, Polyallylvalerolactone, and PEG 50 mg of mPEG-PVL-PAVL (6.0×10$^{-5}$ mol allyl) and 4.4 μL 1,6-hexanedithiol (0.5 eq/allyl) were dissolved in 3 mL THF. The polymer solution in THF was added dropwise with stirring to 10 mL deionized water in a 20-mL glass vial. No photoinitiator was added, and the emulsion was irradiated with UV light (365 nm) for five minutes as a control measure. The solvent was evaporated for about 18 hours, and the resulting micelles were characterized via dynamic light scattering.

Figure 8:
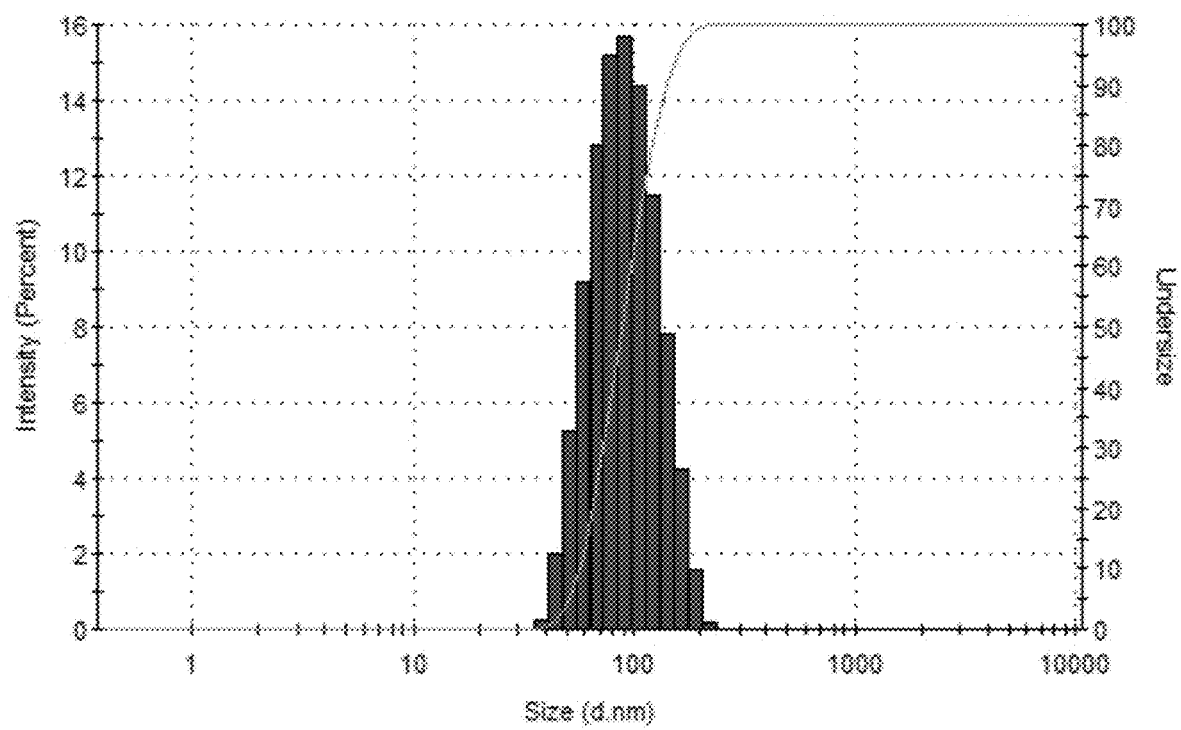
FIG. 8 shows a DLS plot of non-crosslinked mPEG-b-PVL-co-PAVL nanoparticles in water.
Figure 12:
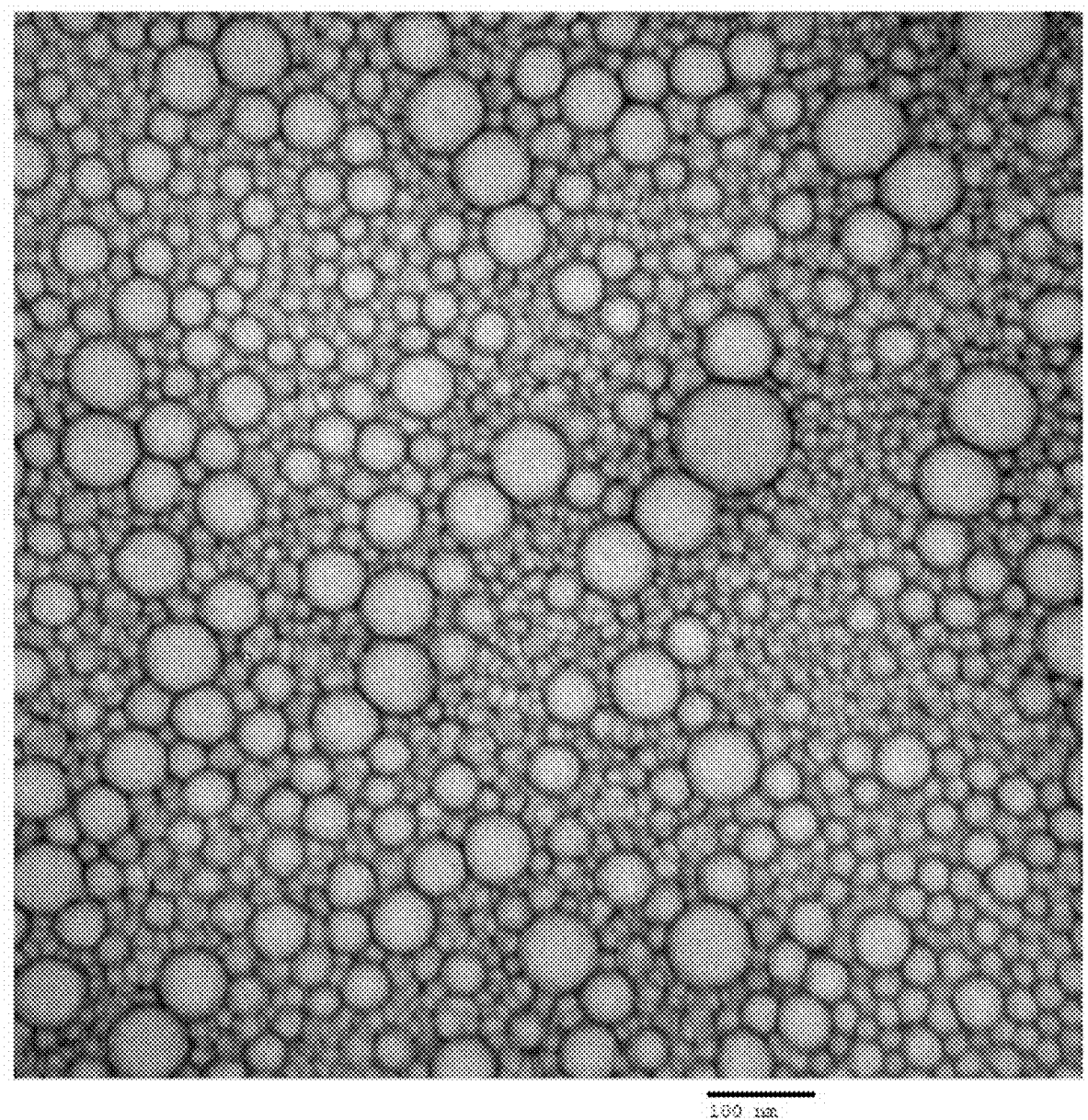
FIG. 12 shows a microscope micrograph of non-crosslinked microparticles in water.

FIG. 8 shows a DLS image of non-crosslinked microparticles produced as in the method above in water, and FIG. 12 shows a DLS plot of non-crosslinked particles in water. As shown, the particles are about 100 nm in diameter. Table 5 below shows the results of the DLS analysis. Without wishing to be bound by theory, because the particles were not crosslinked, they re-dissolved in organic solvent.

TABLE 5

DLS Analysis of Non-Crosslinked mPEG-b-(PVL-coPAVL) Microparticles in Water

| Cumulant Results | | Distribution Results | | | |
|---|---|---|---|---|---|
| Z-average (nm) | 80.89 | Size (d) (nm) | % Int | σ | |
| Pd index | 0.173 | Peak 1 | 94.69 | 100.0 | 32.66 |
| Polydispersity (nm) | 33.6 | Peak 2 | 0.000 | 0.0 | 0.000 |
| % Polydispersity | 41.6 | Peak 3 | 0.000 | 0.0 | 0.000 |
| Derived kcps | 44486.7 | | | | |

Example 7—Loading of Microparticles with Triamcinolone Hexacetonide 25 mg of 75:25 (mPEG-PVL-PAVL:PVL-PAVL) particles were swollen overnight with 2 mg/mL triamcinolone hexacetonide in THF. 10 mL water including 0.1% tween was then added dropwise. The resulting mixture was centrifuged, the supernatant was collected, and the addition of 10 mL water including 0.1% tween was added dropwise again (2×; 30 mL total).

After the first centrifugation, it was observed that the particles did not easily resuspended in 10 mL water containing 0.1% tween. Without wishing to be bound by theory, this may be due to the fact that the triamcinolone hexacetonide crystallized on the surface of the particles. Without wishing to be bound by theory, this may be due to the relatively fast addition of water and the limited solubility of triamcinolone hexacetonide, which caused it to crystallize. Also without wishing to be bound by theory, the release profile showed relatively rapid release from the particles, likely a result of the surface-crystallized drug re-dissolving in solution.

Example 8—Loading of Particles with Triamcinolone Hexacetonide with Slow Addition of Water 15-mg macroparticles were placed in 0.5 mL of THF containing 15 mg of drug. After 2 hours of swelling, the cylinders were washed with fresh THF and dried at room temperature for 24 hours.

40 mg of microparticles were swollen in 0.5 mL of tetrahydrofuran containing 10 mg of drug. Slow addition of water was used in some embodiments for the addition to microparticles.

The loading efficiency, which included surface-bound drug or free drug in solution, was 67%. Upon suspending the particles in dissolution media, 20% of the triamcinolone hexacetonide was released within an hour, and 30% was released within 2 hours.

Without wishing to be bound by theory, very slow addition of larger volumes of water can give triamcinolone hexacetonide the opportunity to preferentially partition into the macroparticles. Accordingly, FIG. 13 shows the loading capacity of the 15-mg macroparticles of the present disclosure with curcumin (CCM), triamcinolone hexacetonide (TAH), triamcinolone acetonide (TAA), and paclitaxel (PTX).

Figure 14:
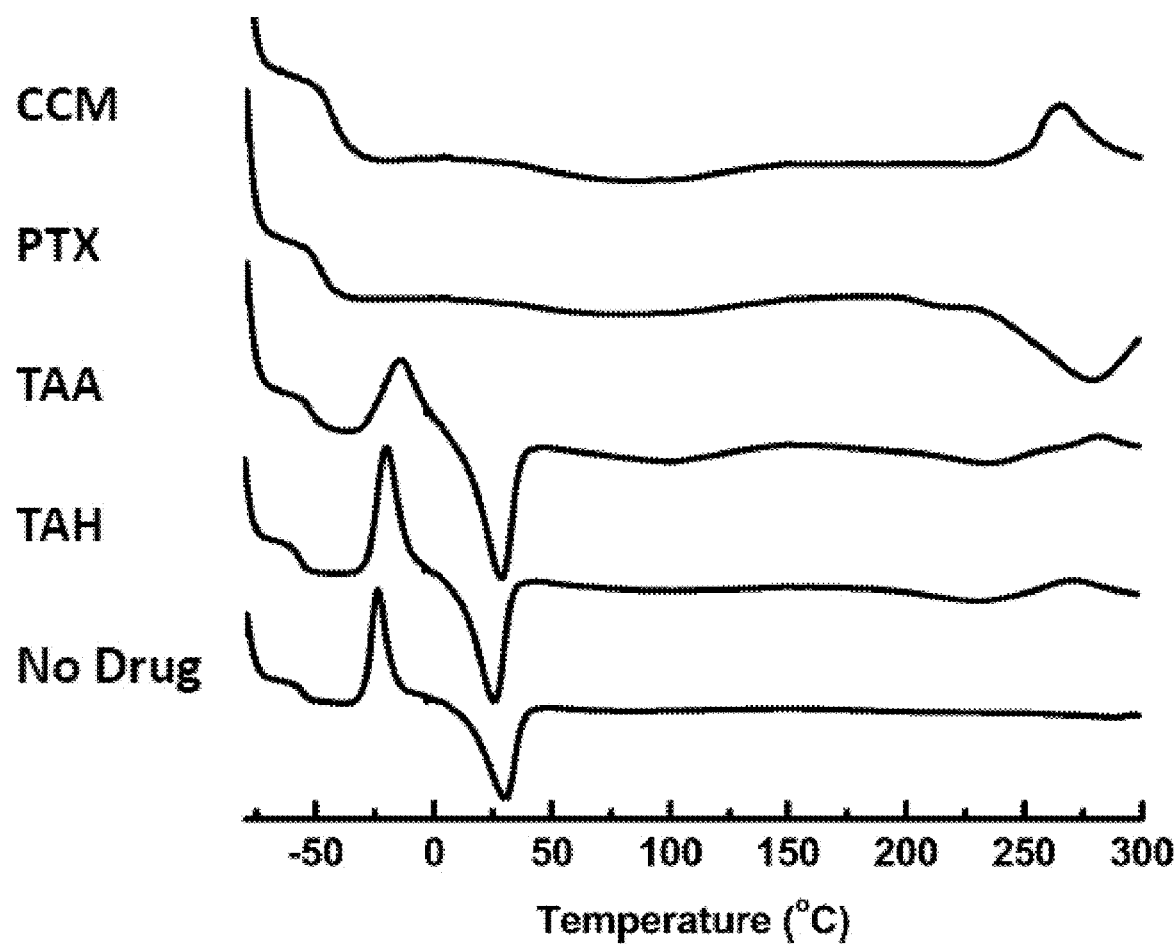
FIG. 14 shows a DSC plot of microparticles loaded with curcumin, paclitaxel, triamcinolone acetonide, triamcinolone hexacetonide, and without drug.
Figure 15:
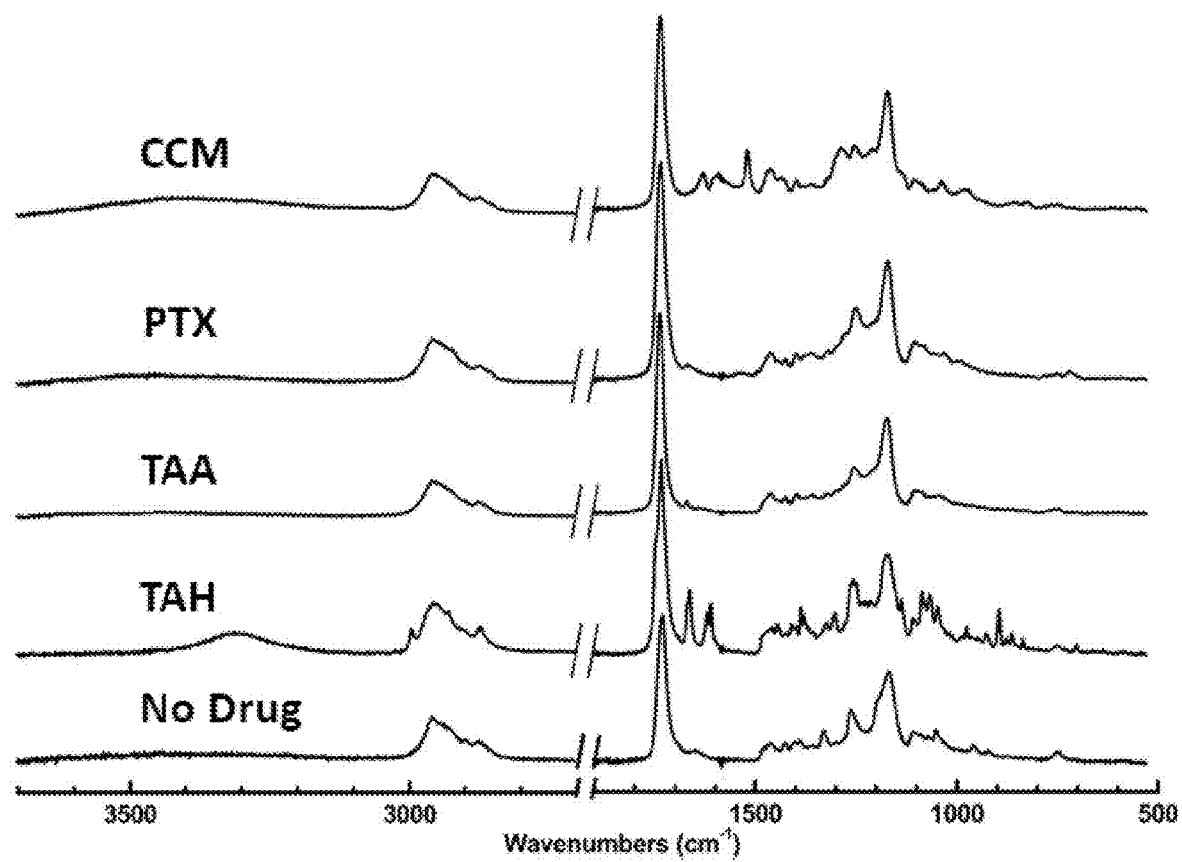
FIG. 15 shows FTIR spectra of microparticles of the present disclosure loaded with curcumin, paclitaxel, triamcinolone acetonide, triamcinolone hexacetonide, and without drug.

FIG. 14 shows differential scanning calorimetry plots of macroparticles loaded with curcumin (CCM), triamcinolone hexacetonide (TAH), triamcinolone acetonide (TAA), and paclitaxel (PTX) and without drugs. FIG. 15 shows FTIR spectra of microparticles loaded with curcumin (CCM), triamcinolone hexacetonide (TAH), triamcinolone acetonide (TAA), and paclitaxel (PTX) and without drugs.

Example 9—Formation of Microparticle Flakes

Crosslinked microparticles (15 mg) were loaded with 2.5 mg curcumin by overnight soaking in THF followed by the slow addition of 50 mL PBS containing 0.1% Tween. The microparticles were rinsed with THF to remove free curcumin and dried overnight.

Figure 16:
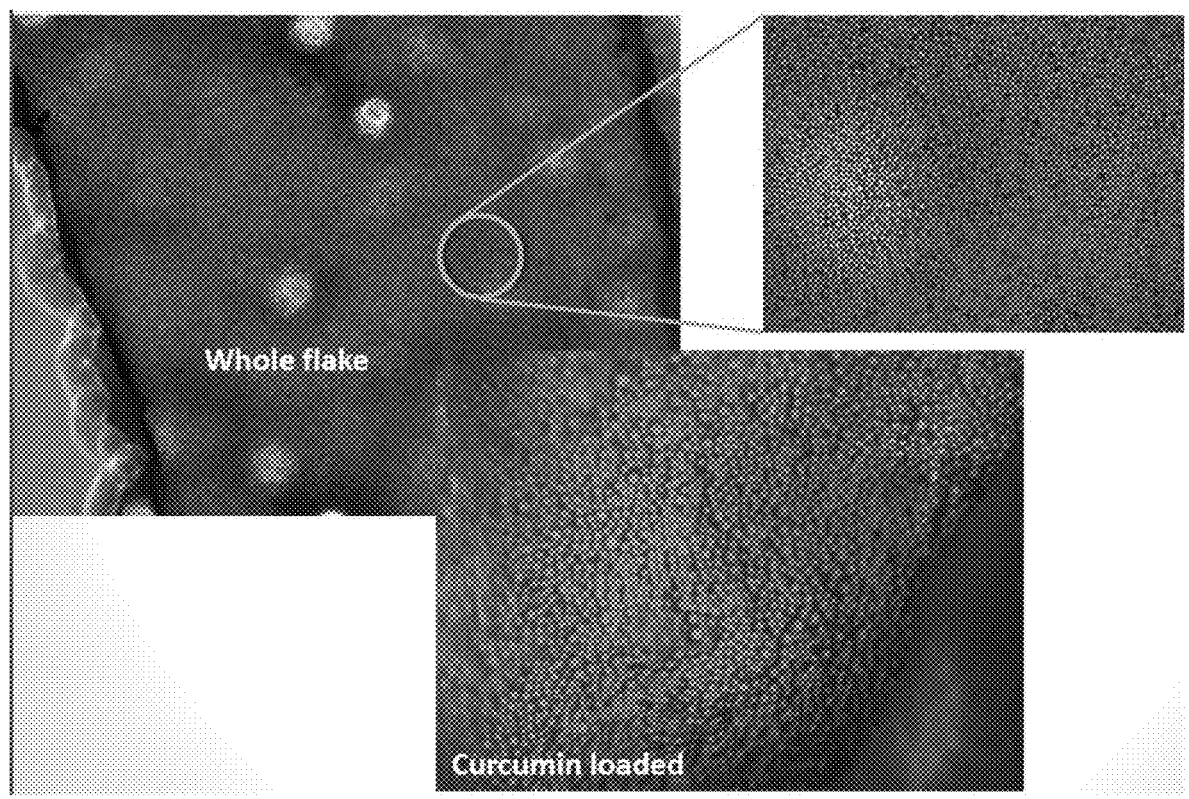
FIG. 16 shows a microscopic image of microparticle flakes after being dried overnight.
Figure 17:
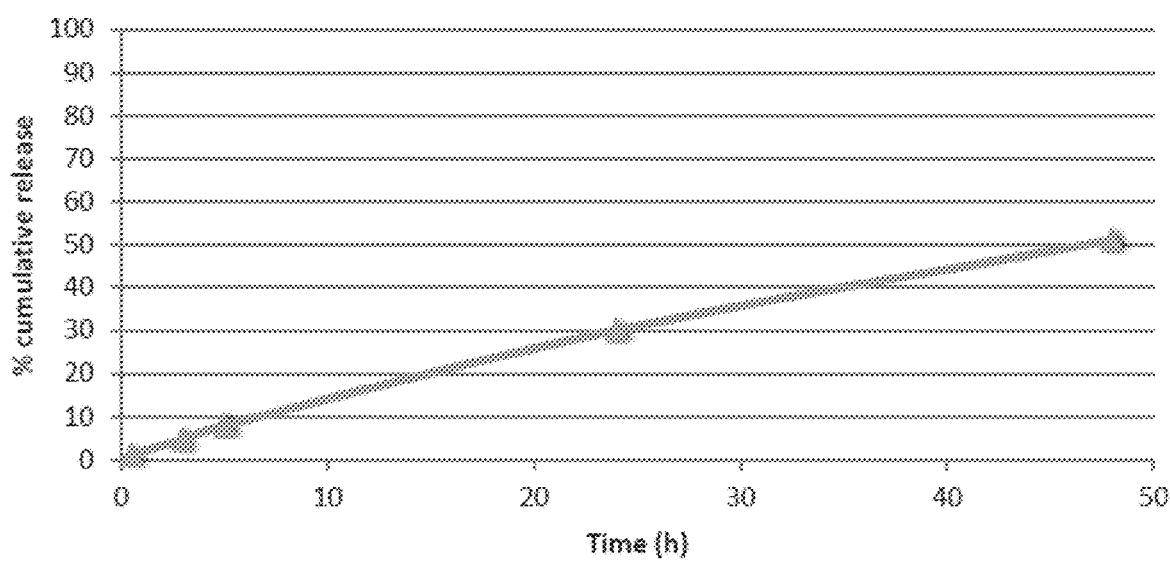
FIG. 17 shows the release profile of curcumin release from microparticle flakes.

It was observed that microparticles thus produced formed "flakes" that could not be re-suspended in THF or PBS buffer solution upon drying. Microscope images of the flakes are shown in FIG. 16 after being dried overnight, and FIG. 17 shows a release profile of curcumin from microscopic flakes. The flakes could not be re-suspended in PBS buffer.

The release profile of curcumin of microparticle flakes produced by the method described above. The release profile is further quantified in Table 6, below.

TABLE 6

| | AUC | Conc (µg/mL) | Dilution | Final Conc (mg/mL) | Efficiency | % Loading |
|---|---|---|---|---|---|---|
| Release Profile of Microparticle Flakes | | | | | | |
| Initial Release | 489.8 | 1.259093597 | 251.8187193 | 0.251818719 | 1.134190112 | 1.937067072 |
| | | | | Total (µg curcumin) | % retention in flakes | |
| Extraction After 48 H | 2782 | 7.151487108 | 143.0297422 | 143.0297422 | 56.79869334 | |

As shown in Table 6 above, 51% of curcumin was released after 48 hours, and 57% was recovered in post-release extraction of the flakes.

Figure 19A:
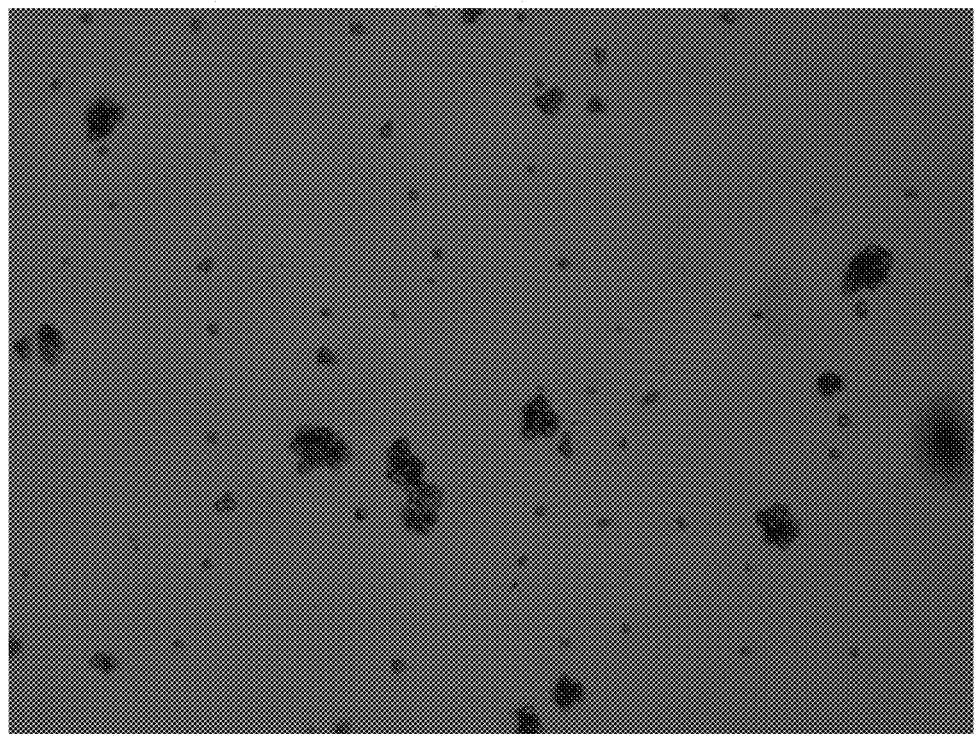
FIG. 19A shows a microscope image of microparticle flakes in water after drying with 2.5% PEG as a co-solvent.
Figure 19B:
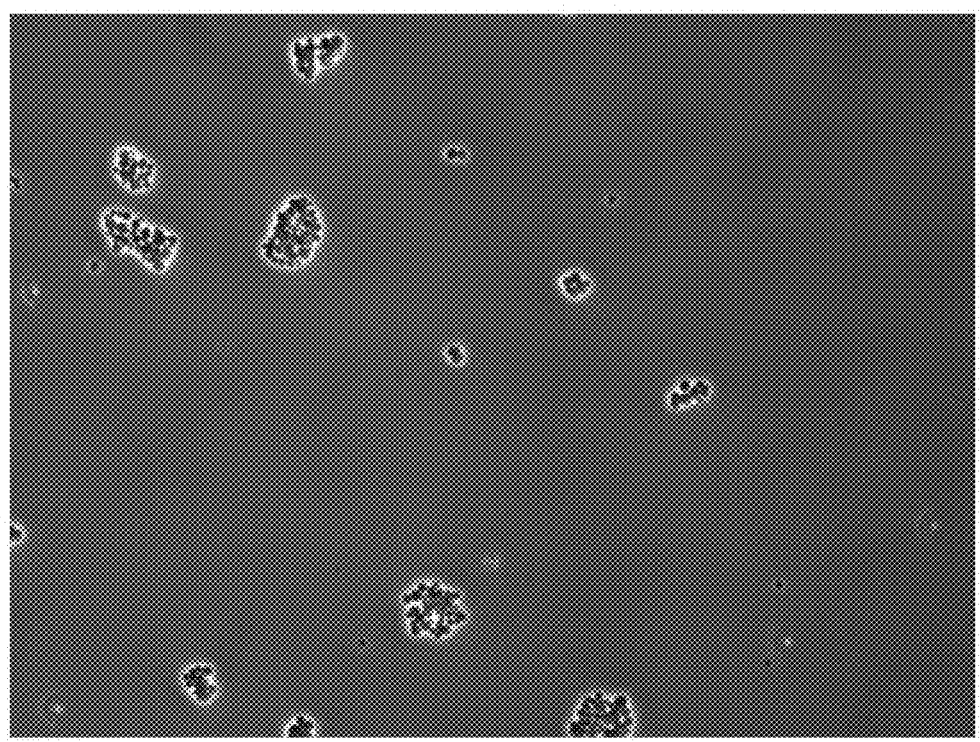
FIG. 19B shows a microscope image of microparticle flakes in THF after drying with 2.5% PEG as a co-solvent.
Figure 19C:
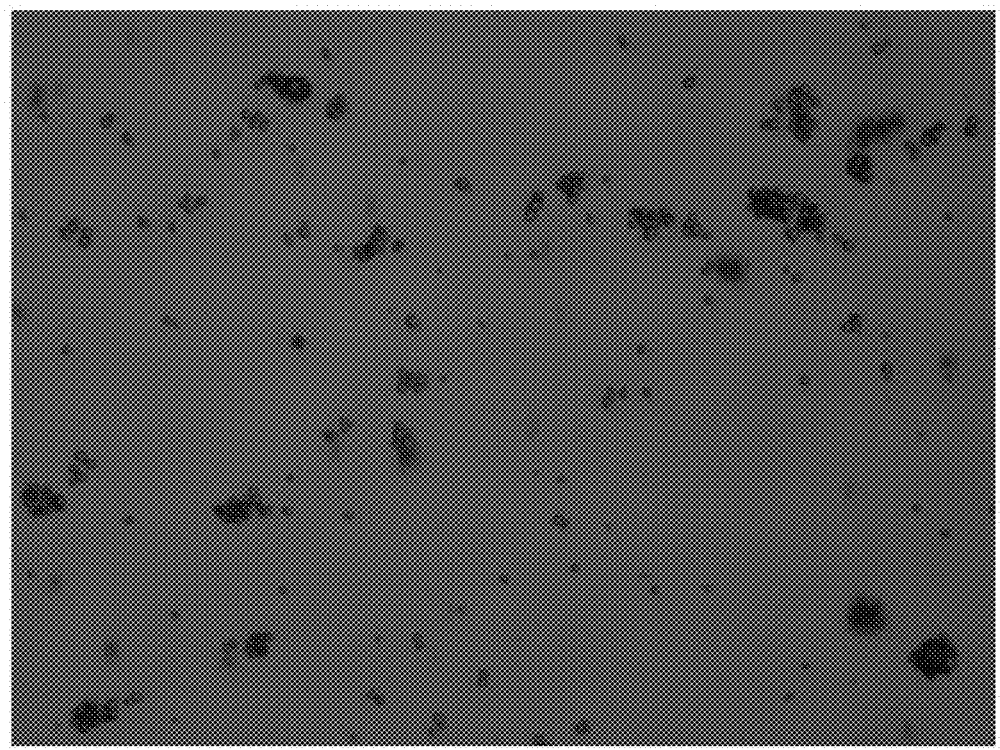
FIG. 19C shows a microscope image of microparticle flakes in water after drying with 5% PEG as a co-solvent.
Figure 19D:
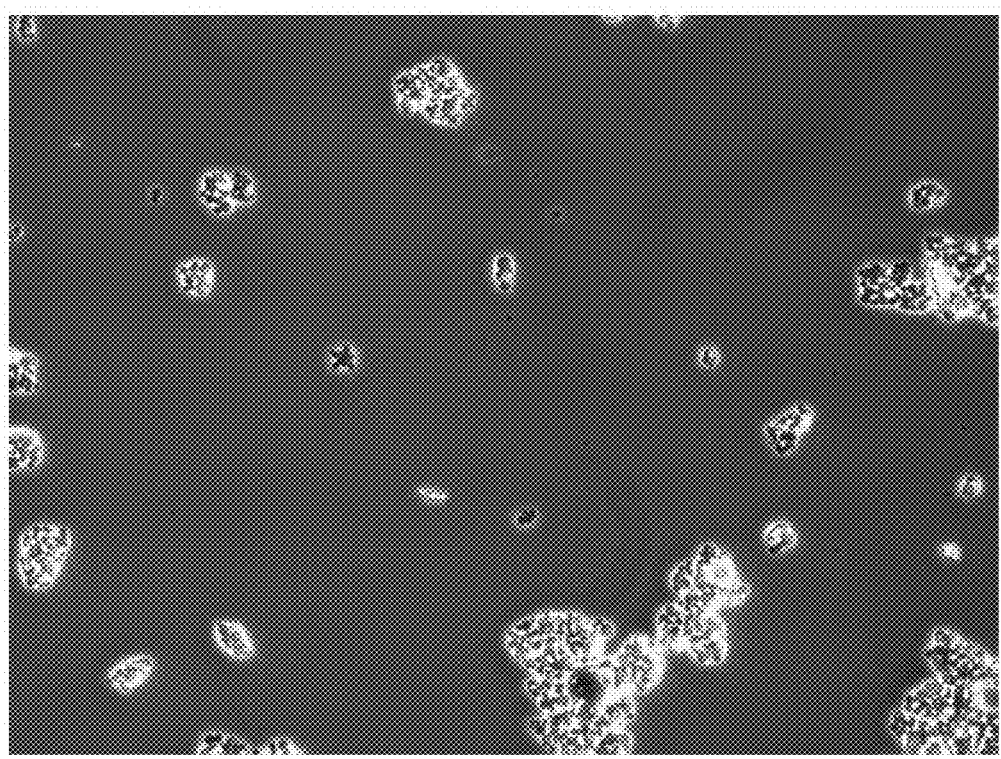
FIG. 19D shows a microscope image of microparticle flakes in THF after drying with 5% PEG as a co-solvent.

In order to address the difficulties re-suspending the microparticle flakes, particles were dried with 25% $PEG_{400}$ as a co-solvent. Particles dried in PEG, included those that had been loaded with curcumin, could be re-suspended in water with Tween or THF. FIGS. 18A and 18B show microscope images of microparticles of the invention after being dried with 25% $PEG_{400}$ as a co-solvent. FIG. 19A shows a microscope image of microparticle flakes in water after drying with 2.5% $PEG_{400}$ as a co-solvent. FIG. 19B shows a microscope image of microparticle flakes in THF after drying with 2.5% $PEG_{400}$ as a co-solvent. FIG. 19C shows a microscope image of microparticle flakes in water after drying with 5% $PEG_{400}$ as a co-solvent. FIG. 19D shows a microscope image of microparticle flakes in THF after drying with 5% $PEG_{400}$ as a co-solvent. FIGS. 18 and 19 demonstrate that as little as 2.5% $PEG_{400}$ was capable of re-suspending microparticle flakes.

Figure 9A:
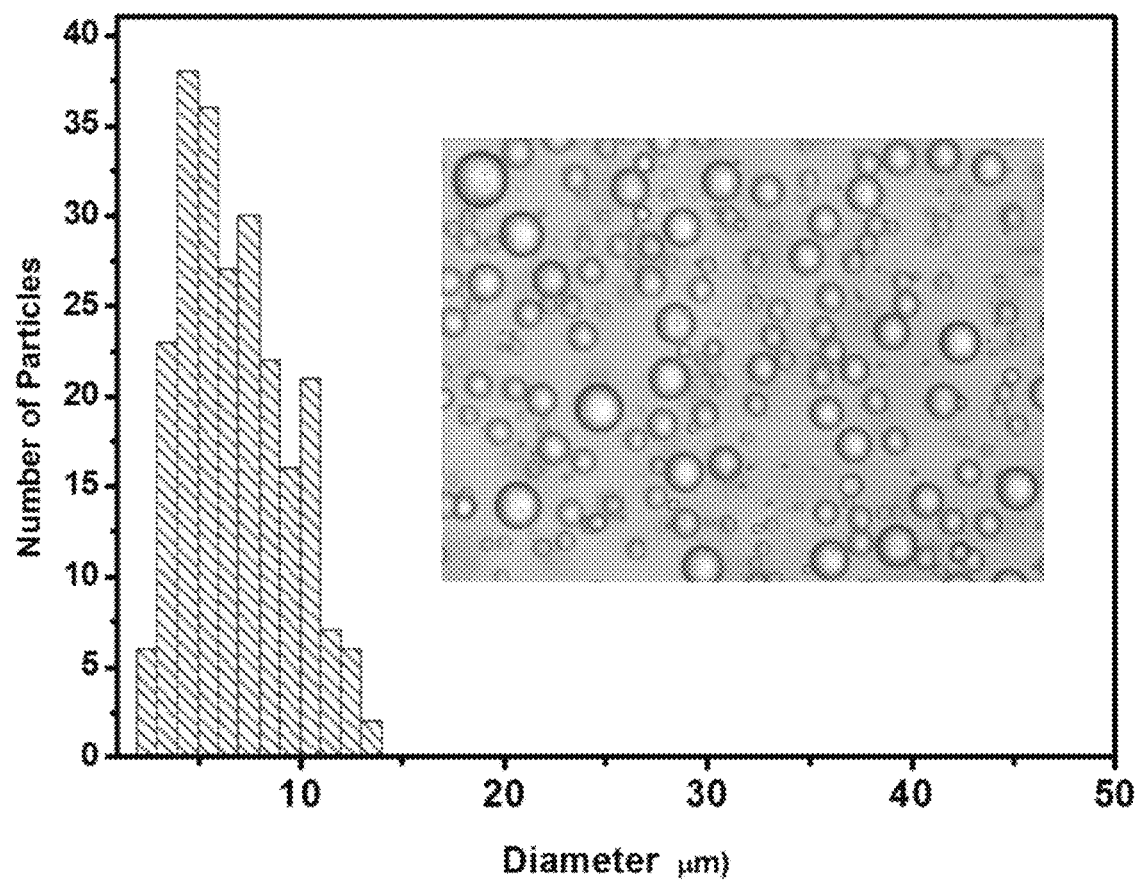
FIG. 9A shows a histogram and an image of 25% PVL-co-PAVL microparticles after crosslinking.
Figure 9B:
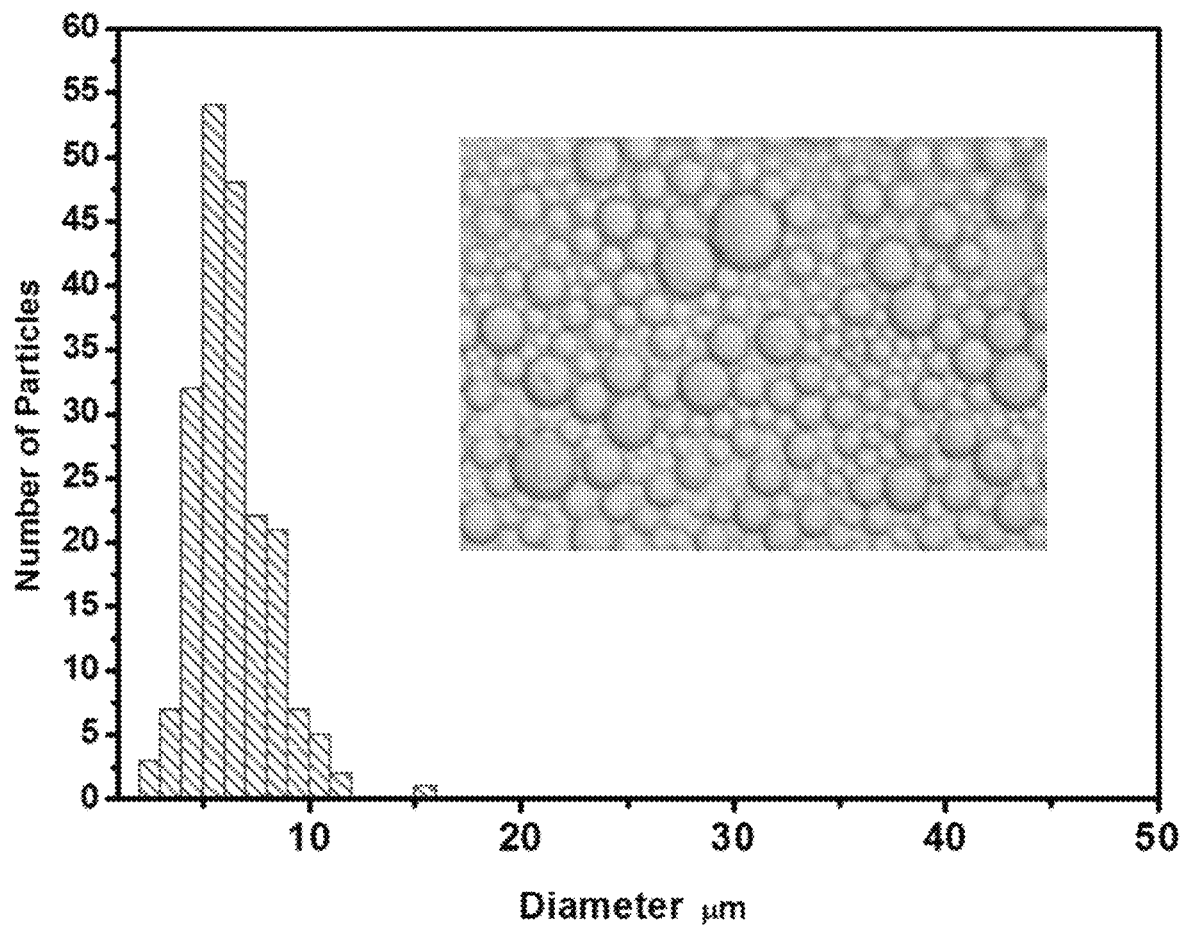
FIG. 9B shows a histogram and microscope image of the same microparticles after a DMSO washing step.
Figure 9C:
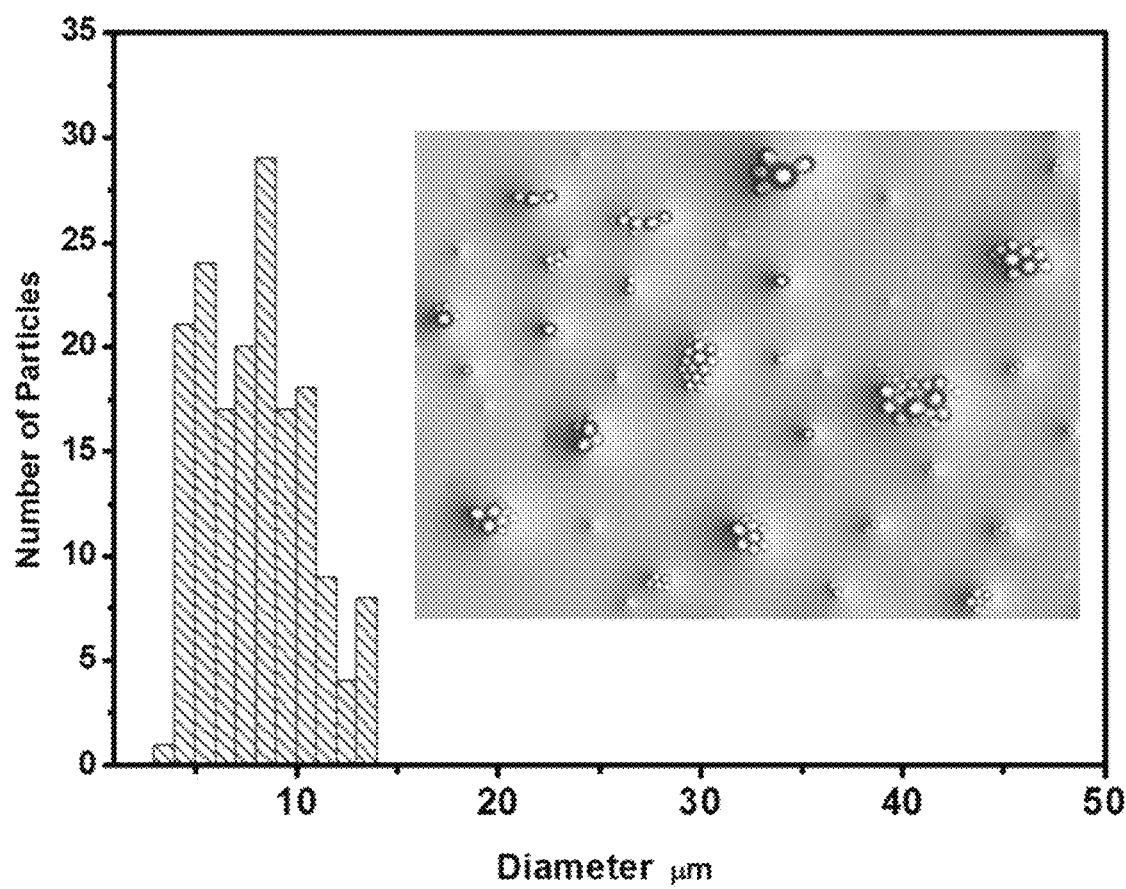
FIG. 9C shows a histogram and microscope image of the particles after an ethanol washing step.
Figure 9D:
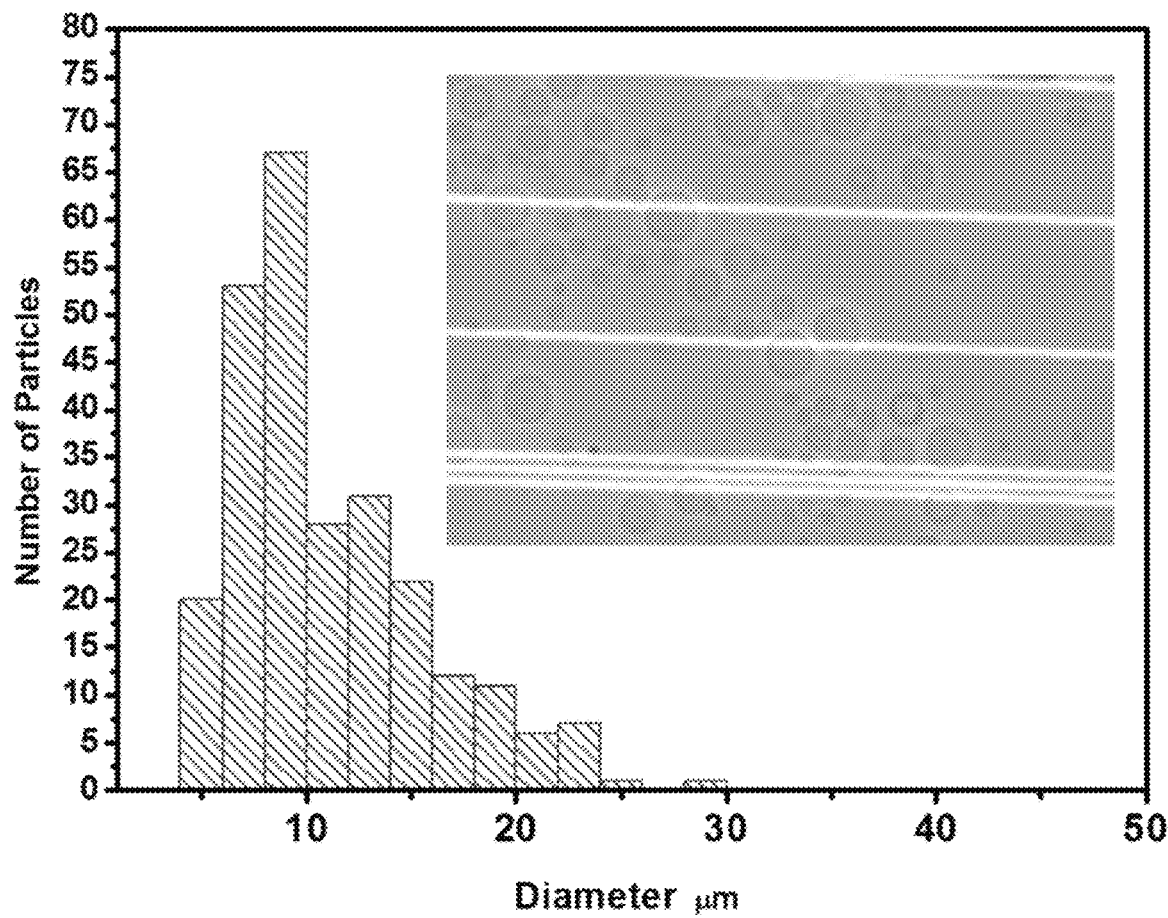
FIG. 9D shows a histogram and microscope image of the particles after swelling in THF.

FIG. 9A shows a histogram and a optical microscope image of 25% PVL-co-PAVL microparticles after crosslinking. The average diameter was 6.8 µm±2.5 nm. FIG. 9B shows a histogram and OM image of the same microparticles after a DMSO washing step (average diameter 6.4 µm±1.8 nm) and FIG. 9C shows a histogram and OM image of the particles after an ethanol washing step (average diameter 8 µm±2.5 nm). FIG. 9D shows a histogram and OM image of the particles after swelling in THF, after which the average diameter was 11.1 µm±4.5 nm. The results show that in some embodiments, suspending the particles in THF causes the particles to swell.

Example 10—Aqueous Drug Solubility

Triamcinolone acetonide, triamcinolone hexacetonide, and paclitaxel were dissolved in water with varying concentrations of surfactants as co-solvents. Sodium dodecyl sulfate (SDS) is an anionic surfactant with a critical micelle concentration (CDC) of 8.2 mM. The hydrophobic lipophilic balance (HLB) is 40. Tween 80 is a non-ionic surfactant with a critical micelle concentration (CMC) of 0.012 mM, and a hydrophobic lipophilic balance (HLB) of 15.

Figure 20A:
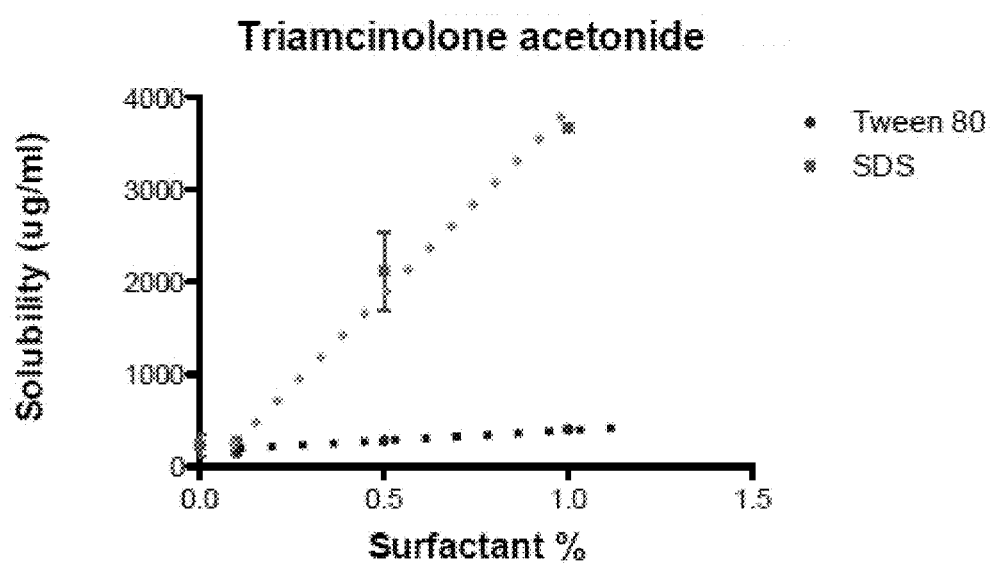
FIG. 20A shows an aqueous solubility plot of triamcinolone acetonide in the presence of surfactants Tween 80 and SDS.
Figure 20B:
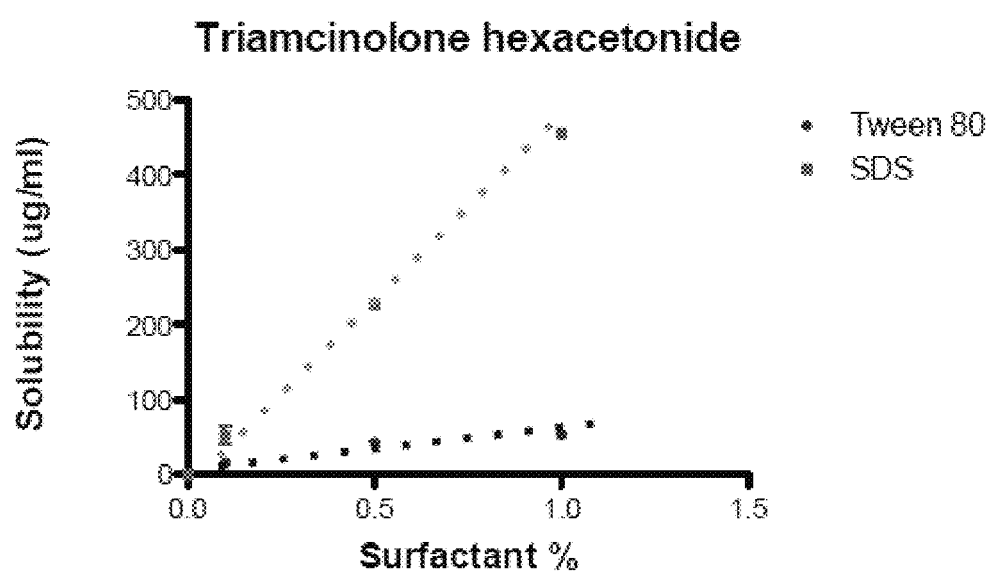
FIG. 20B shows an aqueous solubility plot of triamcinolone hexacetonide in the presence of surfactants Tween 80 and SDS.
Figure 20C:
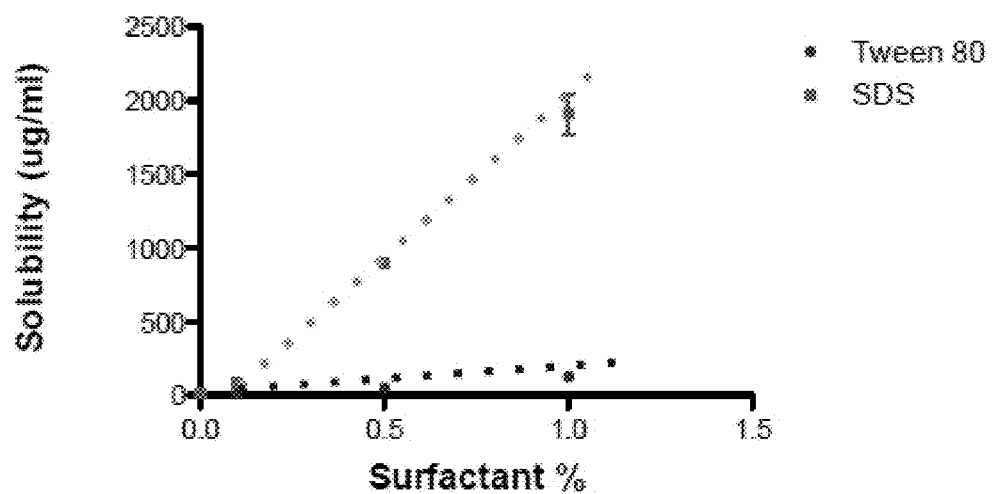
FIG. 20C shows an aqueous solubility plot of paclitaxel in the presence of surfactants Tween 80 and SDS.

FIG. 20 shows that certain drugs can by hydrophobic, and can require addition of surfactants (e.g. sodium dodecyl sulfate and Tween 80) to dissolve in water. FIG. 20A shows an aqueous solubility plot of triamcinolone acetonide in the presence of surfactants Tween 80 and SDS. FIG. 20B shows an aqueous solubility plot of triamcinolone hexacetonide in the presence of surfactants Tween 80 and SDS. FIG. 20C shows an aqueous solubility plot of paclitaxel in the presence of surfactants Tween 80 and SDS.

Example 11—Preliminary Drug Release from Crosslinked Macroparticles

A crosslinked macroparticle weighing about 15 mg comprising PVL-co-PAVL (MW=14760 g/mol, 13% AVL, 87% VL) was loaded with 2.5 mg paclitaxel by overnight soaking in THF followed by the slow addition of 50 mL PBS containing 0.1% Tween.

The macroparticles were suspended in PBS (0.1% Tween) and the release rate was observed. The macroparticles released 5% of the paclitaxel after 3 hours at room temperature and about 5% after 24 hours at room temperature. The loading capacity was found to be 1.7% w/w, and the loading efficiency was 30%.

Figure 21:
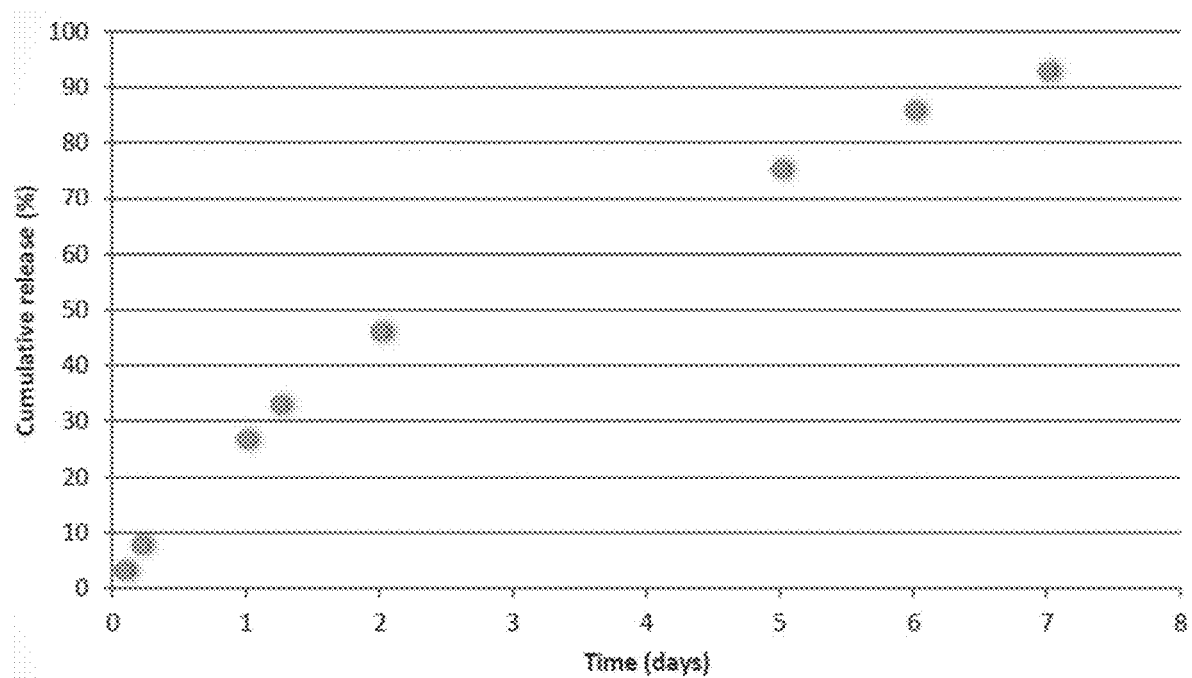
FIG. 21 shows a 7-day release profile of curcumin from a macroparticle.

A second cylinder (was loaded with curcumin and dissolved in THF. The amount of drug in the cylinder was 1.176 mg (9.64% capacity). A release profile is shown in FIG. 21. FIG. 21 shows that almost all of the curcumin is released after about eight days. Without wishing to be bound by theory, it is proposed that mechanical agitation (e.g., stirring with a stir bar) can affect the release parameters of particles of the present disclosure, causing faster release.

Figure 22:
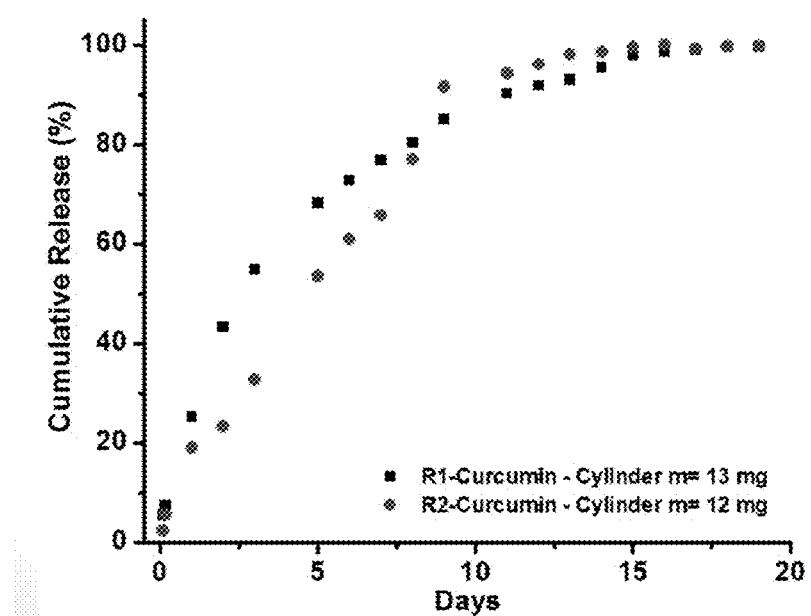
FIG. 22 shows a 20-day curcumin release profile from a 13-mg and 12-mg macroparticle.

FIG. 22 shows a 20-day curcumin release profile from a 13-mg and 12-mg macroparticle.

Figure 23:
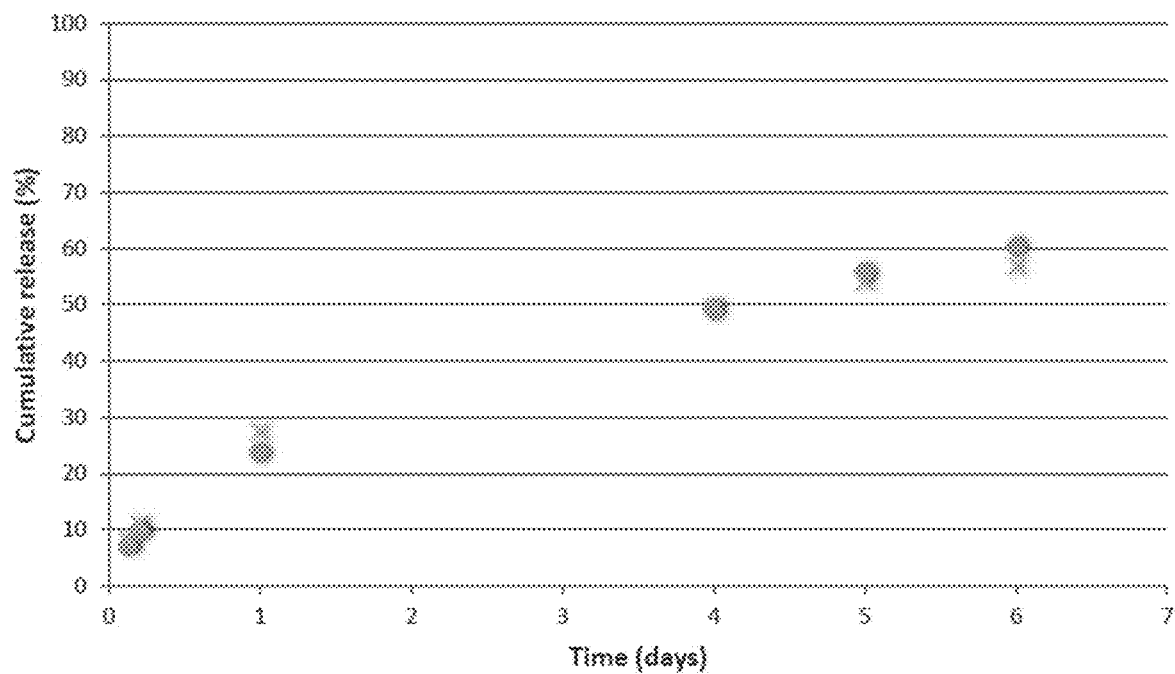
FIG. 23 shows a 6-day release profile of triamcinolone hexacetonide from two macroparticles.

Two cylinders (were loaded with triamcinolone hexacetonide and dissolved in THF. The amount of drug in the first cylinder (labelled with a circle) was 1.118 mg (9.12% capacity), and the amount of drug in the second cylinder (labelled with an "X") was 0.901 (11.651% capacity). A release profile of both cylinders is shown in FIG. 23. FIG. 23 shows that the release profile for both cylinders is very similar, and that about 60% of total drug is released after about 6 days.

Figure 24:
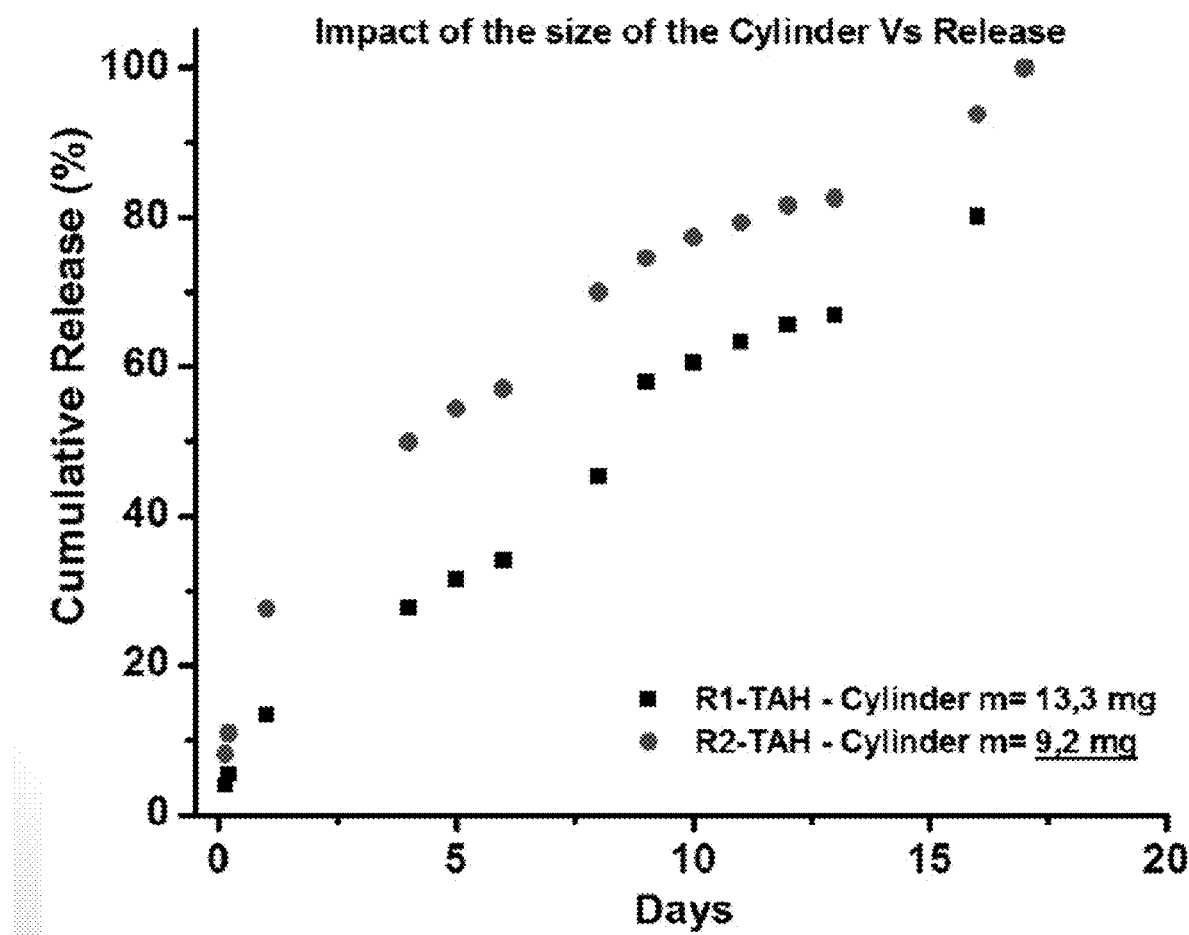
FIG. 24 shows a 20-day triamcinolone hexacetonide release profile from a 13.3-mg and 9.2-mg macroparticle.

FIG. 24 shows a 20-day triamcinolone hexacetonide release profile from a 13.3-mg and 9.2-mg macroparticle.

Figure 25:
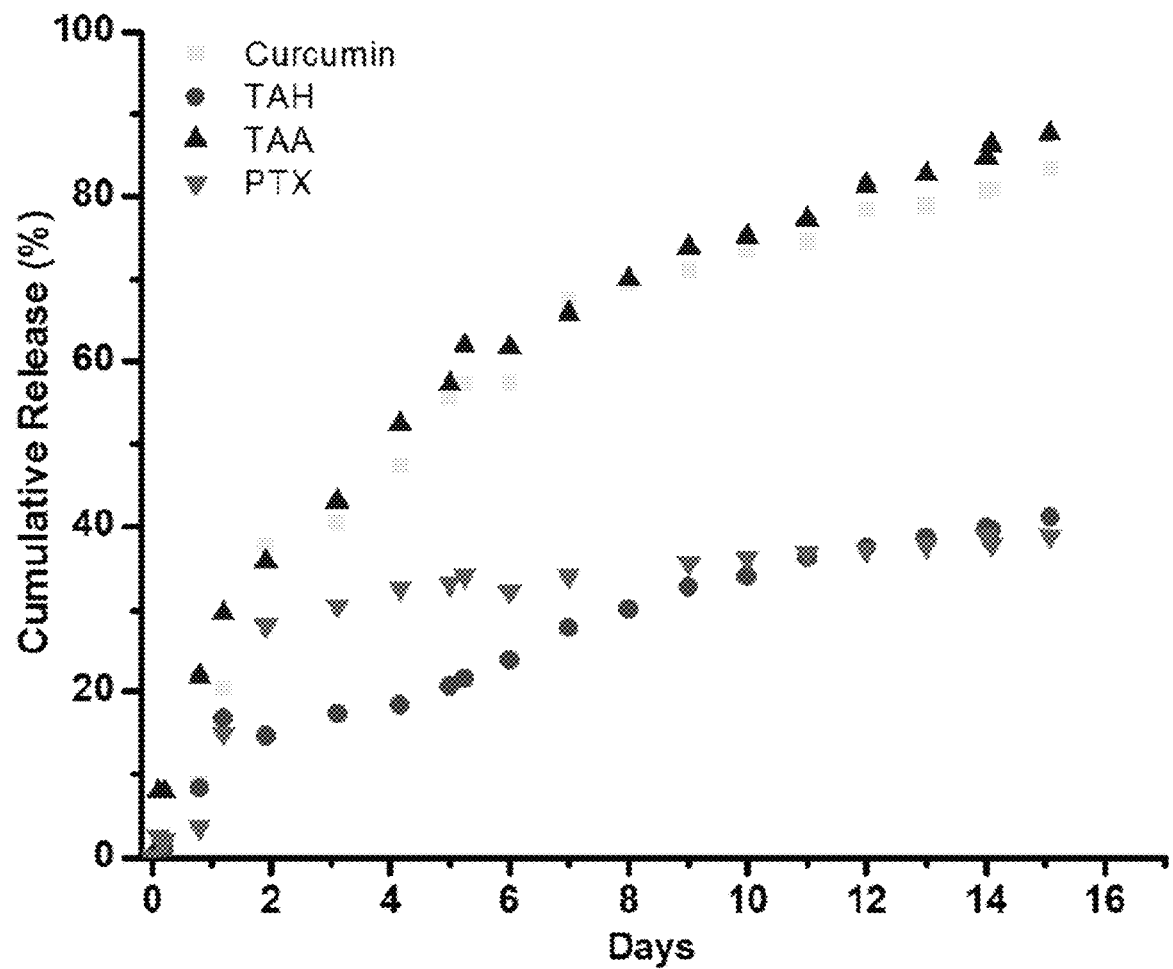
FIG. 25 shows a comparison of the release profiles of curcumin, triamcinolone hexacetonide (TAH), triamcinolone acetonide (TAA), and paclitaxel (PTX).

FIG. 25 shows a comparison of the release profiles of curcumin, triamcinolone hexacetonide (TAH), triamcinolone acetonide (TAA), and paclitaxel (PTX).

Example 12—Photolithography of Microparticles

Figure 26:
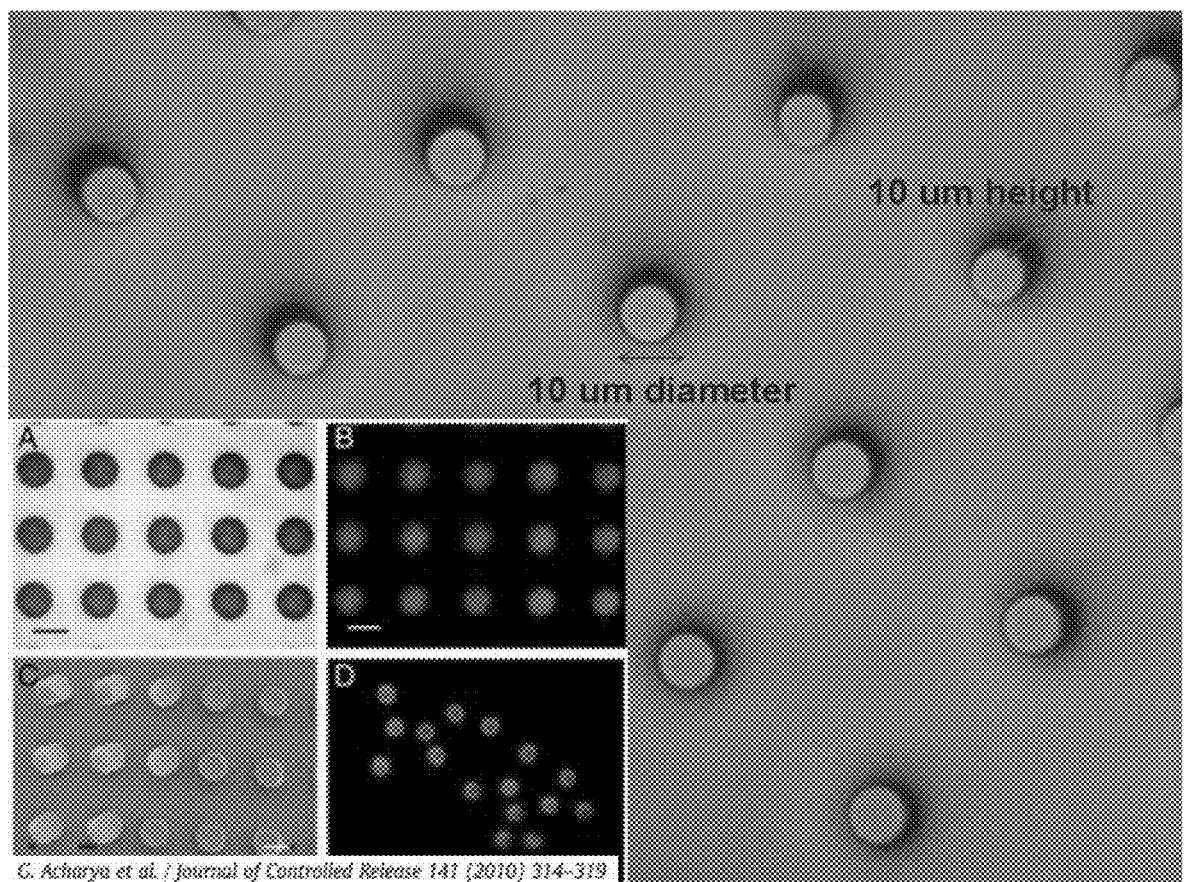
FIG. 26 shows a microscope micrograph of the photolithography template.

Microparticles were fabricated with a silicon master template with 10 µm cylindrical pegs which serve as the inverse for a degradable gelatin template (i.e., the pegs can control the size of the wells. Wells on a gelatin template were filled with polymer solution, crosslinked, and harvested. The resulting particles had a homogenous size distribution. FIG. 26 shows an example micrograph of the photolithography template (G. Acharyo; Journal of Controlled Release 141; 2010; pp. 314-319).

Example 13—Gelatin Hydrogel Template Method for Photolithography

Step 1—Preparation of Template 5 mL of warm 30% (w/v) gelatin solution was poured over a pegged silicon template. The solution and template were cooled in a refrigerator for five minutes. The template was peeled away from the gelatin mold to produce a gelatin mold with individual wells.

Step 2—Preparation of Microparticles

100 µL of 20% PAVL-PVL in dichloromethane was spread on the template along with 1,6-hexanedithiol and 20% DPMA (per allyl group). The template and polymer mixture was covered with a glass slide and irradiated with UV light (365 nm) for ten minutes over ice. The glass slide was removed and the solvent was evaporated. The template was dissolved in water and the microparticles were collected by centrifugation.

Figure 27A:
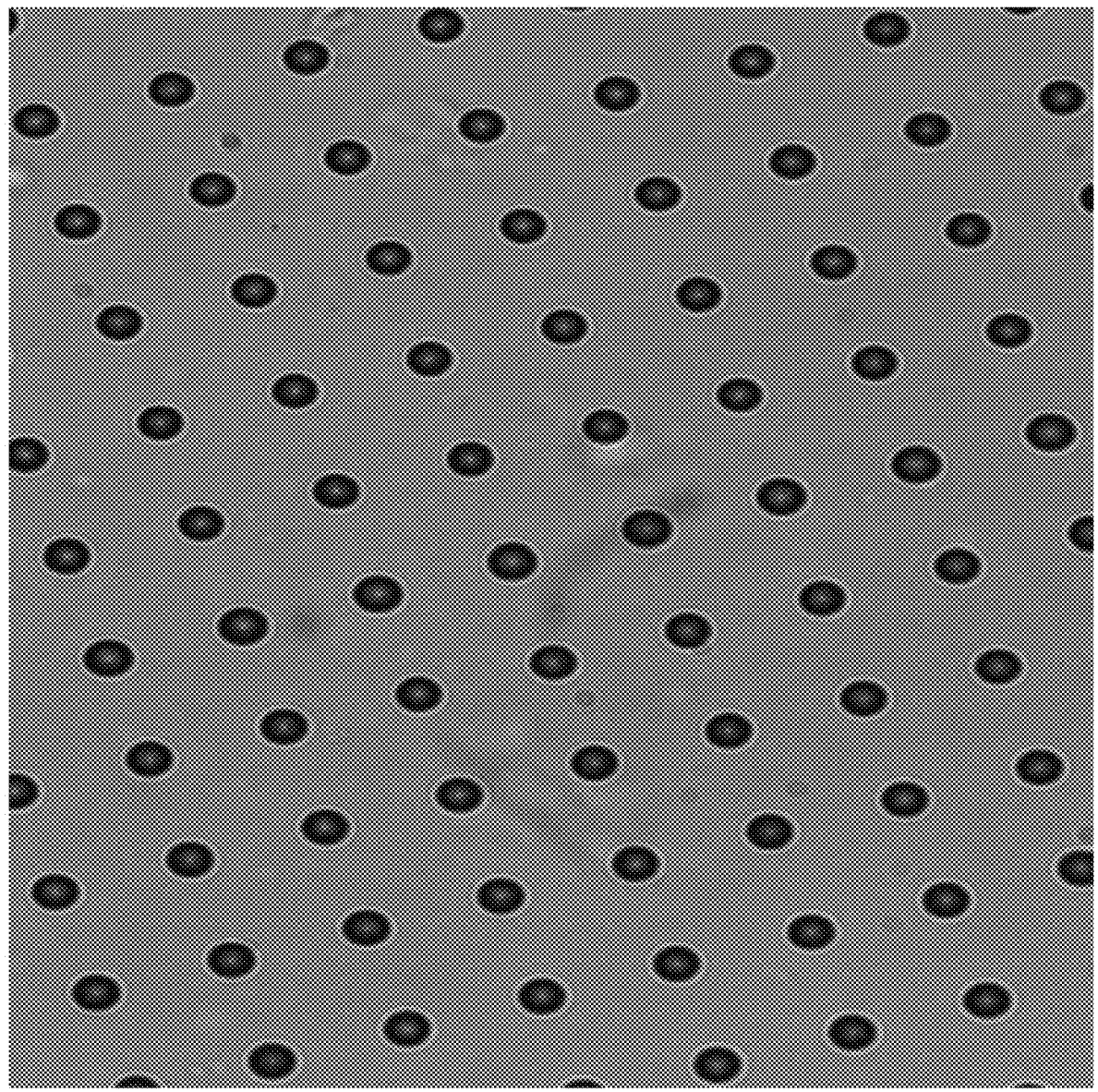
FIG. 27A shows a gelatin template with raised pegs under a microscope.
Figure 27B:
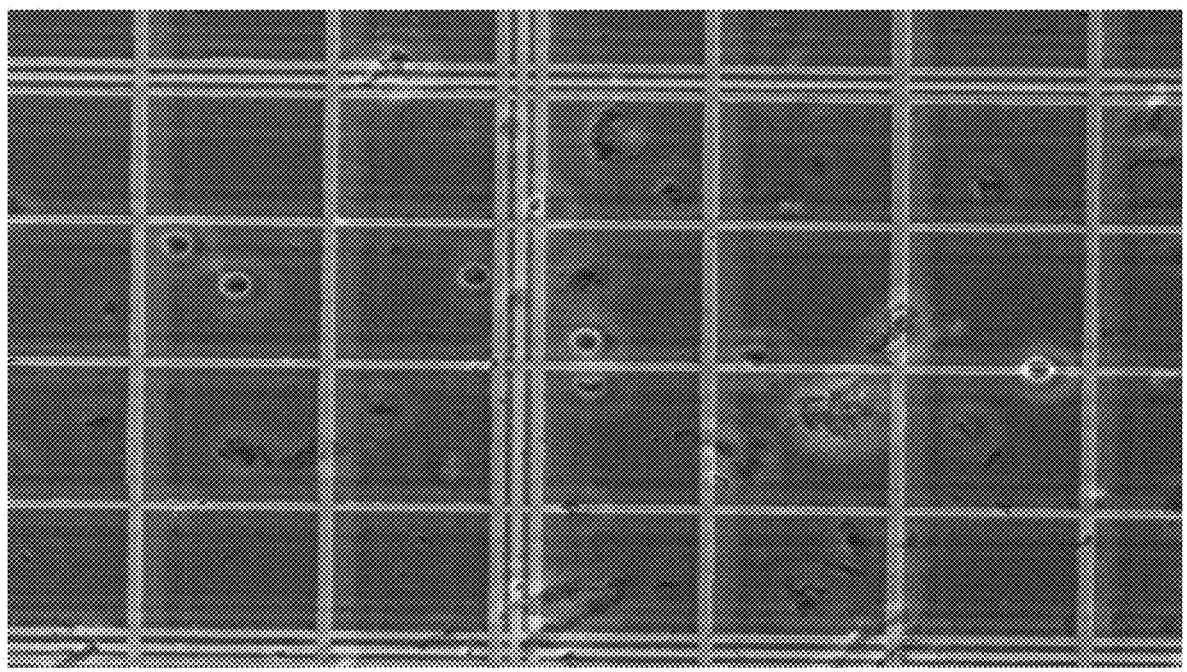
FIG. 27B shows a first microscope image of microparticles prepared by the gelatin hydrogel template method.
Figure 27C:
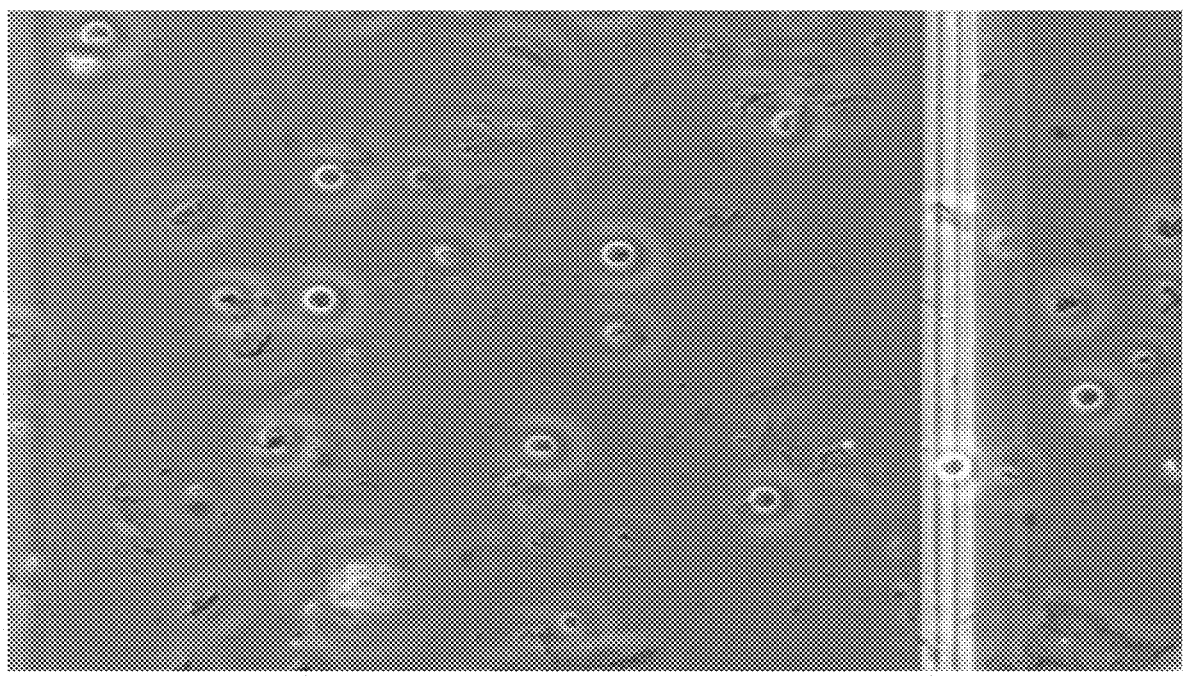
FIG. 27C shows a second microscope image of microparticles prepared by the gelatin hydrogel template method.

FIG. 27A shows a gelatin template with pegs under a microscope. FIGS. 27B and 27C show microscope images of microparticles prepared by the above-method.

Example 14—Stability and Characterization of Microparticles

Figure 28A:
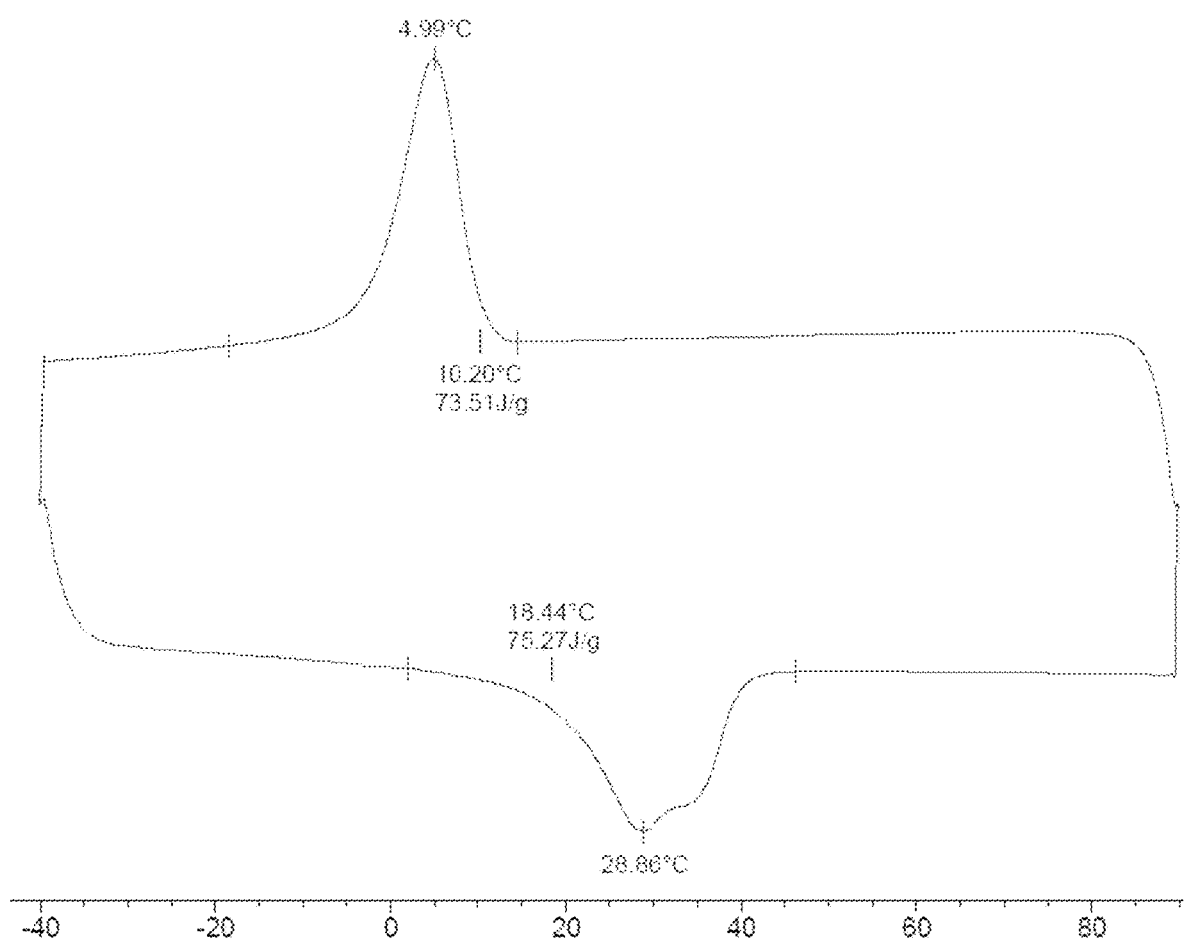
FIG. 28A shows a DSC plot of a control microparticle with no crosslinking.
Figure 28B:
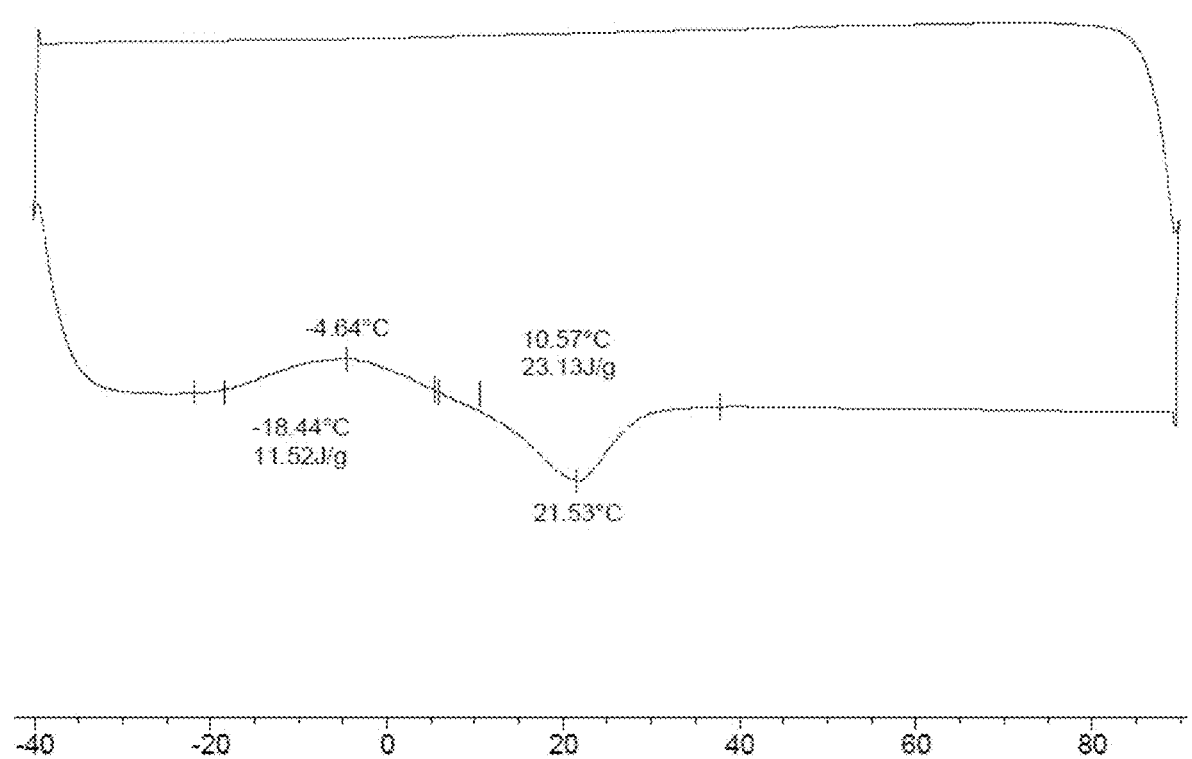
FIG. 28B shows a DSC plot of a microparticle with 50% crosslinking. The DSC plot shows about 30% of crystallinity.
Figure 28C:
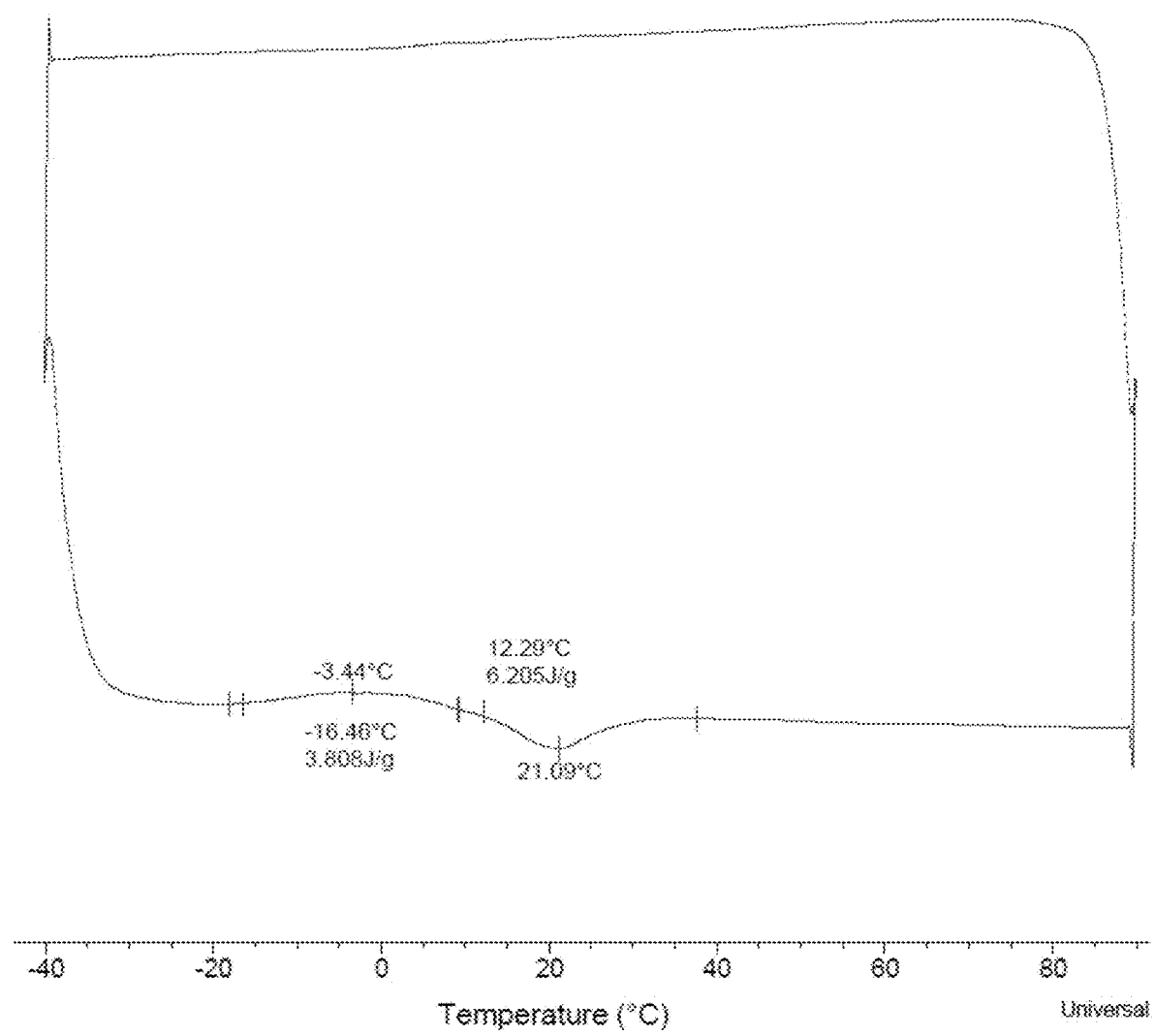
FIG. 28C shows a DSC plot of a microparticle with 100% crosslinking.

Particles of the present disclosure were evaluated using differential scanning calorimetry (DSC). The particles comprised PVL-co-PAVL (MW=6700 g/mol, 19% AVL, 81% VL). FIG. 28 shows DSC plots of microparticles with different degrees of crosslinking. The DSC plots measured the enthalpy of melting ($\Delta°H_m$) of particles freeze dried for four days. FIG. 28A shows a DSC plot of a control microparticle with no crosslinking and shows relatively high crystallinity. FIG. 28B shows a DSC plot of a microparticle with 50% crosslinking. The DSC plot shows relatively low crystallinity. FIG. 28C shows a DSC plot of a microparticle with 100% crosslinking. The DSC plot shows even lower crystallinity than the 50% crosslinked particles.

Figure 29A:
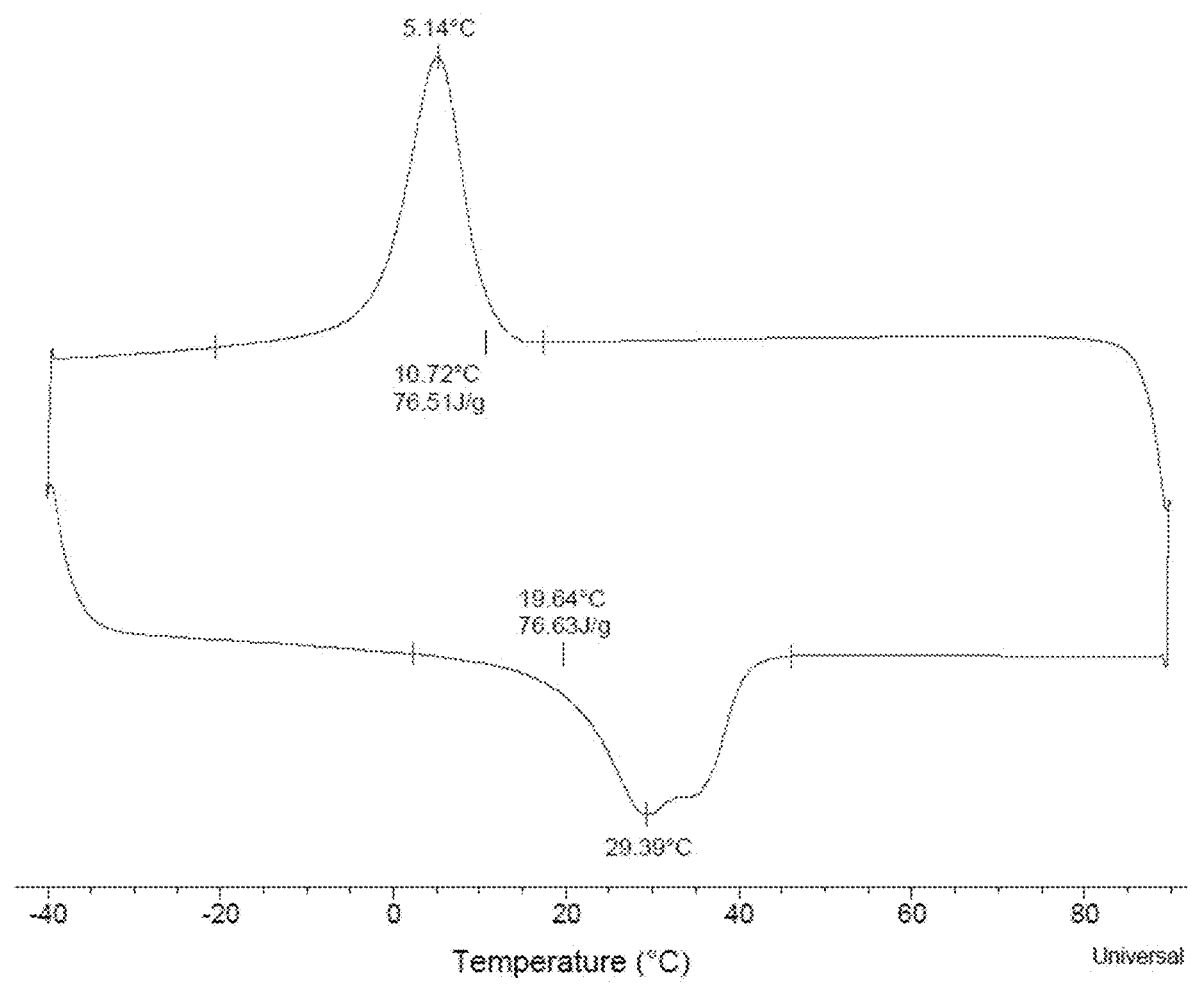
FIG. 29A shows a DSC plot of a control microparticle with no crosslinking.
Figure 29B:
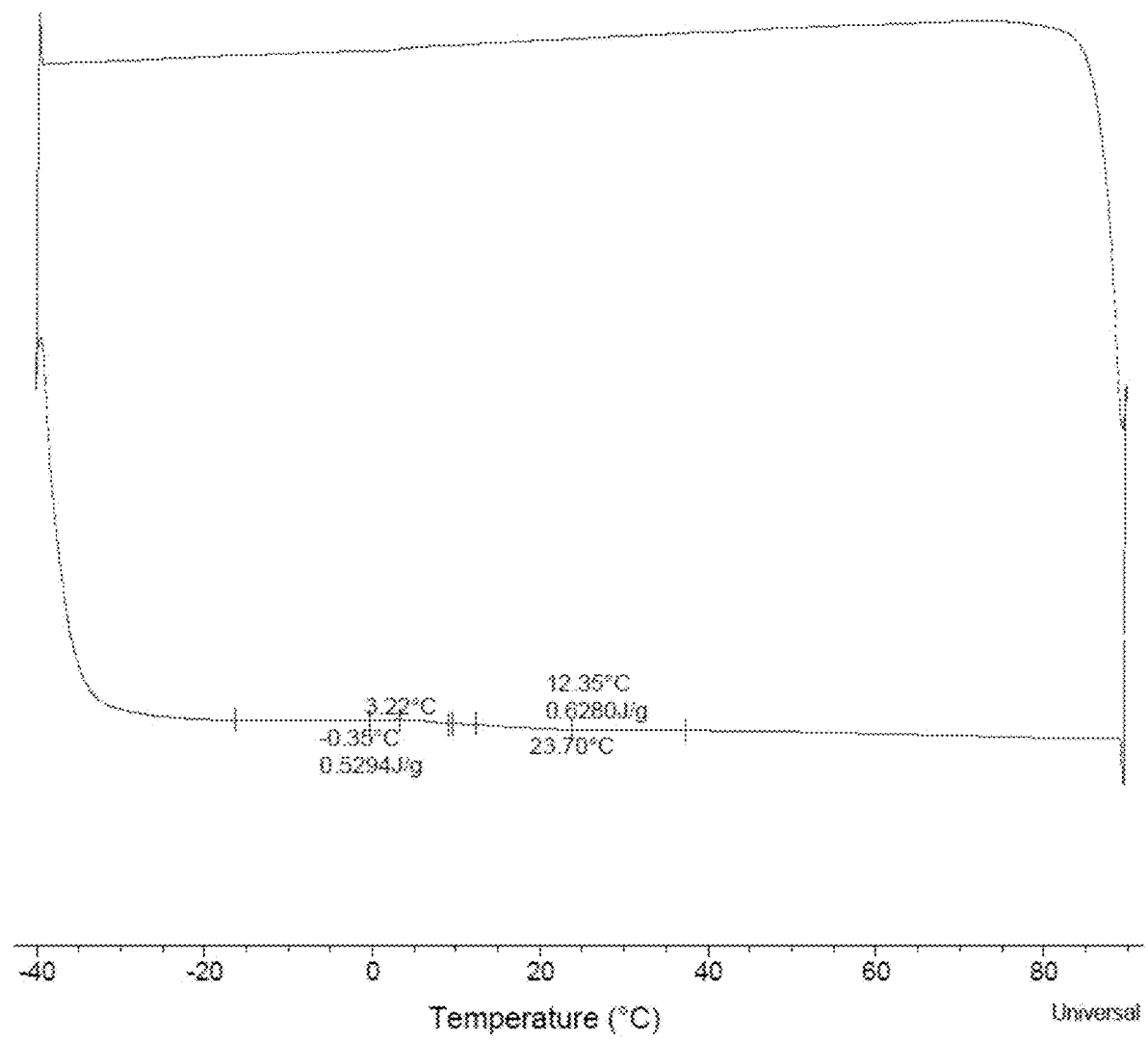
FIG. 29B shows a DSC plot of a microparticle with 50% crosslinking. The DSC plot shows less than 1% crystallinity.
Figure 29C:
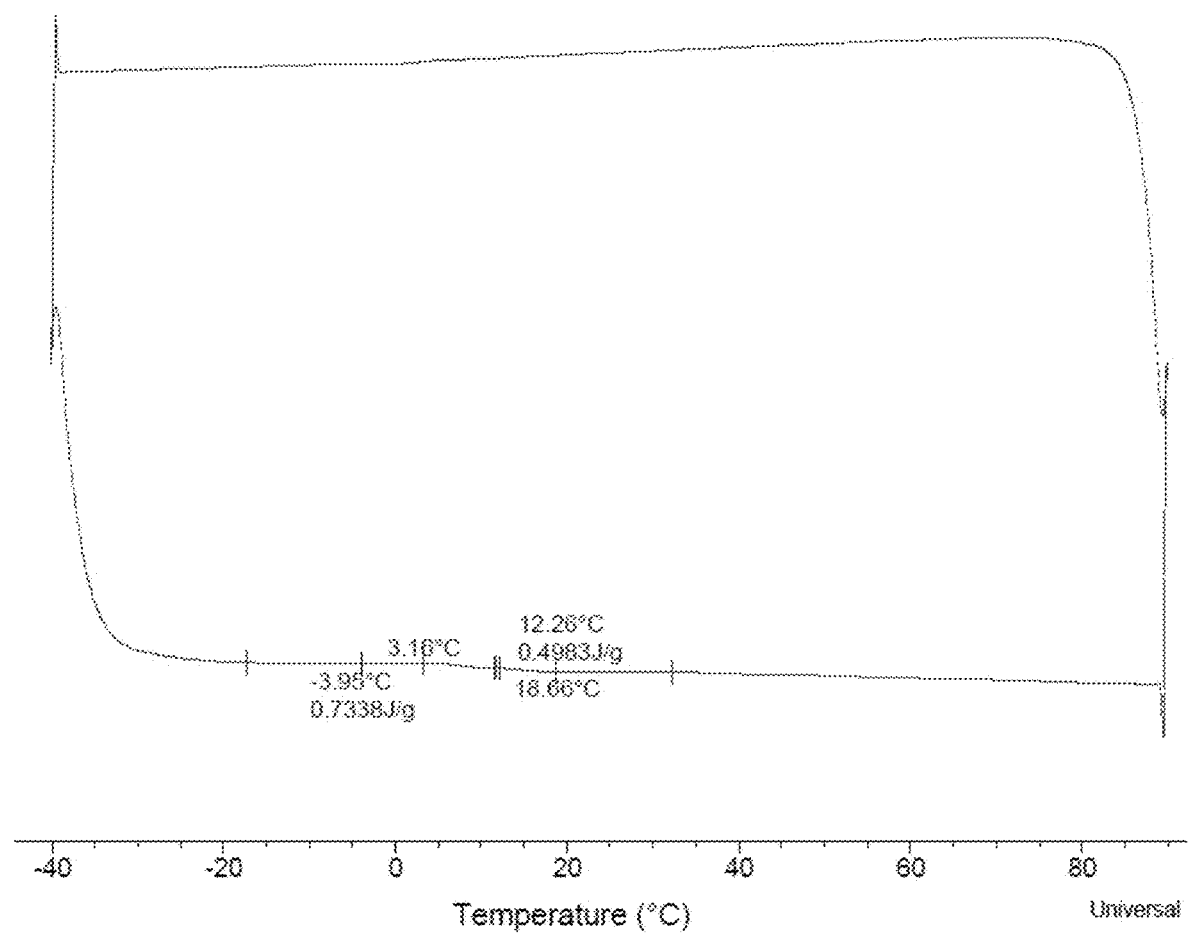
FIG. 29C shows a DSC plot with 100% crosslinking.

Similarly, FIG. 29 shows DSC plots of microparticles with different degrees of crosslinking. The DSC plots measured the enthalpy of melting ($\Delta°H_m$) of particles freeze dried for four days. FIG. 29A shows a DSC plot of a control microparticle with no crosslinking (i.e., just the polymer backbone is analyzed). FIG. 29B shows a DSC plot of a microparticle with 50% crosslinking. The DSC plot shows low crystallinity. FIG. 29C shows a DSC plot with 100% crosslinking. The DSC plot shows low crystallinity. Without wishing to be bound by theory, the low crystallinity of the drug can help facilitate diffusion-mediated release.

The middle trace shows a trace of 10% PAVL microparticles. The number average molecular weight (Mn) was 12,000 and the weight average molecular weight (Mw) was 17,500. The polydispersity index (PDI) was 1.45. The particles were found to be semi-crystalline and the melting temperature was found to be between about 25-35° C.

The top trace shows a trace of 8% PAVL microparticles. The number average molecular weight (Mn) was 32,700 and the weight average molecular weight (Mw) was 50,000. The polydispersity index (PDI) was 1.55. The particles were found to be an amorphous rubber.

Example 15—Efficacy of Particles Against Tumors in Mice

Nude mice were implanted in hind limb with GL261 glioma cells and were treated with fluorescently labeled GIRLRG peptide and daily radiation of 3 Gy for 3 days. Mice were similarly treated with systemic taxol, taxol-loaded, control peptide particles, taxol-loaded targeted microparticles, and naked particles.

Example 16—Preparation of Particles by Crosslinking with Tetrazine-Trans-Cyclooctene Polyvalerolactone (PVL; 50 mg) and poly(trans-cyclooctene)valerolactone (P'COVL; 50 mg (6700 g/mol; 19% (trans-cyclooctene)valerolactone and 81% valerolactone)) and hexanedi-tetrazine (1 tetrazine group per trans-cyclooctene) are dissolved in 1 mL dichloromethane. The solution is added dropwise to 20 mL of water containing 5% polyvinyl alcohol. The mixture is homogenized with stirring (i.e., a Polytron® mechanical homogenizer at 22,000 rpm) for five minutes. The homogenized mixture is stirred for about an additional 12-48 hours.

The mixture is then centrifuged at 4000 rpm at 10° C. for 10 minutes. The aqueous solution containing polyvinyl alcohol is poured off and the particles are rinsed with distilled water. The particles are then centrifuged and rinsed with water as above an additional three times.

Example 17—Formation of Microparticles by Electrospray

Polyallylvalerolactone (PAVL; 100 mg (6700 g/mol; 19% allylvalerolactone and 81% valerolactone)) and hexanedithiol (1 —SH group per alkene) are dissolved in 1 mL dichloromethane. 2,2-Dimethoxy-2-phenylacetophenone (DMPA; 0.2 equivalents per alkene) is added and the solution is sprayed on to a 20 mL water bath containing 5% polyvinyl alcohol using an electrosprayer. The electrosprayed droplets and the homogenized mixture are irradiated at 365 nm-4 mW under stirring for 30 minutes.

The mixture is stirred for 3 hours to allow the dichloromethane to evaporate. The mixture is then centrifuged at 4000 rpm at 10° C. for 10 minutes. The aqueous solution containing polyvinyl alcohol is poured off and the particles are rinsed with distilled water. The particles are then centrifuged and rinsed with water as above an additional three times.

The particles are then dispersed in DMSO and centrifuged at 4000 rpm at 20° C. for ten minutes. The DMSO is poured off and the process is repeated another two times.

Example 18—Formation of Microparticles by Spray Drying

Polyallylvalerolactone (PAVL; 100 mg (6700 g/mol; 19% allylvalerolactone and 81% valerolactone)) and hexanedithiol (1 —SH group per alkene) are dissolved in 1 mL dichloromethane. 2,2-Dimethoxy-2-phenylacetophenone (DMPA; 0.2 equivalents per alkene) is added and the solution is sprayed on to a 20 mL water bath containing 5% polyvinyl alcohol using a spray dryer. The spray-dried droplets and the homogenized mixture are irradiated at 365 nm-4 mW under stirring for 30 minutes.

The mixture is stirred for 3 hours to allow the dichloromethane to evaporate. The mixture is then centrifuged at 4000 rpm at 10° C. for 10 minutes. The aqueous solution containing polyvinyl alcohol is poured off and the particles are rinsed with distilled water. The particles are then centrifuged and rinsed with water as above an additional three times.

The particles are then dispersed in DMSO and centrifuged at 4000 rpm at 20° C. for ten minutes. The DMSO is poured off and the process is repeated another two times.

EQUIVALENTS

While the present invention has been described in conjunction with the specific embodiments set forth above, many alternatives, modifications and other variations thereof will be apparent to those of ordinary skill in the art. All such alternatives, modifications and variations are intended to fall within the spirit and scope of the present invention.

The invention claimed is:

1. A crosslinked degradable particle, comprising: a polyester of the Formula I:

$$\text{(I)}$$

wherein:
$R^1$ is independently, at each occurrence, —H, or —$C_1$-$C_6$ alkyl;
$R^2$ is independently, at each occurrence, —H, or —$C_1$-$C_6$ alkyl;
$R^3$ is independently, at each occurrence, —H, or —$C_1$-$C_6$ alkyl;
a is 0, 1, or 2;
m is independently, at each occurrence, an integer between 1 and 100, inclusive;
n is independently, at each occurrence, an integer between 1 and 100, inclusive;
p is independently, at each occurrence, an integer between 0 and 5, inclusive;
q is independently, at each occurrence, an integer between 0 and 100, inclusive;
r is independently, at each occurrence, an integer between 0 and 100, inclusive; and
t is independently, at each occurrence, an integer between 0 and 5, inclusive; and
wherein the crosslinked degradable particle has a diameter between about 5 μm and about 100 μm,
wherein the crosslinked degradable particle is formed from a process that includes emulsifying a solution in an aqueous phase, the solution including polyester backbones comprising polyvalerolactone containing a plurality of allyl groups, a multifunctional thiol, and a radical initiator in at least one solvent,
and wherein the crosslinked degradable particle is configured to release a drug dispersed therein over a period of at least one month in an aqueous environment.

2. The crosslinked degradable particle of claim 1, wherein the particle has a diameter between about 5 μm and about 20 μm.

3. The crosslinked degradable particle of claim 1, wherein the particle has a diameter between about 7 μm and about 15 μm.

4. The crosslinked degradable particle of claim 1, wherein the particle has a diameter of about 10 μm.

5. The crosslinked degradable particle of claim 1, wherein the drug is selected from the group consisting of triamcinolone acetonide, triamcinolone hexacetonide, and paclitaxel.

6. The crosslinked degradable particle of claim 1, wherein the drug is contained within the particle by noncovalent interactions.

7. The crosslinked degradable particle of claim 1, wherein the particle comprises polyvalerolactone as part of the polyester backbone.

8. The crosslinked degradable particle of claim 1, wherein the particle comprises polycaprolactone as part of the polyester backbone.

9. The crosslinked degradable particle of claim 1, wherein the particle comprises polylactic acid as part of the polyester backbone.

10. The crosslinked degradable particle of claim 1, wherein the particle comprises polyglycolic acid as part of the polyester backbone.

11. The crosslinked degradable particle of claim 1, wherein the particle is biodegradable.

12. The crosslinked degradable particle of claim 1, wherein the particle degrades as it releases the drug.

13. The crosslinked degradable particle of claim 1, wherein the particle further comprises polyethylene glycol.

* * * * *